United States Patent
Ralph et al.

(10) Patent No.: US 7,332,270 B1
(45) Date of Patent: Feb. 19, 2008

(54) DIAGNOSIS OF DISEASE STATE USING MRNA PROFILES IN PERIPHERAL LEUKOCYTES

(75) Inventors: David Ralph, Edmond, OK (US); Gang An, Oklahoma City, OK (US); S. Mark O'Hara, Oklahoma City, OK (US); Robert Veltri, Oklahoma City, OK (US)

(73) Assignee: Urocor, Inc., Oklahoma City, OK (US)

( * ) Notice: Subject to any disclaimer, the term of this patent is extended or adjusted under 35 U.S.C. 154(b) by 739 days.

(21) Appl. No.: 09/660,568

(22) Filed: Sep. 11, 2000

Related U.S. Application Data

(62) Division of application No. 09/046,894, filed on Mar. 24, 1998, now Pat. No. 6,190,857.

(60) Provisional application No. 60/041,576, filed on Mar. 24, 1997.

(51) Int. Cl.
*C12Q 1/68* (2006.01)
*C12P 19/34* (2006.01)
*C07H 21/04* (2006.01)

(52) U.S. Cl. .......................... 435/6; 435/91.2; 536/23.1; 536/24.31; 536/24.33

(58) Field of Classification Search .................... 435/4, 435/6, 7.1; 556/23.1, 24.33, 24.31
See application file for complete search history.

(56) References Cited

U.S. PATENT DOCUMENTS

| | | | |
|---|---|---|---|
| 5,236,844 A | 8/1993 | Basset et al. | 435/320.1 |
| 5,262,311 A | 11/1993 | Pardee et al. | 435/91.2 |
| 5,440,021 A | 8/1995 | Chuntharapai et al. | 530/388.22 |
| 5,459,037 A | 10/1995 | Sutcliff et al. | 435/6 |
| 5,539,096 A | 7/1996 | Babaï et al. | 536/24.3 |
| 5,543,296 A | 8/1996 | Sobol et al. | 435/6 |
| 5,677,125 A | 10/1997 | Holt et al. | 435/6 |

FOREIGN PATENT DOCUMENTS

| | | |
|---|---|---|
| EP | WO 97/19097 | 5/1997 |
| WO | WO 94/10343 | 5/1994 |
| WO | WO 96/17080 | 6/1996 |
| WO | WO 96/21671 | 7/1996 |
| WO | WO 98/10098 | 3/1998 |
| WO | WO 99/15658 | 4/1999 |

OTHER PUBLICATIONS

Heindenreich et al., Cancer vol. 43:1308-1313, 1979.*
Alcaraz, Antonio, et al., "Aneuploidy and Aneusomy of Chromosome 7 Detected by Fluorescence in Situ Hybridization Are Markers of Poor Prognosis in Prostate Cancer", *Cancer Research*, 54:3998-4002, 1994.
American Type Culture Collection, "Catalogue of cell lines & hybridomas," 7th Ed.pp. 150 and 308, 1992.
An, G., et al., Isolation of Genes differentially expressed in prostate cancer cells with metastic potential by arbitrarily-primed differential analyses (ADA), *Proc. Amer. Assn. Canc. Res.*, 36:82, Abstract #491, 1995.
Andrawis et al., "Expression of interleukin-8 in prostate cancer, benign prostatic hyperplasia, and bladder cancer," *Proc. Am. Urol. Assn.*, 155(5):512A, Absract #804, 1996.
Bookstein, Robert, et al., "Supression of Tumorigenicity of Human Prostate Carcinoma Cells by Replacing a Mutated RB Gene", *Science*, 247:712-715, 1990.
Bookstein, Robert, et al., "Promoter deletion and loss of retinoblastoma gene expression in human prostate carcinoma", *Proc. Natl. Acad. Sci. USA*, 87:7762-7766, 1990.
Bova, G. Steven, et al., "Homozygous Deletion and Frequent Allelic Loss of Commerce of Chromosome 8p22 Loci in Human Prostate Cancer", *Cancer Research*, 53:3869-3873, 1993.
Carter, Bob S., et al., "Allelic loss of chromosomes 16q and 10q in human prostate cancer", *Proc. Natl. Acad. Sci. USA*, 87:8751-8755, 1990.
Damaj et al., "Identification of G-protein binding sites of the human interleukin-8 receptors by functional mapping of the intracellular loops," *FASEB J.*, 10:1426-1434, 1996.
Greene et al., "Correlation of metastasis-related gene expression with metastatic potential in human prostate carcinoma cells implanted in nude mice using an in situ messenger RNA hybridization technique," *Am. J. Pathol.*, 150(5):1571-1582, 1997.
International Search Report dated Mar. 20, 1998 (PCT/US97/22105).
Ivanova and Belyavsky, "Identification of differentially expressed genes by restriction endonuclease-based gene expression fingerprinting," *Nucl. Acids Res.*, 23(15):2954-2958, 1995.
Macoska, Jill A., et al., "Fluorescence in Situ Hybridization Analysis of 8p Allelic Loss and Chromosome 8 Instability in Human Prostate Cancer", *Cancer Research*, 54:3824-3830, 1994.
Matsushima et al., "Molecular cloning of a human monocyte-derived neutrophil chemotactic factor (MDNCF) and the induction of MDNCF mRNA by interleukin 1 and tumor necrosis factor," *J. Exp. Med.*, 167(6):1883-1893, 1988.
Nomura, "HumamRNA for KIAA0262 gene, complete cds," 1997, Database GenBank on STN, GenBack Accession No. D87451.

(Continued)

*Primary Examiner*—Sean McGarry
(74) *Attorney, Agent, or Firm*—Fulbright & Jaworski L.L.P.

(57) ABSTRACT

Disclosed are diagnostic techniques for the detection of human disease states that affect gene expression in peripheral leukocytes. The invention relates particularly to probes and methods for evaluating the presence of RNA species that are differentially expressed in the peripheral blood of individuals with such a disease state compared to normal healthy individuals. The invention further relates to methods for detection of protein species that are differentially expressed in the peripheral blood of individuals with such a disease state compared to normal healthy individuals. Genetic probes, antibody probes and methods useful in monitoring the progression and diagnosis of two specific disease states, prostatic cancer and breast cancer, are described.

7 Claims, 25 Drawing Sheets

OTHER PUBLICATIONS

Figure 1A:
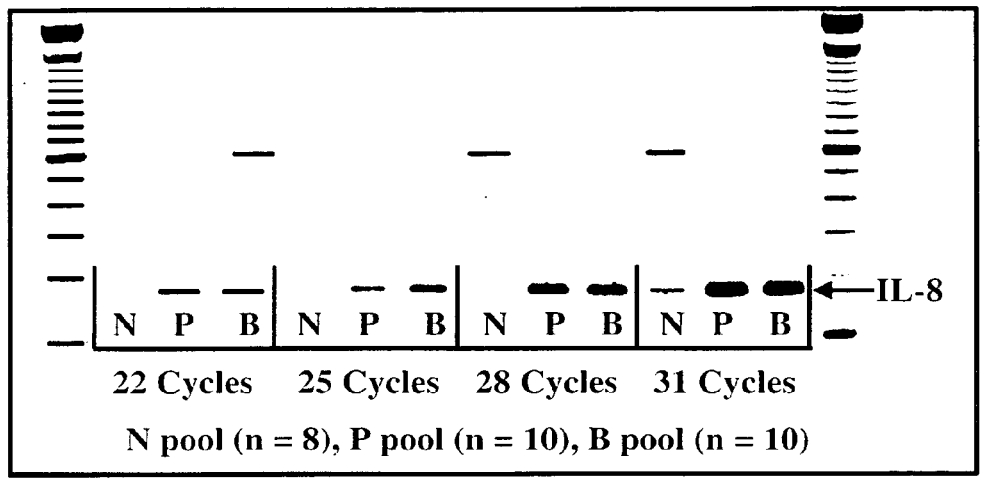

Schmid and Weissmann, "Induction of mRNA for a serine protease and a β-thromboglobulin-like protein in mitogen-stimulated human leukocytes," *J. Immunol.*, 139:250-256, 1987.

Takahashi, Satoru, et al., "Potential Markers of Prostate Cancer Aggressiveness Detected by Fluorescence in Situ Hybridization in Needle Biopsies", *Cancer Research*, 54:3574-3579, 1994.

Babian et al., "Comparative analysis of prostate specific antigen and its indexes in the detection of prostate cancer," *J. Urol.*, 156:432-437, 1996.

Barinaga, "An intriguing new lead on Huntington's disease," *Science*, 271:1233-1234, 1996.

Brawn et al., "Prostatic acid phosphatase levels (enzymatic method) from completely sectioned, clinically benign, whole prostates," *The Prostate*, 28:295-299, 1996.

Carter et al., "Prostate-specific membrane antigen is a hydrolase with substrate and pharmacologic characteristics of a neuropeptidase," *Proc. Natl. Acad. Sci. USA*, 93:749-753, 1996.

Carter et al., "Prospective evaluation of men with stage T1C adenocarcinoma of the prostate," *J. Urol.*, 157:2206-2209, 1997.

Christensson et al., "Serum prostate specific antigen complexed to α1-antichymotrypsin as an indicator of prostate cancer," *J. Urol.*, 150:100-105, 1993.

Cooner et al., "Prostate cancer detection in a clinical urological practice by ultrasonography, digital rectal examination and prostate specific antigen," *J. Urol.*, 143:1146-1154, 1990.

di Celle et al., "Cytokine gene expression in β-cell chronic lymphocytic leukemia: evidence of constitutive interleukin-8 (IL-8) mRNA expression and secretion of biologically active IL-8 protein," *Blood*, 84:220-228, 1994.

Dong et al., "*KAI1*, a metastasis suppressor gene for prostate cancer on human chromosome 11p11.2," *Science*, 268:884-886, 1995.

Harris et al., "Prospective longitudinal evaluation of men with initial prostate specific antigen levels of 4.0 ng./ml. or less," *J. Urol.*, 157:1740-1743, 1997.

Huang et al., "Comparison of prostate secretory protein with prostate specific antigen and prostatic acid phosphatase as a serum biomarker for diagnosis and monitoring patients with prostate carcinoma," *Prostate*, 23:201-212, 1993.

Israeli et al., "Expression of the prostate-specific membrane antigen," *Cancer Res.*, 54:1807-1811, 1994.

Jacobson et al., "Incidence of prostate cancer diagnosis in the eras before and after serum prostate-specific antigen testing," *JAMA*, 274:1445-1449, 1995.

Larsen et al., "The neutrophil-activating protein (NAP-1) is also chemotactic for T lymphocytes," *Science*, 243:1464-1466, 1989.

Liang and Pardee, "Differential display of eukaryotic messenger RNA by means of the polymerase chain reaction," *Science*, 257:967-971, 1992.

Liang et al., "Differential display and cloning of messenger RNAs from human breast cancer versus mammary epithelial cells," *Cancer Res.*, 52:6966-6968, 1992.

Lifton, "Molecular genetics of human blood pressure variation," *Science*, 272:676-680, 1996.

Lilja et al., "Prostate-specific antigen in serum occurs predominantly in complex with $\alpha_1$-antichymotrypsin," *Clin. Chem.*, 37:1618-1625, 1991.

López-Nieto and Nigam, "Selective amplification of protein-coding regions of large sets of genes using statistically designed primer sets," *Nature Biotechnol.*, 14:857-861, 1996.

Marley et al., "Free and complexed prostate-specific antigen serum ratios to predict probability of primary prostate cancer and benign prostatic hyperplasia," *Urology*, 48(6A):16-22, 1996.

McClelland et al., Interactions among regulators of RNA abundance characterized using RNA fingerprinting by arbitrarily primed PCR™, *Nucl. Acids Res.*, 22:4419-4431, 1994.

McCormack et al., "Molecular forms of prostate-specific antigen and the human kallikrein gene family: a new era," *Urology*, 45:729-744, 1995.

Miki et al., "A strong candidate for the breast and ovarian cancer susceptibility gene *BRAC1*," *Science*, 266:66-71, 1994.

Morahan et al., "Markers on distal chromosome 2q linked to insulin-dependent diabetes mellitus," *Science*, 272:1811-1813, 1996.

Murphy et al., "Comparison of prostate specific antigen, prostate specific membrane antigen, and LNCaP-based enzyme-linked immunosorbent assays in prostatic cancer patients and patients with benign prostatic enlargement," *Prostate*, 26:164-168, 1995.

Murphy et al., "Evaluation and comparison of two new prostate carcinoma markers," *Cancer*, 78:809-818, 1996.

Oesterling et al., "Free, complexed and total serum prostate specific antigen: the establishment of appropriate reference ranges for their concentrations and ratios," *J. Urol.*, 154:1090-1095, 1995.

Oesterling, "Molecular PSA: the next frontier in Pca screening," *Contemporary Urol.*, 8:76-92, 1996.

Partin and Oesterling, "The clinical usefulness of prostate specific antigen: update 1994," *J. Urol.*, 152:1358-1368, 1994.

Partin and Oesterling, "The clinical usefulness of percent free-PSA," *Urology*, 48(6A):1-3, 1996.

Partin and Oesterling (Eds.), "The clinical usefulness of percent free prostate-specific antigen," *Urology*, 48(6A)suppl:1-87, 1996.

Pettersson et al., "Free and complexed prostate-specific antigen (PSA): in vitro stability, epitope map, and development of immunofluorometric assays for specific and sensitive detection of free PSA and PSA-$\alpha_1$-antichymotrypsin complex," *Clin. Chem.*, 41(10):1480-1488, 1995.

Piironen et al., "Immunofluorometric assay for sensitive and specific measurement of human prostatic glandular kallikrein (hK2) in serum," *Clin. Chem.*, 42:1034-1041, 1996.

Ralph and Veltri, "Prostate cancer progress," *Advance/Laboratory*, 6:51-56, 1997.

Ralph et al., "RNA fingerprinting using arbitrarily primed PCR™ identifies differentially regulated RNAs in mink lung (My1Lu) cells growth arrested by transforming growth factor β1," *Proc. Natl. Acad. Sci. USA*, 90:10710-10714, 1993.

Sidransky et al., "Identification of p53 gene mutations in bladder cancers and urine samples," *Science*, 252:706-709, 1991.

Silver et al., "Prostate-specific membrane antigen expression in normal and malignant human tissues," *Clin. Cancer Res.*, 3:81-85, 1997.

Slamon et al., "Studies of the HER-2/neu proto-oncogene in human breast and ovarian cancer," *Science*, 244:707-712, 1989.

Soh et al., "Has there been a recent shift in the pathological features and prognosis of patients treated with radical prostatectomy?" *J. Urol.*, 157:2212-2218, 1997.

Stenman et al., "A complex between prostate-specific antigen and α1-antichymotrypsin is the major form of prostate-specific antigen in serum of patients with prostatic cancer: assay of the complex improves clinical sensitivity for cancer," *Cancer Res.*, 51:222-226, 1991.

Taparowsky et al., "Activation of the T24 bladder carcinoma transforming gene is linked to a single amino acid change," *Nature*, 300:762-764, 1982.

Vieira et al., "Isolation and expression of human cytokine synthesis inhibitory factor cDNA clones: homology to Epstein-Barr virus open reading frame BCRFI," *Proc. Natl. Acad. Sci. USA*, 88(4):1172-1176, 1991.

Welsh and McClelland, "Fingerprinting genomes using PCR™ with arbitrary primers," *Nucl. Acids Res.*, 18:7213-7218, 1990.

Welsh et al., "Arbitrarily primed PCR™ fingerprinting of RNA," *Nucl. Acids Res.*, 20:4965-4970, 1992.

Zlotta et al., "Prostate specific antigen density of the transition zone: a new effective parameter for prostate cancer prediction," *J. Urol.*, 157:1315-1321, 1997.

An et al., "Differential expression of full-length and a truncated Her-2/neu oncogene receptor in prostate cancer assessed using relative quantitative RT-PCR," *Molecular Urology*, 2(4):305-310, 1998.

Veltri et al., "Interleukin-8 serum levels in patients with benign prostatic hyperplasia and prostate cancer," *Urology*, 53(1):139-147, 1999.

Veltri et al., "The role of biopsy pathology, quantitative nuclear morphometry, and biomarkers in the preoperative prediction of prostate cancer staging and prognosis," *Seminars in Urologic Oncology*, 16(3):106-117, 1998.

PCT International Search Report, PCT/US99/06488, Aug. 3, 1999.

Adams et al., "Initial assessment of human gene diversity and expression patterns based upon 83 million nucleotides of cDNA sequence," *Nature*, 377(6547 Suppl.):3-174, GenBank Acc. No. AA310306, 1995.

Mukaida et al., "Genomic Structure of the human monocyte-derived neutrophil chemotactic factor IL-8," *Jour. Immun.*, 143(4):1366-1371, Aug. 15, 1989.

Nomura et al., "Prediction of the coding sequences of unidentified human genes: VI. The coding sequences of 80 new genes (KIAA0201-KIAA0280) deduced by analysis of cDNA clones from cell line KG-1 and brain," *DNA Res.*, 3(5):321-329, GenBank Acc. No. D87451, 1996.

Hotta et al., "Coding region structure of interleukin-8 gene of human lung giant cell carcinoma LU65C cells that produce LUCT/interleukin-8:homogeneity in interleukin-8 genes," *Immunology Letters*, 24:165-170, 1990.

Sticherling et al., "Production and characterization of monoclonal antibodies against the novel neutrophil activating peptide NAP/IL8," *Jour. Immun.*, 143(5):1628-1634, Sep. 1, 1989.

Berghella et al., "Prognostic significance of immunological evaluation in colorectal cancer," *Cancer Biotherapy & Radiopharmaceuticals*, 11(6):355-361, 1996.

Brew et al., "Detection of interleukin-8 mRNA and protein in human colorectal carcinoma cells," *European J. Cancer*, 32A(12):2142-2147, 1996.

Edmonds et al., "Elongation factor 1α is an overexpressed actin binding protein in metastatic rat mammary adenocarcinoma," *J. Cell Science*, 109:2705-2714, 1996.

Ferrer et al., "Cytokine regulation of angiogenesis factors in human prostate cancer," *Proceedings of the American Urological Association*, 135:163, 1996.

Greene et al., "Correlation of metastasis-related gene expression with metastatic potential in human prostate carcinoma cels implanted in nude mice using an in situ messenger RNA hybridization technique," American Journal of Pathology, 150(5):1571-1582, 1997.

Gutman et al., "Regulation of interleukin-8 expression in human melanoma cells by the organ environment,".

Heller et al., "Discovery and analysis of inflammatory disease-related genes using cDNA microarrays," *Proc. Natl. Acad. Sci., USA*, 94:2150-2155, 1997.

Isaacs, "Molecular markers for prostate cancer metastasis: developing diagnostic methods for predicting the aggressiveness of prostate cancer," American J. Pathology, 150(5):1511-1521, 1997.

Nagase et al., "Prediction of the coding sequences of unidentified human genes. VI. The coding sequences of 80 new genes (KIAA0201-KIAA0280) deduced by analysis of cDNA clones from cell line KG-1 and brain," *DNA Research*, 3:321-329, 1996.

Pencil et al., "Candidate metastasis-associated genes of the rat 13762NF mammary adenocarcinoma," *Breast Cancer Research and Treatment*, 25:165-174, 1993.

Ueda et al., "Serum levels of cytokines in patients with colorectal cancer: possible involvement of interleukin-6 and interleukin-8 in hematogenous metastasis," *J. Gastroenterol.*, 29:423-429, 1994.

Wellstein et al., "Growth factors as targets in tumor therapy," *International J Pharmacology*, 33:35-47, 1995.

Zhang and Zhang, "Rapid identification of differentially expressed RNA transcripts in apoptotic T lymphocytes," *J. Immunological Methods*, 195:113-123, 1996.

\* cited by examiner

```
                                                                         30                                          60
GCGGCAGGCGCGGCAAATTACGTTGCCCGGAGCTGAACGGCGGCGGCTGGTCTGAAGGCAAA           HUM-UC331
                                                                         90                                         120
CAAGCGAGCGAGCGCGCGATAGGGGCCGAGAGGACGCGCGCAGGTGGCGGCGTTGCCATGTC           HUM-UC331
                                                                                                                 START
                                                                        150                                         180
GCACGGTCACAGCCACGGGGGGTGCCGCTGCCGCCCCGAACGGGAGGAGCCGCC                   HUM-UC331
                                                                        210                                         240
CGAGCAGCGGCCTGGCCTACGGCCTGTACCTGCCGCCATCGACCTGAGCGGCTGCAATG              HUM-UC331
                                                                        270                                         300
CCTTAACGAGAGCCGCGAGGGCAGCCGCGGCGTCTTCAAGCCATGGGAGGAGCGGAC                HUM-UC331
                                                           TTTCAAGCCGTGGGAGGA-CGGAC                                  MOU-UC331
                                                                *       *
                                                                        330                                         360
CGACCCGCTCCAAGTTTATTGAAAGTGATGCAGATGAAGAGCTTCTGTTTAATATATTCCATT          HUM-UC331
CGACCGCTCCAAGTTCGCTGAAAGTGATGCGGACGAAGAGCTCCTGTTTAATATATTCCGTT           MOU-UC331
                  *  *                *                      *    *
                                                                        390                                         420
TACGGGCAATGTCAAGCTCAAAGGCATCATTATAATGGGAGAGGATGATGACTCACACCC             HUM-UC331
TACGTGCAATGTCAAGCTGAAAGGCGTCATCATAATGGGCGAGGATGATGACTCGCACCC             MOU-UC331
      *              *        *       *                *
                                                                        450                                         480
CTCTGAGATGAGACTGTACAAGAATATTCCACAGATGTCCTTTGATGATACAGAAAGGGA             HUM-UC331
CTCGGAGATGAGACTGTACAAGAACATTCCACAGATGTCATTTGATGACAGAAAGGGA               MOU-UC331
   *                       *                   *      *
```

FIG. 6A

```
                                                    540
510
GCCAGAGATCAGACCTTTAGTCTGAACCGGATCTTACAGGAGAATTAGAGTATGCTACAAA HUM-UC331
GCCAGAGCAGAGACCTTCAGTCTGAACCGGAGACATTACAGGAGAATTAGAATATGCTACGAA MOU-UC331
      *                *  **                       *
                                                    600
570
AATTTCTCGTTTTTCAAATGTCTATCATCTCTCAATTCATATTTCAAAAAAACTTCGGAGC HUM-UC331
AATCTCCAGGTTTTCAAATGTCTATCATCTTTCCATTCATATTTCAAAAAACTTTGGAGC MOU-UC331
   *  *                    ** *                    **
                                                    660
630
AGATACGACAAAGGTCTTTTATATTGGCCTGAGAGGAGAGTGGACTGAGCTTCGCCGACA HUM-UC331
AGATACGACGAAGATCTTTTATATTGGCCTGCGGGGAGAGTGGACTGAGCTTCGCCGGCA MOU-UC331
         ** *                   ** *                   *
                                                    720
690
CGAGGTGACCATCTGCAATTACGAAGCATCTGCCAACCCAGCAGACCATAGGGTCCATCA HUM-UC331
TGAGGTGACCATCTGCAACTATGAAGCGTCAGCCAACCCAGCAGACCACCGGGTGCATCA MOU-UC331
*                 *  *     * *                **    * *
                                                    780
750
GGTTACCCCCACAGACACACTTTATTCCTAAGGGCTGGCCAAGGCTCCCATAGAGGCGCT HUM-UC331
GGTCACCCCCGCAGACACACTTCATTTCTTTAAGGGCTCCGGGCCAGCCGGGCTCCCTCAGATGCGCT MOU-UC331
   *      *          *  * *  *        **  **     **       *
                             *STOP
                                                    840
810
GTGTCAGTGAAGATGTACGACTACCTGTGTTGGGAAGGACAAAGGGATGAGGCTCCAGAGAG HUM-UC331
GTTAGTGAA--GATGTGCGACCACCTGCTGGGAAGGACAGAGG-ATG---CTCCAGCAAT MOU-UC331
** ****      *      **    *           *  **      *  ***
```

FIG. 6B

```
                                                          900
AGTTGGCTGCCACAGCTCTG-CCAAGCTTTGTCTTTGGGGCTTGCTGCAGAAACCTGGCC  HUM-UC331
AGTTGCCTGCCAGAGCTTTGGCCAGGCTTTGTC-TCGGGG-TTGCTGCAGGAACCTGGCC  MOU-UC331
 **  ******** ****** **   *  * ** * ****  ****** ** *******

870

960
TACGGAAGATACGACACCACTGGGAGGGTTGTGTAGGTGCCAGGGGACCATCGTGGTTCT  HUM-UC331
TGTGGAAACCGCCTCACCACCAGGAGCG--GTATGGGTGCCAAGGA---TAGTCTCTCT  MOU-UC331
* ****** * **  ***** ** **    ** ******* ***      ** ** **

930

1020
CTAGGGCGCTGTGGAAATTGGGTCTCTTGGGCTGGCATCTGGCAGTCATGGGTAACACAC  HUM-UC331
CTAAGGCACTGCAGAAACTGGGTCTTAGGCTGGGTGGCATCTGTCAGTCATGAATAAATGC  MOU-UC331
*** *** ***  ****  **** ** ** ***** **  *** ** ***      * *

990

1080
TTGCTTTTCCAGTTAATGTGGCCATGTGATTCCAAGTGTCATGTTGCTTTGTGAAGATT  HUM-UC331
TCACTT-CCCAGTC--TGTGGCCACGGGATCCCATGTGTCTTTTGCTT-GATTTCTTGT  MOU-UC331
* * ** ****** * *******        *  *  ***   ***** ** ** *

1050

1140
GTTGTGTGACTTGTTTTTTGATTTTGTATTTGTTTTTTAAAGGAAACTATTTGTGGGC  HUM-UC331
GTGGTTTGTCCT-TTTGTGGCA-----------TCAAAAAAGGATGCTTCCTTGACCG  MOU-UC331
** * * * **  ***  * *          * ***  *** * ***  *

1110

1200
TATAGGAAACTTTCTGATGCCCTCCGGATT-GTGTTAGTAGTAGCCATCAGGAGGGTCTCC  HUM-UC331
TAGAAT---CCTTCTGAAACCCG-AGTTTCGTGTTGTTTTGAATTAGCCATCAGGAGGGTCTCC  MOU-UC331
**  *    ****** * ***  ** *   *** *    * ** ****************

1170

FIG. 6C
```

```
AACTA-AAACACTT-GTTCCTGCTTGCTCCTCCTTTCCCCTCTCATTGTTCAGCATTCTTGTC  HUM-UC331
AGCTAGAAACACTTCGTCCCTGCTTGCTCCT-CCTCCTGTCATTGCTCAGCATTCGTGTC    MOU-UC331
 *        *       *   *   ****  *       * *      *       *

AAGTTGCCCAGCTTGGAGTTGTCTGTCACGCACATGTGTCCTGTGGTTATAGCTAGAAGG    HUM-UC331
AGGGTGCCTAGCT-GGTGTCACATATCAGACACAAGTGTCCCACAATGGTGGTTGGAAAG    MOU-UC331
 *  *    ****  * *   *    *  * *      *       *    *   ** *

ACAGGAGTCTCCTGCTGATGCGTGATAGCTTAAGCTTGGGGAGAAGGTCTTTTCCACTGC    HUM-UC331
GAAGGAGTCTCCTG---ATACATGACTGCTT-----GGGG--AAGG-CTTACACAGT-C    MOU-UC331
  *********** *   **  ***  *  *     ****  ***  **    * *  *

CTAGCTAAGCAGTCTCGGGGAGAGCATGGGGATCATTTCTATGTGTGTGGGTAATCTGGTC  HUM-UC331
TAGCCAAATTAGTT--GCGAG--------TCCTTTCCCTGTGT--GGGTGACCTGGTT     MOU-UC331
 ***  **  ***    * **        ********       **** * ***** *

AG--TAAGATTGAGACTTAGTTAAGATTCCCCCTTGGAAATTCCTTAATGTTATTAGCTT   HUM-UC331
GGGGTAAAACTGAGACAG--TAAAGATTCCTCTTGGGACCTCCTTGGTGTTCCCTGCTT    MOU-UC331
 *   **** *****     ******* *  ****     ****   ***   ** ***

CTAACTAGTGTGTAAGTCCGATGCCAGAATTTGGAGATTTGAGTTCTTCTTTTCATGGC    HUM-UC331
CTAACTAGTCATGTTATAAACCCAGGCTCTGGAGTCTGGAGACCCTGCTCCTTCGTTCATGGC  MOU-UC331
*********    * *   *  **   * ***** ****    **  *  ***  ******
```

FIG. 6D

```
                   1590                                              1620
TTTTATTCACTGTGACTAATAAGCTTCCTAATAAATCCTTGCCAGACTTAAAAAAAAAAAA HUM-UC331
TTTCATTCATGGTGACTAATGAGCTTCCTAATAAATCCTTAG-AGACTTAAAA         MOU-UC331
*    **      *                        *  *
```

FIG. 6E

```
            10          20          30          40
   MSHGHSHGGGGCRCAAER-EEPPEQRGLAYGLYLRIDLE   HUM-UC331
  >CSHGHSHN-----CAAEHIPEVPGDDVYRYDMVSYIDME   ZK353.1

50          60          70          80
   RLQCLNESREGSGRGVFKPWEERTDRSKFIESDADEELLF   HUM-UC331
                 >FKPWEERTDRSKFAESDADEELLF   MOU-UC331
   KVTTLNESVDGAGKKVFKVMEKRDDRLEYVESDCDHELLF   ZK353.1

90         100         110         120
   NIPFTGNVKLKGIIIMGEDDDSHPSEMRLYKNIPQMSFDD   HUM-UC331
   NIPFTCNVKLKGVIIMGEDDDSHPSEMRLYKNIPQMSFDD   MOU-UC331
   NIPFTGHVRLTGLSIIGDEDGSHPAKIRLFKDREAMSFDD   ZK353.1

130         140         150         160
   TEREPDQTFSLNRDLTGELEYATKISRFSNVYHLSIHISK   HUM-UC331
   TEREPEQTFSLNRDITGELEYATKISRFSNVYHLSIHISK   MOU-UC331
   CSIEADQEIDLKQDPQGLVDYPLKASKFGNIHNLSILVDA   ZK353.1

170         180         190         200
   NFGADTTKVFYIGLRGEWTELRRHEVTICNYEASANPADH   HUM-UC331
   NFGADTTKIFYIGLRGEWTELRRHEVTICNYEASANPADH   MOU-UC331
   NFGEDETKIYYIGLRGEFQHEFRQRIAIATYESRAQLKDH   ZK353.1

210
   RVHQVTPQTHFIS.   HUM-UC331
   RVHQVTPQTHFIS.   MOU-UC331
   KNEIPDAVAKGLF.   ZK353.1
```

FIG. 7

```
  1 CGACTCGTCG CCATTCCCGG AGCAGGTCGG CCTCGGCCCA GGGGCGAGTA   50
 51 TCCGTTGCTG TGTCGGAGAC ACTAGTCCCC GACACCGAGA CAGCCAGCCC  100
101 TCTCCCCTGC CTCGCGGCGG GAGAGCGTGT CCGGCCGGCC GGCCGGCGGG  150
151 GCTCGCGCAA CCTCCCCTCG CTCCCCTTCC CCCGCAGCCT CCGCCCCGCC  200
201 AGGCCCCGGG CGGACTCCCG AGCCCCGGCC TCCTCGTCCT CGGTCGCCGC  250
251 TGCCGCCGGG CTTAACAGCC CCGTCCGCCG CTTCTCTTCC TAGTTTGAGA  300
301 AGCCAAGGAA GGAAACAGGG AAAAATGTCG CCATGAAGGC CGAGAACCGC  350
351 TGCCGCCGCC GACCCCCGCC GGCCCTGAAC GCCATGAGCC TGGGTCCCCG  400
401 CCGCGCCCGC TCCGCTCCGA CTGCCGTCGC CGCCGAGGCC CCCGTTGATG  450
451 CCGCTGAGCT CCCCCAACGC CGCCGCCACC GCCTCCGACA TGGACAAGAA  500
501 CAGCGGCTCC AACAGCTCCT CCGCCTCTTC GGGCAGCAGC AAAGGGCAAC  550
551 AGCCGCCCCG CTCCGCCTCG GCGGGGCCAG CCGGCGAGTC TAAACCCAAG  600
```

FIG. 11A

```
        610        620        630        640        650
AGCGAATTAC TAATTTCAGC TGGATTCAAT TTGTTGTCAG TTGATTCTGT
         660        670        680        690        698
AGTAAGGCCA TATGTTGCCC CTCTGGAGGT GCTTGTCAAC TACTCTGG

ATG ATG GAT GGA AAG AAC TCC AGT GGA TCC AAG CGT TAT AAT  740
Met Met Asp Gly Lys Asn Ser Ser Gly Ser Lys Arg Tyr Asn   14

CGC AAA CGT GAA CTT TCC TAC CCC AAA AAT GAA AGT TTT AAC  782
Arg Lys Arg Glu Leu Ser Tyr Pro Lys Asn Glu Ser Phe Asn   28

AAC CAG TCC CGT CGC AGT TCA CAG AAA AGC AAG ACT TTT      824
Asn Gln Ser Arg Arg Ser Ser Gln Lys Ser Lys Thr Phe       42

AAC AAG ATG CCT CCT CAA AGG GGC GGC GGG AGC AAA CTC      866
Asn Lys Met Pro Pro Gln Arg Gly Gly Gly Ser Lys Leu       56

TTT AGC TCT TTT AAT GGT GGA AGA CGA GAT GAG GTA GCA      908
Phe Ser Ser Phe Asn Gly Gly Arg Arg Asp Glu Val Ala       70

GAG GCT CAA CGG GCA GAG TTT AGC CCT GCC CAG TTC TCT GGT  950
Glu Ala Gln Arg Ala Glu Phe Ser Pro Ala Gln Phe Ser Gly   84

CCT AAG AAG ATC AAC CTG AAC CAC TTG TTG AAT TTC ACT TTT  992
Pro Lys Lys Ile Asn Leu Asn His Leu Leu Asn Phe Thr Phe   98
```

FIG. 11B

```
GAA CCC CGT GGC CAG ACG GGT CAC TTT GAA GGC AGT GGA CAT  1034
Glu Pro Arg Gly Gln Thr Gly His Phe Glu Gly Ser Gly His   112

GGT AGC TGG GGA AAG AGG AAC AAG TGG GGA CAT AAG CCT TTT  1076
Gly Ser Trp Gly Lys Arg Asn Lys Trp Gly His Lys Pro Phe   126

AAC AAG GAA CTC TTT TTA CAG GCC AAC TGC CAA TTT GTG GTG  1118
Asn Lys Glu Leu Phe Leu Gln Ala Asn Cys Gln Phe Val Val   140

TCT GAA GAC CAA GAC TAC ACA GCT CAT TTT GCT GAT CCT GAT  1160
Ser Glu Asp Gln Asp Tyr Thr Ala His Phe Ala Asp Pro Asp   154

ACA TTA GTT AAC TGG GAC TTT GTG GAA CAA GTG CGC ATT TGT  1202
Thr Leu Val Asn Trp Asp Phe Val Glu Gln Val Arg Ile Cys   168

AGC CAT GAA GTG CCA TCT TGC CCA ATA TGC CTC TAT CCA CCT  1244
Ser His Glu Val Pro Ser Sys Pro Ile Cys Leu Tyr Pro Pro   182

ACT GCA GCC AAG ATA ACC CGT TGT GGA CAC ATC TTC TGC TGG  1286
Thr Ala Ala Lys Ile Thr Arg Cys Gly His Ile Phe Cys Trp   196

GCA TGC ATC CTG CAC TAT CTT TCA CTG AGT GAG AAG ACG TGG  1328
Ala Cys Ile Leu His Tyr Leu Ser Leu Ser Glu Lys Thr Trp   210
```

*FIG. 11C*

```
AGT AAA TGT TAC CCC ATC TGT TAC AGT TCT GTG CAT AAG AAG GAT  1370
Ser Lys Cys Pro Ile Cys Tyr Ser Ser Val His Lys Lys Asp       224

CTC AAG AGT GTT GTT GCC ACA GAG TCA CAT CAG TAT GTT GTT      1412
Leu Lys Ser Val Val Ala Thr Glu Ser His Gln Tyr Val Val       238

GGT GAT ACC ATT ACG ATG CAG CTG ATG AAG AGG GAG AAA GGG      1454
Gly Asp Thr Ile Thr Met Gln Leu Met Lys Arg Glu Lys Gly       252

GTG TTG GTG GCT TTG CCC AAA TCC AAA TGG ATG AAT GTA GAC      1496
Val Leu Val Ala Leu Pro Lys Ser Lys Trp Met Asn Val Asp       266

CAT CCC ATT CAT CTA GGA GAT GAA CAG CAC AGC CAG TAC TCC      1538
His Pro Ile His Leu Gly Asp Glu Gln His Ser Gln Tyr Ser       280

AAG TTG CTG CTG GCC TCT AAG GAG CAG GTG CTG CAC CGG GTA      1580
Lys Leu Leu Leu Ala Ser Lys Glu Gln Val Leu His Arg Val       294

GTT CTG GAG GAG AAA GTA GCA CTA GAG CAG CAG CTG GCA GAG      1622
Val Leu Glu Glu Lys Val Ala Leu Glu Gln Gln Leu Ala Glu       308

GAG AAG CAC ACT CCC GAG TCC TGC TTT ATT GAG GCA GCT ATC      1664
Glu Lys His Thr Pro Glu Ser Cys Phe Ile Glu Ala Ala Ile       322
```

FIG. 11D

```
CAG GAG CTC AAG ACT CGG GAA GAG GCT CTG TCG GGA TTG GCC  1706
Gln Glu Leu Lys Thr Arg Glu Glu Ala Leu Ser Gly Leu Ala   336

GGA AGC AGA GAG GTC ACT GGT GTT GCT GTG GCT CTG GAA  1748
Gly Ser Arg Arg Glu Val Thr Gly Val Ala Val Ala Leu Glu   350

CAA CTG GTG CTG ATG GCT CCC TTG GCG AAG GAG TCT GTT TTT  1790
Gln Leu Val Leu Met Ala Pro Leu Ala Lys Glu Ser Val Phe   364

CAA CCC AGG AAG GGT GTG CTG GAG TAT CTG TCT GCC TTC GAT  1832
Gln Pro Arg Lys Gly Val Leu Glu Tyr Leu Ser Ala Phe Asp   378

GAA GAA ACC ACG GAA GTT TGT TCT CTG GAC ACT CCT TCT AGA  1874
Glu Glu Thr Thr Glu Val Cys Ser Leu Asp Thr Pro Ser Arg   392

CCT CTT GCT CTC CCT CTG GTA GAA GAG GAA GCA GTG TCT  1916
Pro Leu Ala Leu Pro Leu Val Glu Glu Glu Ala Val Ser   406

GAA CCA GAG CCT GAG GGG TTG CCA GAG GCC TGT GAT GAC TTG  1958
Glu Pro Glu Pro Glu Gly Leu Pro Glu Ala Cys Asp Asp Leu   420

GAG TTA GCA GAT GAC AAT CTT AAA GAG GGG ACC ATT TGC ACT  2000
Glu Leu Ala Asp Asp Asn Leu Lys Glu Gly Thr Ile Cys Thr   434
```

*FIG. 11E*

```
GAG TCC AGC CAG CAG GAA CCC ATC ACC AAG TCA GGC TTC ACA 2042
Glu Ser Ser Gln Gln Glu Pro Ile Thr Lys Ser Gly Phe Thr  448

CGC CTC AGC AGC TCT CCT TGT TAC TAC TTT CAA GCG GAA 2084
Arg Leu Ser Ser Ser Pro Cys Tyr Tyr Phe Gln Ala Glu  462

GAT GGA CAG CAT ATG TTC CTG CAC CCT GTG AAT GTG CGC TGC 2126
Asp Gly Gln His Met Phe Leu His Pro Val Asn Val Arg Cys  476

CTC GTG CGG GAG TAC GGC AGC CTG GAG AGG AGC CCC GAG AAG 2168
Leu Val Arg Glu Tyr Gly Ser Leu Glu Arg Ser Pro Glu Lys  490

ATC TCA GCA ACT GTG GTG GAG ATT GCT GGC TAC TCC ATG TCT 2210
Ile Ser Ala Thr Val Val Glu Ile Ala Gly Tyr Ser Met Ser  504

GAG GAT GTT CGA CAG CGT CAC AGA TAT CTC TCT CAC TTG CCA 2252
Glu Asp Val Arg Gln Arg His Arg Tyr Leu Ser His Leu Pro  518

CTC ACC TGT GAG TTC AGC ATC TGT GAA CTG GCT TTG CAA CCT 2294
Leu Thr Cys Glu Phe Ser Ile Cys Glu Leu Ala Leu Gln Pro  532

CCT GTG GTC TCT AAG GAA ACC CTA GAG ATG TTC TCA GAT GAC 2336
Pro Val Val Ser Lys Glu Thr Leu Glu Met Phe Ser Asp Asp  546
```

*FIG. 11F*

```
ATT GAG AAG AGG AAA CGT CAG CGC CAA AAG AAG GCT CGG GAG  2378
Ile Glu Lys Arg Lys Arg Gln Arg Gln Lys Lys Ala Arg Glu   560

GAA CGC CGC CGA GAG CGC AGG ATT GAG ATA GAG GAG AAC AAG  2420
Glu Arg Arg Arg Glu Arg Arg Ile Glu Ile Glu Glu Asn Lys   574

AAA CAG GGC AAG TAC CCA GAA GTC CAC ATT CCC CTC GAG AAT  2462
Lys Gln Gly Lys Tyr Pro Glu Val His Ile Pro Leu Glu Asn   588

CTA CAG CAG TTT CCT GCC TTC AAT TCT TAT ACC TGC TCC TCT  2504
Leu Gln Gln Phe Pro Ala Phe Asn Ser Tyr Thr Cys Ser Ser   602

GAT TCT GCT TTG GGT CCC ACC AGC ACC GAG GGC CAT GGG GCC  2546
Asp Ser Ala Leu Gly Pro Thr Ser Thr Glu Gly His Gly Ala   616

CTC TCC ATT TCT CCT CTC AGC AGA AGT CCA GGT TCC CAT GCA  2588
Leu Ser Ile Ser Pro Leu Ser Arg Ser Pro Gly Ser His Ala   630

GAC TTT CTG CTG ACC CCT CTG TCA CCC ACT GCC AGT CAG GGC  2630
Asp Phe Leu Leu Thr Pro Leu Ser Pro Thr Ala Ser Gln Gly   644

AGT CCC TCA TTC TGC GTT GGG AGT CTG GAA GAC TCT CCC      2672
Ser Pro Ser Phe Cys Val Gly Ser Leu Glu Asp Ser Pro       658
```

*FIG. 11G*

```
TTC CCT TCC TTT GCC CAG ATG CTG AGG GTT GGA AAA GCA AAA  2714
Phe Pro Ser Phe Ala Gln Met Leu Arg Val Gly Lys Ala Lys   672

GCA GAT GTG TGG CCC AAA ACT GCT CCA AAG AAA GAT GAG AAC  2756
Ala Asp Val Trp Pro Lys Thr Ala Pro Lys Lys Asp Glu Asn   686

AGC TTA GTT CCT CCT GCC CCT GTG GAC AGC GAC GGG GAG AGT  2798
Ser Leu Val Pro Pro Ala Pro Val Asp Ser Asp Gly Glu Ser   700

GAT AAT TCA GAC CGT GTT CCT GTG CCC AGT TTT CAA AAT TCC  2840
Asp Asn Ser Asp Arg Val Pro Val Pro Ser Phe Gln Asn Ser   714

TTC AGC CAA GCT ATT GAA GCA GCC TTC ATG AAA CTG GAC ACA  2882
Phe Ser Gln Ala Ile Glu Ala Ala Phe Met Lys Leu Asp Thr   728

CCA GCT ACT TCA GAT CCC CTC TCT GAA GAG AAA GGA GGA AAG  2924
Pro Ala Thr Ser Asp Pro Leu Ser Glu Glu Lys Gly Gly Lys   742

AAA AGA AAA AAA CAG AAA CAG AAG CTC CTG TTC AGC ACC TCA  2966
Lys Arg Lys Lys Gln Lys Gln Lys Leu Leu Phe Ser Thr Ser   756

GTC GTC CAC ACC AAG TGA CACTACTGG CCCAGGCTAC CTTCTCCATC  3013
Val Val His Thr Lys Stop                                  761
```

FIG. 11H

```
TGGTTTTTGT TTTTGTTTTT TTTTCCCCCA TGCTTTTGTT TGGCTGCTGT 3063
AATTTTAAG  TATTTGAGTT TGAACACATT AGCTCTGGGG GGAGGGGGTT 3113
TCCACAATGT GAGGGGGAAC CAAGAAAATT TTAAATACAG TGTATTTTCC 3163
AGCTTCCTGT CTTTACACCA AAATAAAGTA TTGACACAAG AG         3205
```

FIG. 11I

| | C | C | C H | C C | C C | |
|---|---|---|---|---|---|---|
| CPICLYPPTAAKITR | | | CGHI | FCWACII | HYLSLSEK | TWSKCPIC (UC332) |
| CPICLELIKEPVSTK | | | CDHI | FCKFCML | KLLNQKK | SPSQCPLC (BRCA1) |
| CPICLELLKEPVSAD | | | CNHS | FCRACIT | LNYFSNRNTD | GKGNCPLC (rpt-1) |
| CAFCHSVLHNPHQTG | | | CGHR | FCQQCIR | SLRELNSVPIC | PVC (Traf5) |
| CPICMESFTEE QIRPKLLH | | | CGHT | ICRQCLE | KLIASSI | NGVRCPFC (HT2A) |
| CPRCKTTKYRNPSLKLMVNV | | | CGHT | LCESCVD | LIFVR | GAGNCPEC (MAT1) |
| CPVCLQYFAEPMMLD | | | CGHN | ICCACLA | RCWGTAE | TNVSCPQC (rfp) |
| CVLQGGYFIDATTIIE | | | CLHF | SCKTCIV | RYLE | TSKYCPIC (bmi-1) |
| CAICLDEYEDGDKLRILP | | | CSHAYHCK | CVDP | WL | TKKICPVC (CRZF) |
| CTICMENPIDSVLYM | | | CGHMCMYDCAI | | EQWRGV | GGGCPLC (neu) |

FIG. 12

DIAGNOSIS OF DISEASE STATE USING MRNA PROFILES IN PERIPHERAL LEUKOCYTES

This is a divisional of application Ser. No. 09/046,894 filed Mar. 24, 1998 now U.S. Pat. No. 6,190,857.

This application claims priority under 35 U.S.C. § 119(e) to provisional application Ser. No. 60/041,576, filed on Mar. 24, 1997. This application further claims priority under 35 U.S.C. § 119(a) to PCT application US97/22105, filed Dec. 5, 1997, which in turn claims priority to U.S. provisional application 60/032,619 (filed Dec. 6, 1996), 60/032,701 (filed Dec. 12, 1996) and 60/041,576 (filed Mar. 24, 1997). The entire texts of the above-referenced disclosures are specifically incorporated by reference herein without disclaimer.

1.0 BACKGROUND OF THE INVENTION

1.1. Field of the Invention

The present invention relates generally to the detection and diagnosis of human disease states and methods relating thereto. More particularly, the present invention concerns probes and methods useful in diagnosing, identifying and monitoring the progression of disease states through measurements of gene products in leukocytes of the peripheral circulation.

1.2. Description of the Related Art

Genetic detection of human disease states is a rapidly developing field (Taparowsky et al., 1982; Slamon et al., 1989; Sidransky et al., 1992; Miki et al., 1994; Dong et al., 1995; Morahan et al., 1996; Lifton, 1996; Barinaga, 1996). One advantage presented by this field is that certain disease states may be detected by non-invasive means, e.g. sampling peripheral blood or amniotic fluid. Affected individuals may be diagnosed early in disease progression, allowing more effective patient management with better clinical outcomes.

Some problems exist with this approach. A number of known genetic lesions merely predispose to development of specific disease states. Individuals carrying the genetic lesion may not develop the disease state, while other individuals may develop the disease state without possessing a particular genetic lesion. In human cancers, genetic defects may potentially occur in a large number of known tumor suppresser genes and proto-oncogenes.

The genetic detection of cancer has a long history. One of the earliest genetic lesions shown to predispose to cancer was transforming point mutations in the ras oncogenes (Taparowsky et al., 1982). Transforming ras point mutations may be detected in the stool of individuals with benign and malignant colorectal tumors (Sidransky et al., 1992). However, only 50% of such tumors contained a ras mutation (Sidransky et al., 1992). Similar results have been obtained with amplification of HER-2/neu in breast and ovarian cancer (Slamon et al., 1989), deletion and mutation of p53 in bladder cancer (Sidransky et al., 1991), deletion of DCC in colorectal cancer (Fearon et al., 1990) and mutation of BRCA1 in breast and ovarian cancer (Miki et al., 1994).

None of these genetic lesions are capable of predicting a majority of individuals with cancer and most require direct sampling of a suspected tumor, making screening difficult.

Further, none of the markers described above are capable of distinguishing between metastatic and non-metastatic forms of cancer. In effective management of cancer patients, identification of those individuals whose tumors have already metastasized or are likely to metastasize is critical. Because metastatic cancer kills 560,000 people in the US each year (ACS home page), identification of markers for metastatic cancer, such as metastatic prostate and breast cancer, would be an important advance.

A particular problem in cancer detection and diagnosis occurs with prostate cancer. Prostate cancer was diagnosed in approximately 210,000 men in 1997 and about 39,000 men succumbed to the malignancy (Parker et al., 1996; Wingo et al., 1997). The American Cancer Society expects these numbers to be 189,000 diagnosed and 38,000 deaths in 1998 (American Cancer Society, 1998). Although relatively few prostate tumors progress to clinical significance during the lifetime of the patient, those which are progressive in nature are likely to have metastasized by the time of detection. Survival rates for individuals with metastatic prostate cancer are quite low. Between these extremes are patients with prostate tumors that will metastasize but have not yet done so, for whom surgical prostate removal is curative. Determination of which group a patient falls within is critical in determining optimal treatment and patient survival.

The FDA approval of the serum prostate specific antigen (PSA) test in 1984 has subsequently changed the way prostate disease was managed (Allhoff et al., 1989; Cooner et al., 1990; Jacobson et al., 1995). PSA is widely used as a serum biomarker to detect and monitor therapeutic response in prostate cancer patients. Several modifications in PSA assays (Partin and Oesterling, 1994; Babian et al., 1996; Zlotta et al., 1997) have resulted in earlier diagnoses and improved treatment.

While an effective indicator of prostate cancer when serum levels are relatively high, PSA serum levels are more ambiguous indicators of prostate cancer when only modestly elevated, for example when levels are between 2-10 ng/ml. At these modest elevations, serum PSA may have originated from non-cancerous disease states such as BPH (benign prostatic hyperplasia), prostatitis or physical trauma (McCormack et al., 1995). Although application of the lower 2.0 ng/ml cancer detection cutoff concentration of serum PSA has increased the diagnosis of prostate cancer, especially in younger men with non-palpable early stage tumors (Stage Tlc) (Soh et al., 1997; Carter et al., 1997; Harris et al., 1997), the specificity of the PSA assay for prostate cancer detection at low serum PSA levels remains a problem.

In current clinical practice, the serum PSA assay and digital rectal exam (DRE) is used to indicate which patients should have a prostate biopsy (Lithrup et al., 1994). Histological examination of the biopsied tissue is used to make the diagnosis of prostate cancer. Based upon the American Cancer Society estimate of 189,000 cases of diagnosed prostate cancer in 1998 (American Cancer Society, 1998) and a known cancer detection rate of about 35% (Parker et al., 1996), it is estimated that in 1998 over half a million prostate biopsies will be performed in the United States. Clearly, there would be much benefit derived from a serological test that was sensitive enough to detect small and early stage prostate tumors that also had sufficient specificity to exclude a greater portion of patients with noncancerous or clinically insignificant conditions.

Several investigators have sought to improve upon the specificity of serologic detection of prostate cancer by examining a variety of other biomarkers besides serum PSA concentration (Ralph and Veltri, 1997). One of the most heavily investigated of these other biomarkers is the ratio of free versus total PSA (f/t PSA) in a patient's blood. Most PSA in serum is in a molecular form that is bound to other proteins such as α1-antichymotrypsin (ACT) or α2-macroglobulin (Christensson et al., 1993; Stenman et al., 1991;

Lilja et al., 1991). Free PSA is not bound to other proteins. The ratio of free to total PSA (f/tPSA) is usually significantly higher in patients with BPH compared to those with organ confined prostate cancer (Marley et al., 1996; Oesterling et al., 1995; Pettersson et al., 1995). When an appropriate cutoff is determined for the f/tPSA assay, the f/tPSA assay can help distinguish patients with BPH from those with prostate cancer in cases in which serum PSA levels are only modestly elevated (Marley et al., 1996; Partin and Oesterling, 1996). Unfortunately, while f/tPSA may improve on the detection of prostate cancer, information in the f/tPSA ratio is insufficient to improve the sensitivity and specificity of serologic detection of prostate cancer to desirable levels.

Genetic changes reported to be associated with prostate cancer include: allelic loss (Bova, et al., 1993; Macoska et al., 1994; Carter et al., 1990); DNA hypermethylation (Isaacs et al., 1994); point mutations or deletions of the retinoblastoma (Rb) and p53 genes (Bookstein et al., 1990a; Bookstein et al., 1990b; Isaacs et al., 1991); and aneuploidy and aneusomy of chromosomes detected by fluorescence in situ hybridization (FISH) (Macoska et al., 1994; Visakorpi et al., 1994; Takahashi et al., 1994; Alcaraz et al., 1994).

A recent development in this field was the identification of a prostate metastasis suppressor gene, KAI1 (Dong et al., 1995). Insertion of wild-type KAI1 gene into a rat prostate cancer line caused a significant decrease in metastatic tumor formation (Dong et al., 1995). However, detection of KAI1 mutations is dependent upon direct sampling of mutant prostate cells. Thus, either a primary prostate tumor must be sampled or else sufficient transformed cells must be present in blood, lymph nodes or other tissues to detect the missing or abnormal gene. Further, the presence of a deleted gene may frequently be masked by large numbers of untransformed cells that may be present in a given tissue sample.

The most commonly utilized current tests for prostate cancer are digital rectal examination (DRE) and analysis of serum prostate specific antigen (PSA). Although PSA has been widely used as a clinical marker of prostate cancer since 1988 (Partin & Oesterling, 1994), screening programs utilizing PSA alone or in combination with digital rectal examination have not been successful in improving the survival rate for men with prostate cancer (Partin & Oesterling, 1994). While PSA is specific to prostate tissue, it is produced by normal and benign as well as malignant prostatic epithelium, resulting in a high false-positive rate for prostate cancer detection (Partin & Oesterling, 1994).

Other markers that have been used for prostate cancer detection include prostatic acid phosphatase (PAP) and prostate secreted protein (PSP). PAP is secreted by prostate cells under hormonal control (Brawn et al., 1996). It has less specificity and sensitivity than does PSA. As a result, it is used much less now, although PAP may still have some applications for monitoring metastatic patients that have failed primary treatments. In general, PSP is a more sensitive biomarker than PAP, but is not as sensitive as PSA (Huang et al., 1993). Like PSA, PSP levels are frequently elevated in patients with BPH as well as those with prostate cancer.

Another serum marker associated with prostate disease is prostate specific membrane antigen (PSMA) (Horoszewicz et al., 1987; Carter et al., 1996; Murphy et al., 1996). PSMA is a Type II cell membrane protein and has been identified as Folic Acid Hydrolase (FAH) (Carter et al., 1996). Antibodies against PSMA react with both normal prostate tissue and prostate cancer tissue (Horoszewicz et al., 1987). Murphy et al. (1995) used ELISA to detect serum PSMA in advanced prostate cancer. As a serum test, PSMA levels are a relatively poor indicator of prostate cancer. However, PSMA may have utility in certain circumstances. PSMA is expressed in metastatic prostate tumor capillary beds (Silver et al., 1997) and is reported to be more abundant in the blood of metastatic cancer patients (Murphy et al., 1996). PSMA messenger RNA (mRNA) is down-regulated 8-10 fold in the LNCaP prostate cancer cell line after exposure to 5-α-dihydroxytestosterone (DHT) (Israeli et al., 1994).

A relatively new potential biomarker for prostate cancer is human kallekrein 2 (HK2) (Piironen et al., 1996). HK2 is a member of the kallekrein family that is secreted by the prostate gland. In theory, serum concentrations of HK2 may be of utility in prostate cancer detection or diagnosis, but the usefulness of this marker is still being evaluated.

Interleukin 8 (IL-8) is a potent serum cytokine that is synthesized and secreted by a large variety of cell types, including neutrophils, endothelial cells, T-cells, macrophages, monocytes, and fibroblasts (Saito et al., 1994). Previous reports have found overexpression of IL-8 in some forms of cancer. (di Celle et al., 1994; Ikei et al., 1992; Scheibenbogen et al., 1995; Vinante et al., 1993). RT-PCR analysis was used by di Celle et al. (1994) to demonstrate IL-8 production in B-cell chronic lymphocytic leukemia. Vinante et al. (1993) used Northern blot analysis to show upregulation of IL-8 expression in acute myelogenous leukemia. Ikei et al. (1992) found an increase in serum levels of IL-8 in hepatic cancer patients following therapeutic treatment. Scheibenbogen et al. (1995) observed a correlation between IL-8 levels and tumor loads in patients with metastatic melanoma, while reporting that serum IL-8 was undetectable in healthy individuals or in patients with metastatic renal cell carcinoma. These authors suggested that the IL-8 was produced by the melanoma cells themselves, rather than by circulating leukocytes. Andrawis et al. (1996) reported that while IL-8 was expressed in prostate and bladder cancer, it was also abundantly expressed in normal bladder epithelium and in some basal cells in BPH.

The sequence of the IL-10 gene was reported in Vieira et al. (1991). A recent summary of IL-10 gene products in cancer is contained in Holland et al. (1993). The instant application is the first report of an upregulation of IL-10 in circulating leukocytes of patients with metastatic cancers of the prostate or breast.

The instant disclosure is the first to combine measurement of IL-8 gene products with serum markers of prostate disease, such as PSA, PAP, HK2 or PSMA. The surprising result of this multivariate detection is a dramatic increase in sensitivity and specificity of prostate cancer detection, while simultaneously allowing the differentiation of advanced from localized forms of prostate tumor.

2.0 SUMMARY OF THE INVENTION

Existing technologies for the early detection of cancer rely upon the analysis of markers produced by the cancer cells themselves. Some markers, such as PSA, are protein products produced by the transformed cell and released into the bloodstream. Other markers, like ras or BRCA1 involve genetic mutations in cancer cell chromosomal DNA. These methodologies suffer from a variety of defects—lack of specificity or sensitivity, association of the marker with disease states besides cancer, or difficulty of detection in asymptomatic individuals.

The present invention represents a significant advance over existing technologies for cancer detection and diagnosis, in that it relies upon detecting a response of circulating leukocytes to the disease state, rather than detecting direct products of the diseased cells themselves. As such, these methods are suitable for widespread screening of asymptomatic individuals who exhibit one or more risk factors for development of a given form of cancer. In addition, since the markers are produced by circulating leukocytes rather than the diseased cells, it is expected that detection may be feasible at very early stages of disease progression, when there are few or no circulating diseased cells present in the peripheral blood. This represents a significant and unexpected advance in the detection, diagnosis and management of disease states such as human cancer.

The instant invention addresses the problem of diagnosing human disease states by detecting a secondary response to a given disease state that may be measured in peripheral blood samples. A preferred embodiment involves monitoring gene expression in peripheral leukocytes of the immune system. A number of disease states are capable of producing an immune system response, such as asthma, lupus erythromatosis, rheumatoid arthritis, multiple sclerosis, myasthenia gravis, autoimmune thyroiditis, ALS (Lou Gehrig's disease), interstitial cystitis and prostatitis. The methods disclosed herein may be suitable for detection of these diseases, as well as cancers from a variety of tissue sources.

The detection of an immune response, secondary to the above-mentioned disease states, may be reflected in changing patterns of leukocyte mRNA levels that correlate with the presence of the disease state. Alternative means of detection of the immune response may be addressed towards changing patterns of leukocyte protein production that correlate with the presence of the disease state.

The present disclosure provides methods for identifying nucleic acid species and their corresponding protein products that are differentially expressed in peripheral leukocytes of patients with a particular disease state, such as metastatic prostate and breast cancer, compared with normal or healthy individuals. The skilled practitioner will realize that a variety of techniques are known in the art for detection of differentially expressed gene products, such as differential display or other methods of RNA fingerprinting.

An important advantage provided by the present invention is that a disease state may be detected, diagnosed, prognosed and/or monitored for progression, status and response to therapies by examining the response of normal circulating host cells to the disease state. Thus, according to the instant invention, there is no need to directly sample tumor cells in order to detect cancer markers. Such markers may instead be detected by sampling circulating cells of the immune system, circumventing the problem of having to first identify the location of a tumor within the body before being able to analyze it for markers of disease progression.

The instant disclosure demonstrates the success of this approach for the detection of metastatic prostate and/or metastatic breast cancer. Most significantly, it reports that disease states may be detected and monitored by surveying the response of circulating lymphatic cells to the disease condition.

A particularly striking and unexpected result of the instant disclosure concerns the ability to detect and discriminate between benign prostatic hyperplasia (BPH) and prostate cancer, using multivariate analysis with several different prostate disease markers. By combining test results for serum prostate specific antigen (PSA) and IL-8 gene products, it is possible to identify patients with organ-confined prostate cancer and to differentiate these patients from those with benign prostatic hyperplasia with a high sensitivity and specificity. These levels of sensitivity and specificity represent significant advances over the prior art in prostate cancer detection and differentiation, which traditionally have been performed with univariate analysis with PSA, digital rectal examination and other techniques. It is further disclosed that levels of IL-8 gene product in the peripheral circulation may be used to discriminate advanced from localized stages of prostate cancer. Additionally, the IL-10 gene appears to be upregulated in peripheral leukocytes of patients with metastatic breast or prostate cancer. Analysis of IL-10 gene products in peripheral leukocytes may be used in addition to or in place of the IL-8 analysis to detect and diagnose malignant cancers within the scope of the instant invention.

Another important aspect of the instant invention concerns the disease state markers themselves that have been identified by the above-mentioned methods. A number of markers for metastatic cancer of prostate or breast are described in the instant disclosure. Two of the metastatic cancer-markers disclosed herein represent previously unreported genes, with one of the two (UCPB Band #35, SEQ ID NO:48) matching a small expressed sequence tag (EST) described in Genebank Accession # T03013. The other previously unreported gene (UC Band #321, SEQ ID NO:49) has not been found to match any Genebank sequences. Another marker corresponds to the sequence of elongation factor 1-alpha (Genbank Accession # X03558). Two other markers represent alternatively spliced forms (Genbank Accession # M28130 and # Y00787) of mRNA from the IL-8 (interleukin 8) gene. One metastatic cancer marker (UC331) is a previously uncharacterized gene that has homology to a number of previously identified EST sequences, while another marker (UC332) is a previously identified gene sequence (KA000262, Genbank Accession # D87451). Another marker consists of products of the IL-10 gene (Genbank Accession #M57627). In the examples disclosed herein, the differential expression of marker genes is detected by RNA fingerprinting methods, however, differential expression detected by any other means, including other RNA fingerprinting methods known in the art would fall within the scope of the present invention.

Once such a disease state marker is identified, various detection modalities are available for screening and diagnostic purposes. The mRNA species themselves may be detected, for example, by Northern blotting, RT-PCR, slot-blotting, and similar methods well known in the art. Alternatively, the protein products expressed from the mRNAs may be assayed by solid phase immunoassay with microtiter plates, Western blotting, 2-dimensional SDS-polyacrylamide gel electrophoresis, ELISA, and other methods known in the art for detection of specific proteins. The skilled artisan will recognize that the instant invention encompasses all such well-known techniques for detection of the cancer markers disclosed herein.

The present disclosure is the first report of an alternatively spliced form of IL-8 mRNA that includes intron 3. In the peripheral blood of normal individuals the mRNA transcript containing intron 3 (Genbank Accession # M28130) is more abundant than the previously reported spliced form from which intron 3 is missing (Genbank Accession # Y00787).

The substantial change in levels of alternatively spliced mRNA species in the peripheral blood of individuals with metastatic cancer provides a simple and effective diagnostic test for the presence of cancer metastases, that is unaffected by problems in sampling primary tumors or the masking influence of normal cells in a tissue sample. It therefore represents a significant advance over previous methods for detecting and diagnosing metastatic cancer in humans. The skilled practitioner will realize that metastatic cancer detection and diagnosis may be performed by quantitative analysis of either the IL-8 mRNA transcripts themselves or their protein products. The skilled practitioner will further realize that metastatic cancer detection and diagnosis may be performed by quantitative analysis of either the IL-10 mRNA transcripts themselves or their protein products.

The present disclosure represents a substantial and unexpected advance over previous knowledge in this field. It provides a sensitive means for detecting metastatic cancer by measuring the levels of the two alternatively spliced IL-8 mRNA forms. It provides a highly sensitive and specific method for detecting and differentiating between BPH, localized and advanced forms of prostate cancer by combining detection of IL-8 or IL-10 gene product with other markers of prostate disease. It provides an antibody based test for IL-8 or IL-10 protein in circulating leukocytes that shows high levels of both sensitivity and specificity for detection of asymptomatic prostate cancer. When used in combination with analysis of f/t PSA ratio, the assay is ninety percent specific for detection of stage A, B and C prostate cancers compared with BPH.

In one embodiment of the present invention, the isolated nucleic acids of the identified marker genes are incorporated into expression vectors and expressed as the encoded proteins or peptides. Isolated nucleic acid segments may be from published sequences identified or the sequences disclosed herein as marker genes. Coding sequences may be assembled from amino acid encoding segments of marker genes to remove noncoding segments, or to truncate coding sequence, or to use the coding sequences or segments thereof in expression vectors as is known in the art. In certain embodiments, genomic sequences may be used to express peptides or proteins of the metastatic cancer maker genes identified herein.

Such proteins or peptides are in turn used as antigens for induction of monoclonal or polyclonal antibody production. Such antibodies may in turn be used to detect expressed proteins as additional markers for human disease states. Antibody-protein binding may be detected and quantitated by a variety of means known in the art, such as labeling with fluorescent or radioactive ligands.

Certain metastatic marker genes disclosed herein (SEQ ID NO:48 and Genebank accession # T03013; and SEQ ID NO:49) do not have reading frames for translation disclosed. However, one of ordinary skill in the art may translate the identified sequences or segments thereof in the three potential reading frames to obtain peptides or proteins for use in generating antibodies to these marker genes. Such antibodies may be used to purify the proteins of the marker genes, and the identity of protein being detected confirmed by peptide sequencing. Once confirmed as binding the translation products of the marker genes corresponding to SEQ ID NO:48 and Genebank accession # T03013, and SEQ ID NO:49, the antibodies that bind the marker gene protein would be preferred in detecting, diagnosis, or prognosis of metastatic cancer.

In certain aspects of the present invention the terms "immunodetection", "immunobinding", "immunoreaction", "immunohistochemical", "immunosorbent", and "radioimmunoassays" refers to methods that concern binding, purifying, removing, quantifying or otherwise generally detecting biological components by obtaining a sample suspected of containing a protein, peptide or antibody, and contacting the sample with an antibody or protein or peptide in accordance with the present invention, as the case may be, under conditions effective to allow the formation of immunocomplexes. In certain preferred aspects of the present invention, one obtains a sample suspected of containing a disease state-marker encoded protein, peptide or a corresponding antibody, and contacts the sample with an antibody or encoded protein or peptide, as the case may be, and then detects or quantifies the amount of immune complex formed under the specific conditions. The steps of various useful immunodetection methods have been described in the scientific literature, such as, e.g., Nakamura et al. (1987).

In another embodiment of the present invention, the aforementioned oligonucleotide hybridization probes and primers are specific for disease state markers comprising isolated nucleic acids of a sequence comprising the sequences published in Genbank Accession numbers D87451, T03013, X03558, M28130, Y00787, M57627 and D87451, as well as the sequences disclosed herein as SEQ ID NO:1, SEQ ID NO:2, SEQ ID NO:3, SEQ ID NO:29, SEQ ID NO:30, SEQ ID NO:34, SEQ ID NO:48 and SEQ ID NO:49.

Such primers may be used to amplify disease state markers present in a biological sample, such as peripheral human blood. Amplification increases the sensitivity of various known techniques for detecting the presence of nucleic acid markers for human disease. Probes that hybridize with nucleic acid markers for human disease may be detected by conventional labeling methods, such as binding of fluorescent or radioactive ligands. The availability of probes and primers specific for such unique markers provides the basis for diagnostic kits identifying disease state progression.

An embodiment of the present invention encompasses a kit for detecting a disease state in a biological sample, comprising pairs of primers for amplifying nucleic acids corresponding to the marker genes and containers for each of these primers. In another embodiment, the invention encompasses a kit for detecting a disease state in a biological sample, comprising oligonucleotide probes that bind with high affinity to markers of the disease state and containers for each of these probes. In a further embodiment, the invention encompasses a kit for detecting a disease state in a biological sample, comprising antibodies specific for proteins encoded by the nucleic acid markers of the disease state identified in the present invention.

In one broad aspect, the present invention comprises an isolated nucleic acid of a sequence comprising SEQ ID NO:1, SEQ ID NO:2, SEQ ID NO:3, SEQ ID NO:29, SEQ ID NO:30, SEQ ID NO:34, SEQ ID NO:48 or SEQ ID NO:49. The invention further broadly comprises an isolated nucleic acid of between 17 and 100 bases in length, either identical to or complementary with portions of the above mentioned isolated nucleic acids. Such isolated nucleic acids may themselves be used as probes for human disease markers, or may be used to design probes and primers specific for disease state markers.

In another broad aspect, the present invention comprises proteins and peptides with amino acid sequences encoded by the aforementioned isolated nucleic acids, as well as the IL-10 gene. The proteins and peptides may be used for antibody production.

The invention also broadly comprises methods for identifying biomarkers for use in prognostic or diagnostic assays of a disease state, using the technique of RNA fingerprinting to identify RNAs that are differentially expressed between individuals with the disease state versus normal individuals. In the practice of the method, one may use random hexamers, arbitrarily chosen oligonucleotides, promiscuous oligonucleotide primers or anchoring primers, as well as oligonucleotide primers specific for known gene sequences for the reverse transcription step and/or for the amplification step.

The term "promiscuous oligonucleotide primers" as used herein denotes oligonucleotides that are statistically designed to sample sequence complexity in mRNAs, or open reading frames of mRNAs without bias as applied in a PCR based RNA fingerprinting technique. The use of promiscuous primers is preferred because such use increases the sampling rate of RNA for fingerprinting by increasing the displayed fingerprint complexity. This increases the rate at which differentially expressed mRNAs can be discovered. The use of promiscuous oligonucleotide primers as disclosed herein will be evident to one of skill in the art in light of the publication by Lopez-Nieto and Nigam, *Nature Biotechnology* 14:857-861, 1996, incorporated in pertinent part herein by reference).

In certain embodiments the terms "random hexamers" or "small random oligonucleotides" refer to primers of random or semi-random nucleotide sequence of about 6 bases in length, though in certain embodiments the length of the primers may be of any length previously described for "primers". In certain aspects of the invention "arbitrarily chosen oligonucleotides" may refer to primers that are selected at the discretion of one skilled in the art, and may be of random or nonrandom sequence. In certain other embodiments "arbitrarily chosen oligonucleotides" may refer to primers as described by Welsh et al., 1992, incorporated herein by reference. Oligonucleotide sequences designed to bind to specific genes, IL-8 or PSA for example, may also be used in the practice of this method.

The present invention may be described in a broad aspect as a method for identifying serological markers for a human disease state. The method comprises the steps of providing human peripheral blood mRNAs; amplifying the mRNAs to provide nucleic acid amplification products; separating the nucleic acid amplification products; and identifying those mRNAs that are differentially expressed between normal individuals and individuals exhibiting a disease state.

The described method may also comprise, in certain embodiments, the step of converting the RNAs into cDNAs using reverse transcriptase to detect and quantitate mRNAs that are induced by the disease state in circulating cells. In certain embodiments of the invention conversion of RNA into cDNAs using reverse transcriptase is referred to as a "reverse transcriptase" reaction. Methods of reverse transcribing RNA into cDNA are well known and described in Sambrook et al., 1989. Alternative methods for reverse transcription utilize thermostable, RNA-dependent DNA polymerases. These methods are described in WO 90/07641, filed Dec. 21, 1990, incorporated herein by reference. In certain other embodiments of the invention a "reverse transcriptase" reaction refers to additional steps of amplification of the RNA template or its cDNA product. Such step of amplification may include any methods known in the art of increasing the number of copies of RNA or DNA, as well as the methods described herein. Preferred methods of amplification include the methods described in Davey et al., EPO No. 329 822 (incorporated herein by reference in its entirely), as well as polymerase chain reaction or ligase chain reaction The method described in the previous paragraph may be used to discover disease markers for any disease state that affects the peripheral blood leukocytes. Such diseases include, but are not limited to metastatic or organ defined cancer, particularly metastatic prostate cancer, asthma, lupus erythromatosis, rheumatoid arthritis, multiple sclerosis, myasthenia gravis, autoimmune thyroiditis, ALS (Lou Gehrig's disease), interstitial cystitis or prostatitis.

The invention further broadly comprises methods for detecting a disease state in biological samples, using nucleic acid amplification techniques with primers and hybridization probes selected to bind specifically to an isolated nucleic acid of a sequence comprising SEQ ID NO:1, SEQ ID NO:2, SEQ ID NO:3, SEQ ID NO:29, SEQ ID NO:34, SEQ ID NO:48, SEQ ID NO:49 or nucleic acid products of the IL-10 gene, thereby measuring the amounts of nucleic acid amplification products formed.

The invention further broadly comprises the prognosis and/or diagnosis of a disease state by measuring the amounts of nucleic acid amplification products formed. The amounts of nucleic amplification products identified in an individual patient may be compared with groups of normal individuals or individuals with an identified disease state. Diagnosis may be accomplished by finding that the patient's levels of disease state markers fall within the normal range, or within the range observed in individuals with the disease state. Further comparison with groups of individuals of varying disease state progression, such as metastatic vs. non-metastatic cancer, may provide a prognosis for the individual patient. The invention further broadly comprises kits for performing the above-mentioned procedures, containing amplification primers and/or hybridization probes.

The invention may be described therefore, in certain broad aspects as a method of detecting a human disease state, comprising the steps of detecting the quantity of a disease marker expressed in human peripheral blood and comparing the quantity of the said marker to the quantity expressed in peripheral blood of a normal individual, where a difference in quantity of expression is indicative of a disease state. In the practice of the method the disease marker may preferably be an mRNA, or even an mRNA amplified by an RNA polymerase reaction, for example. The mRNA may also be amplified by any other means such as reverse transcriptase polymerase chain reaction or the ligase chain reaction. The RNA may be detected by any means known in the art, such as by RNA fingerprinting, branched DNA or a nuclease protection assay, for example. Disease states that may be detected by the present method include any disease state for which a marker is known and may include metastatic cancer, particularly metastatic prostate cancer, asthma, lupus erythromatosis, rheumatoid arthritis, multiple sclerosis, myasthenia gravis, autoimmune thyroiditis, ALS (Lou Gehrig's disease), interstitial cystitis or prostatitis.

In certain preferred embodiments of this method, the mRNA will comprise one or more of the sequences or the complements of the sequences disclosed herein as SEQ ID NO:1, SEQ ID NO:2, SEQ ID NO:3, SEQ ID NO:29, SEQ ID NO:34, SEQ ID NO:48, SEQ ID NO:49 or the mRNA may comprise a product of the interleukin 8 (IL-8) or interleukin 10 (IL-10) genes.

The method of detecting a disease state described in the previous paragraphs may further comprise the steps of providing primers that selectively amplify the disease state marker, amplifying the nucleic acid with said primers to form nucleic acid amplification products, detecting the nucleic acid amplification products and measuring the amount of the nucleic acid amplification products formed. In the practice of certain embodiments of the method, the primers may be selected to specifically amplify a nucleic acid having a sequence comprising SEQ ID NO:1, SEQ ID NO:2, SEQ ID NO:3, SEQ ID NO:29, SEQ ID NO:34, SEQ ID NO:48, SEQ ID NO:49 or a nucleic acid product of the IL-10 gene. In certain alternate embodiments, the marker may be a polypeptide, and may even be a polypeptide encoded by a nucleic acid sequence comprising a sequence disclosed herein as SEQ ID NO:1, SEQ ID NO:2, SEQ ID NO:3, SEQ ID NO:29, SEQ ID NO:34, SEQ ID NO:48 or SEQ ID NO:49, or it may be described in certain embodiments as a polypeptide encoded by the IL-8 or IL-10 genes. Detection of the disease state may be by detection of an antibody immunoreactive with said marker. It is also an embodiment of the invention that detection may be by a cellular bioassay, that responds to the presence of a biologically active agent such as IL-8 or IL-10, for example.

The present invention broadly comprises production of antibodies specific for proteins or peptides encoded by SEQ ID NO:1, SEQ ID NO:2, SEQ ID NO:3, SEQ ID NO:29, SEQ ID NO:34, SEQ ID NO:48, SEQ ID NO:49 or IL-10 and the use of those antibodies for diagnostic applications in detecting and diagnosing the disease state. The levels of such proteins present in the peripheral blood of a patient may be quantitated by conventional methods. Correlation of protein levels with the presence of a human disease or the progression of a human disease may be accomplished as described above for nucleic acid markers of human disease.

Another broad aspect of the present invention comprises the detection and diagnosis of disease states, including BPH and prostate cancer, by combining measurement of levels of two or more disease state markers. A broad embodiment of the invention comprises combining measurement of serum IL-8 or IL-10 gene products with other markers of prostate disease, such as PSA, PAP, HK2, $PSP_{94}$ and PSMA. Yet another broad aspect of the present invention comprises kits for detection and measurement of the levels of two or more disease state markers in biological samples. The skilled practitioner will realize that such kits may incorporate a variety of methodologies for detection and measurement of disease state markers, including but not limited to oligonucleotide probes, primers for nucleic acid amplification, antibodies which bind specifically to protein products of disease state marker genes, and other proteins or peptides which bind specifically to disease state marker gene products.

Another broad aspect of the invention comprises a method for treating a subject with cancer. One aspect of this method comprises the step of providing an antisense expression construct containing a nucleic acid encoding an RNA species that is capable of binding under high stringency conditions to an mRNA product of the genes encoding SEQ ID NO:1, SEQ ID NO:2, SEQ ID NO:3, SEQ ID NO:29, SEQ ID NO:34, SEQ ID NO:48, SEQ ID NO:49 or the IL-8 or IL-10 genes, under the transcriptional control of a promoter functional in eukaryotic cells. It further comprises the step of contacting the expression construct with peripheral leukocyte cells of the subject in a manner that allows the uptake of the expression construct by the cells, wherein expression of the RNA species results in the treatment of the cancer. By "treatment," the present invention refers to any event that decreases the growth, kills or otherwise abrogates the presence of cancer cells in a subject. Such a treatment may occur by modification of the immune response of the peripheral leukocytes to the cancer, so as to achieve a therapeutic outcome. The skilled practitioner will realize that antisense therapy can constitute the use of any nucleic acid or chemically modified nucleic acid to inhibit translation from a specific mRNA species by annealing to the mRNA and blocking translation and/or promoting degradation of the targeted mRNA and that all such methods are included within the scope of the instant invention.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Relative quantitative RT-PCR for IL-8 on pools of cDNA from healthy controls (N), patients with metastatic prostate cancer (P), and patients with metastatic breast cancer (B).

Figure 1B:
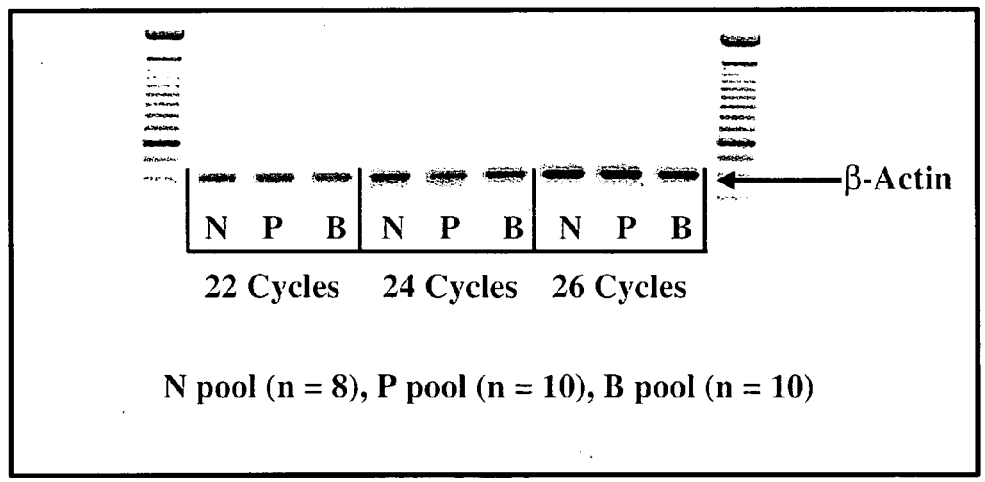

FIG. 1B. β-Actin normalization of pools of cDNAs from the peripheral blood of healthy controls (N), patients with metastatic prostate cancer (P), or metastatic breast cancer (B).

Figure 2A:
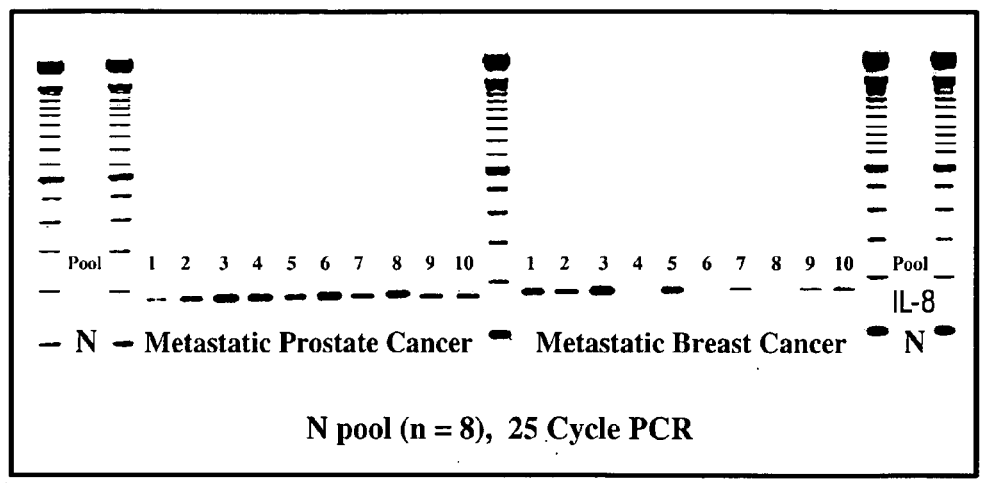

FIG. 2A. Relative quantitative RT-PCR for IL-8 on the peripheral blood of a pool of healthy controls (N) and individuals with either metastatic prostate cancer or metastatic breast cancer.

Figure 2B:
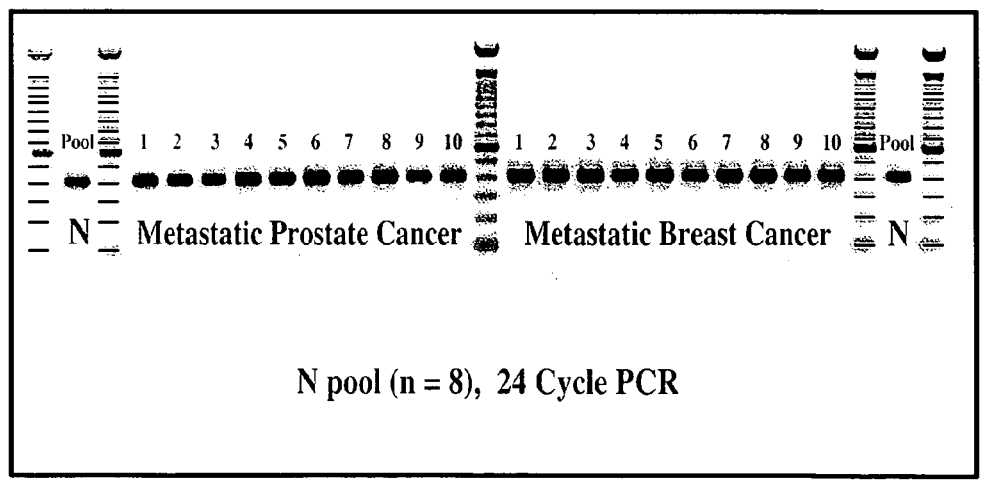

FIG. 2B. β-Actin normalization of cDNAs from the peripheral blood of a pool of healthy controls (N) and individuals with either metastatic prostate cancer or metastatic breast cancer.

Figure 3:
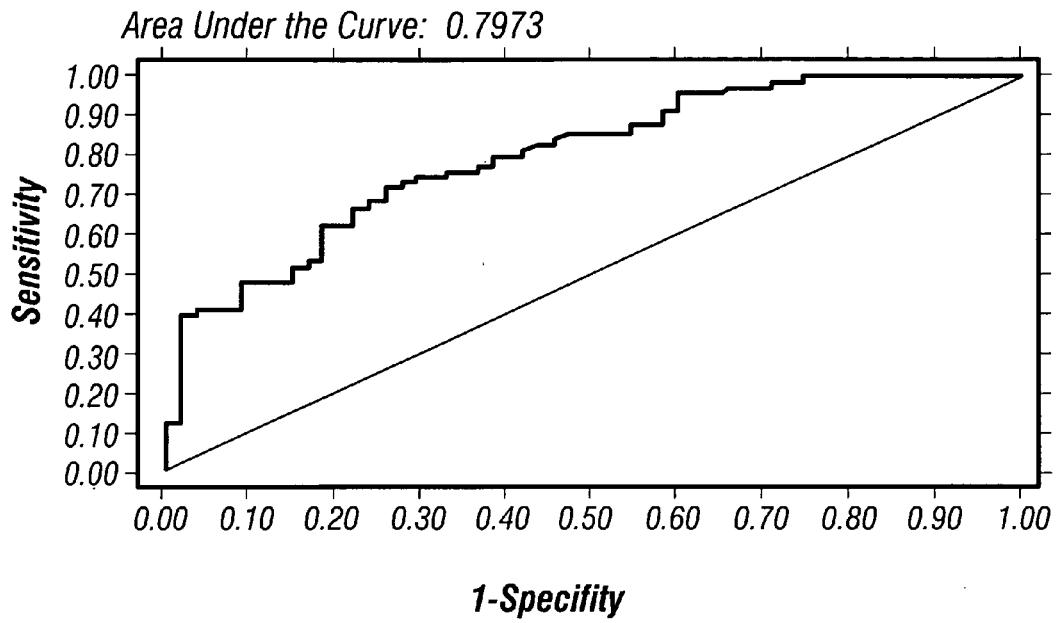

FIG. 3. Ability of IL-8 (pg/ml) to distinguish BPH and Stages A, B, and C prostate cancer (n=142).

Figure 4:
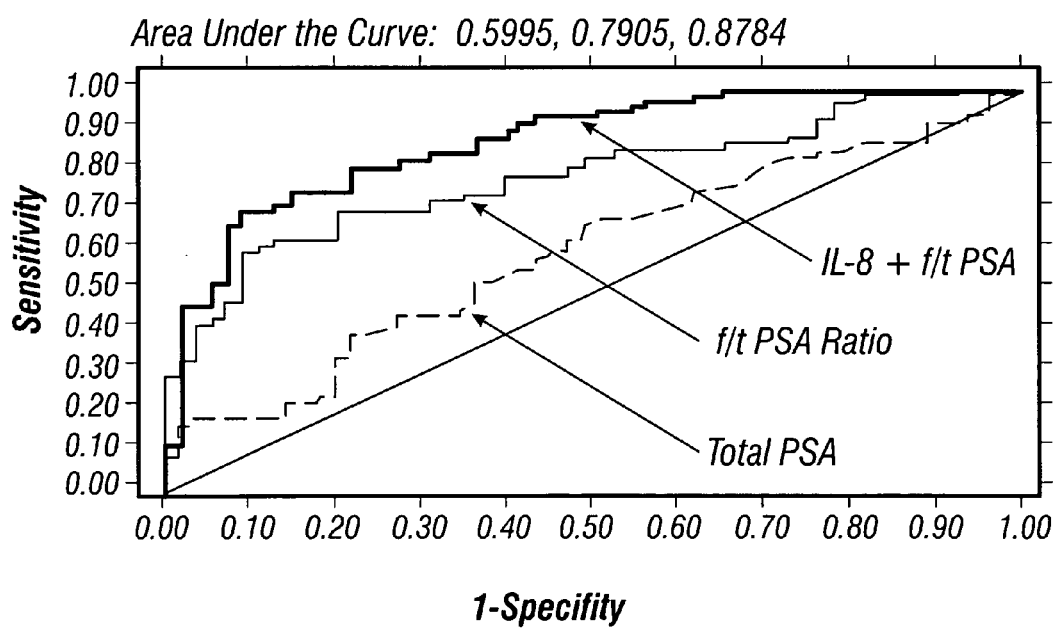

FIG. 4. Ability of total PSA (ng/ml), f/t PSA ratio, and IL-8 (pg/ml)+f/t PSA ratio to distinguish BPH and stages A, B, and C prostate cancer (n=142)

Figure 5:
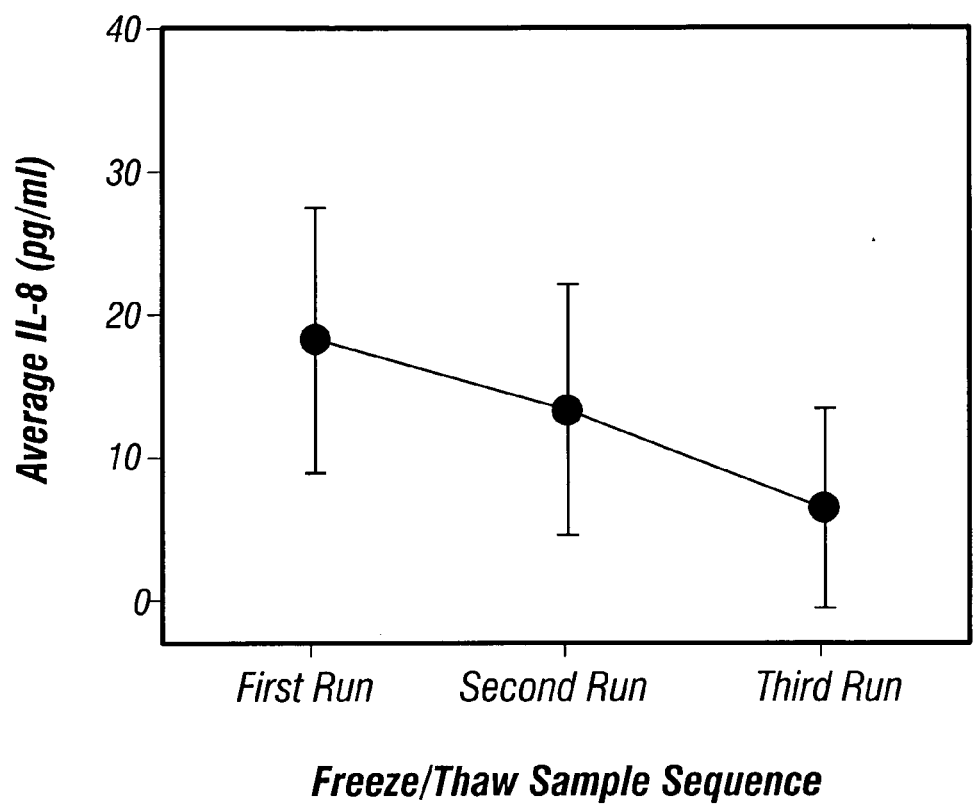

FIG. 5. Effect of freeze/thaw on IL-8 results (n=12).

FIG. 6A, FIG. 6B, FIG. 6C, FIG. 6D, and FIG. 6E. Comparison of the nucleic acid sequence of the human and mouse UC331 cDNA contigs (SEQ ID NO:29 and SEQ ID NO:30, respectively). The human and mouse UC331 sequences were assembled as virtual contigs from the EST data bases available on GenBank as described in Tables 12 and 13. Both sequences predict the presence of a protein encoding open reading frame (ORF) at their 5' ends. The ATG (start codon) in the human sequence is underlined. In the region of their ORFs, both ending at the TAA STOP codon, the sequences of the predicted human and mouse UC331 mRNAs are collinear and more similar (89.8% identical) to each other than they are in the remainder of the contigs (76.1% identical) which is predicted to be 3' untranslated domain. Positions of mismatch are indicated by (*).

FIG. 7. Comparison of the predicted amino acid sequences for the human and mouse UC331 proteins (SEQ ID NO:31 and SEQ ID NO:32, respectively) and the predicted amino acid sequence of the C-terminal end of the putative C. elegans protein ZK353.1 (SEQ ID NO:33). Over the 155 amino acids for which a comparison is possible the mouse and human sequences are 96% identical with all but one of the substitutions being conservative changes. Over the entire 211 amino acids of the mammalian UC331 sequence, the ZK353.1 amino acid sequence is identical to the human or mouse sequence at 94 (45%) positions with many of the differences representing conservative substitutions.

Figure 8A:
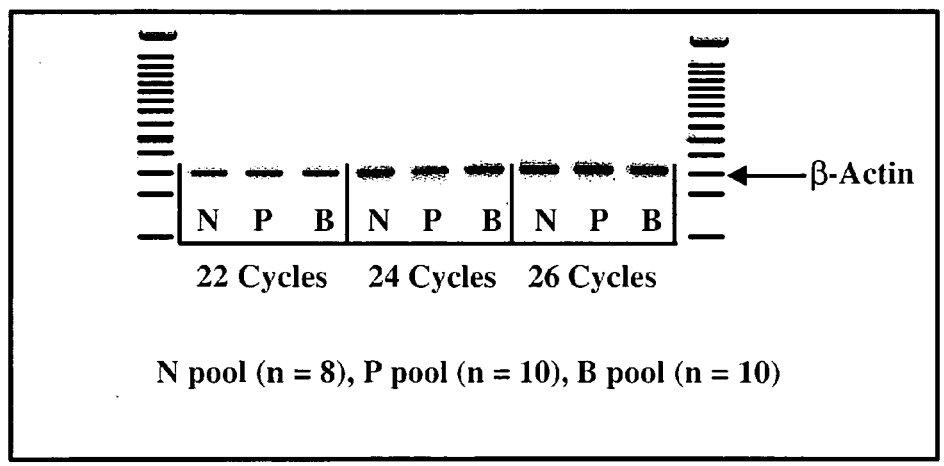

FIG. 8A. Relative quantitative RT-PCR™ showing near equal amounts of amplifiable β-actin cDNA in three pools of cDNA. Three separate PCR™ reactions were performed on each pool of cDNA. PCR™ was terminated at differing cycle numbers and the products were visualized by electrophoresis and ethidium bromide staining. Images were captured and quantitated using a digital image analysis system. Examination of replicate PCR™ reactions at different PCR™ cycle numbers verifies that the observations are being made in the log linear range of the amplification curves. Similar band intensities indicate similar relative concentrations of β-actin mRNA in the RNAs from individuals from which these cDNA pools were constructed. PCR™ reactions were terminated after either 22, 24 or 26 cycles. Pools of normalized cDNAs were constructed from peripheral blood RNAs from eight healthy volunteers (N), ten individuals with recurrent metastatic prostate cancer (P), or ten individuals with recurrent metastatic breast cancer (B).

Figure 8B:
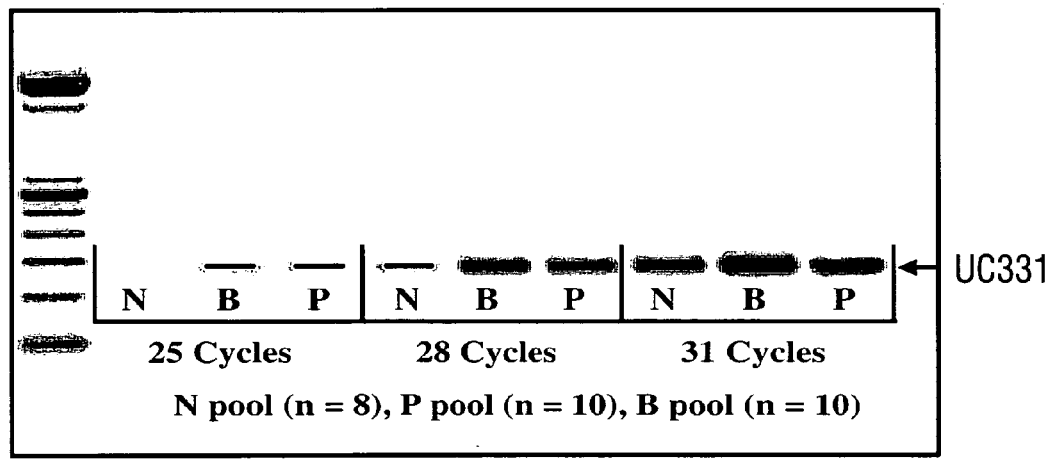

FIG. 8B. Relative quantitative RT-PCR™ showing that UC331 mRNA is roughly seven times more abundant in the peripheral blood of individuals with recurrent metastatic breast or prostate cancer compared to UC331 mRNA levels from healthy volunteers. PCR™ amplification of a UC331 specific cDNA fragment was performed using the same pools of normalized cDNAs as templates and similar experimental design as in the PCR™ shown in FIG. 8A. PCR™ reactions were terminated after either 25, 28 or 31 cycles. Pools of cDNAs were constructed from peripheral blood RNAs from eight healthy volunteers (N), ten individuals with recurrent metastatic prostate cancer (P), or ten individuals with recurrent metastatic breast cancer (B). The intensity of the bands are proportional to the relative amounts of UC331 mRNA in the individuals from which these cDNA pools were constructed.

Figure 9A:
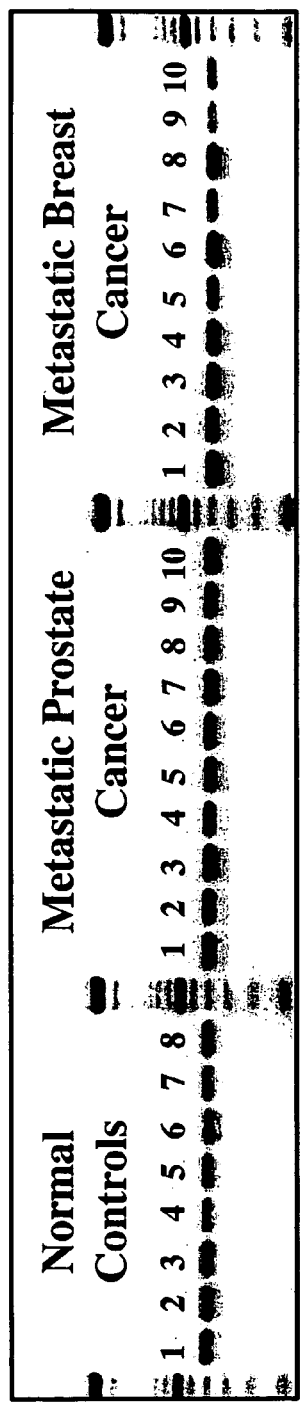

FIG. 9A. Relative quantitative RT-PCR™ of β-actin cDNA that was reverse transcribed from RNA isolated from the peripheral blood of eight healthy volunteers (group N), ten individuals with recurrent metastatic prostate cancer (group P), or ten individuals with recurrent metastatic breast cancer (group B). PCR™ was for 22 cycles.

Figure 9B:
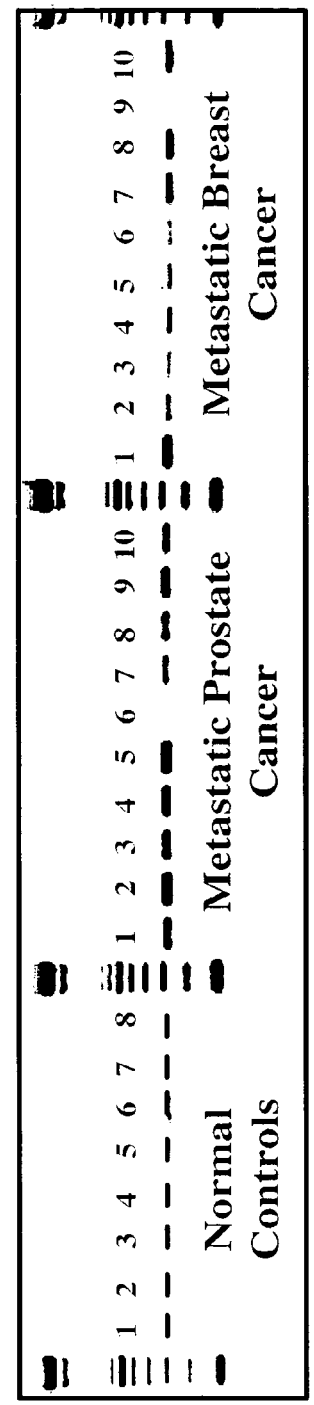

FIG. 9B. Relative quantitative RT-PCR™ of UC331 cDNA that was reverse transcribed from RNA isolated from the peripheral blood of eight healthy volunteers (group N), ten individuals with recurrent metastatic prostate cancer (group P), or ten individuals with recurrent metastatic breast cancer (group B). PCR™ was for 30 cycles.

Figure 10:
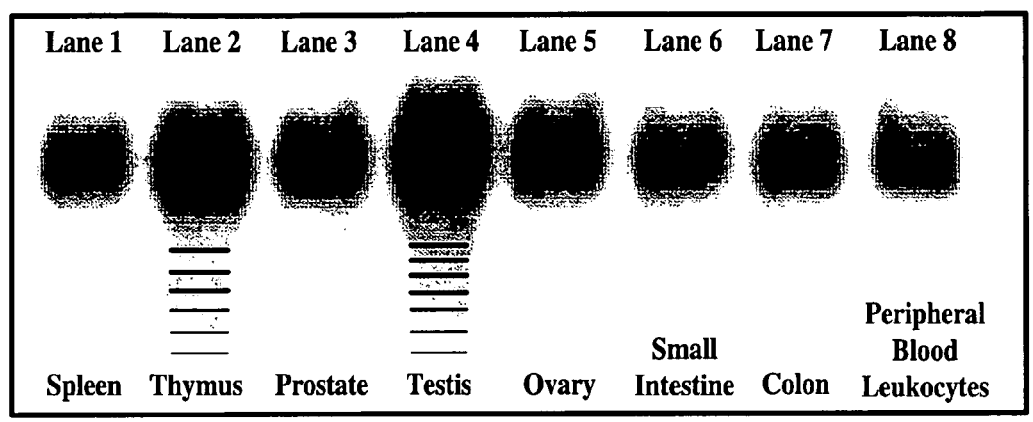

FIG. 10. Northern blot of polyadenylated mRNA isolated from various human tissues and probed with a $^{32}P$ labeled UC331 PCR™ product. Lanes one through eight contain approximately 2.0 µg of polyadenylated mRNA from spleen (lane 1), thymus (lane 2), prostate (lane 3), testis (lane 4), ovary (lane 5), small intestine (lane 6), colon (lane 7), and peripheral blood leukocytes (lane 8). Size standards provided by supplier indicate a message size of approximately 1.75 kb.

FIG. 11A, FIG. 11B, FIG. 11C, FIG. 11D, FIG. 11E, FIG. 11F, FIG. 11G, FIG. 11H, and FIG. 11I. DNA (SEQ ID NO:34) and predicted amino acid sequences (SEQ ID NO:35) for UC332 (KA000262) taken from Nagase et al. (1996) (GB:D87451). Indicated are a $C_3HC_4$ zinc RING finger motif (shaded and underlined with conserved cysteines and histidines in bold) located between amino acids 175 and 216, a nuclear localization signal (underlined), a putative leucine zipper sequence (shaded area with repeating leucines and isoleucines in bold), and a PEST sequence flanked by basic stretches of amino acids (underlined) located between amino acid positions 684-736.

FIG. 12. Comparison of zinc RING finger domains from representative proteins. Positions of conserved cysteines and the conserved histidine are indicated by shading. Similarities between the RING finger domains of UC332 and other proteins are lightly shaded. The RING finger domain of UC332 is slightly more similar to those found in the tumor suppressor gene, BRCA1, and the T cell repressor of transcription protein, rpt-1. However, BRCA1 and rpt-1 are clearly more similar to each other than they are to UC332, as indicated by the darkly shaded area. The transcription complex protein lacks the last conserved cysteine. The peptides shown are UC332 (SEQ ID NO:36), BRCA1 (SEQ ID NO:37), rpt-1 (SEQ ID NO:38), Traf5 (SEQ ID NO:39), HT2A (SEQ ID NO:40), MAT1 (SEQ ID NO:41), rfp (SEQ ID NO:42), bmi-1 (SEQ ID NO:43), CRZF (SEQ ID NO:44), and neu (SEQ ID NO:45).

Figure 13A:
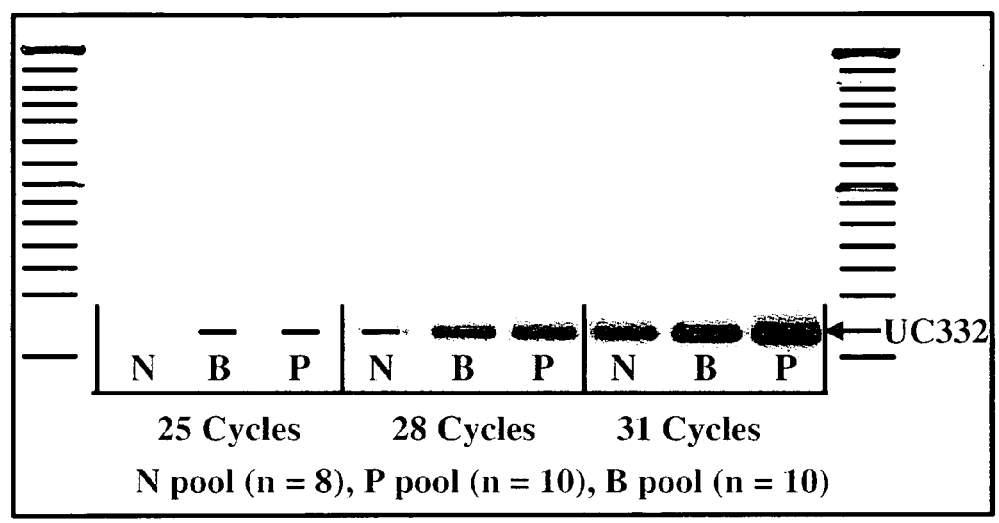

FIG. 13A. PCR™ amplification of a UC332 specific cDNA fragment using the same pools of normalized cDNAs as templates and similar experimental design as in the PCR™ shown in FIG. 8A. PCR™ reactions were terminated after either 25, 28 or 31 cycles. Pools of cDNAs were constructed from peripheral blood RNAs from eight healthy volunteers (N), ten individuals with recurrent metastatic prostate cancer (P), or ten individuals with recurrent metastatic breast cancer (B). The intensity of the bands are proportional to the relative amounts of UC332 mRNA in the individuals from which these cDNA pools were constructed.

Figure 13B:
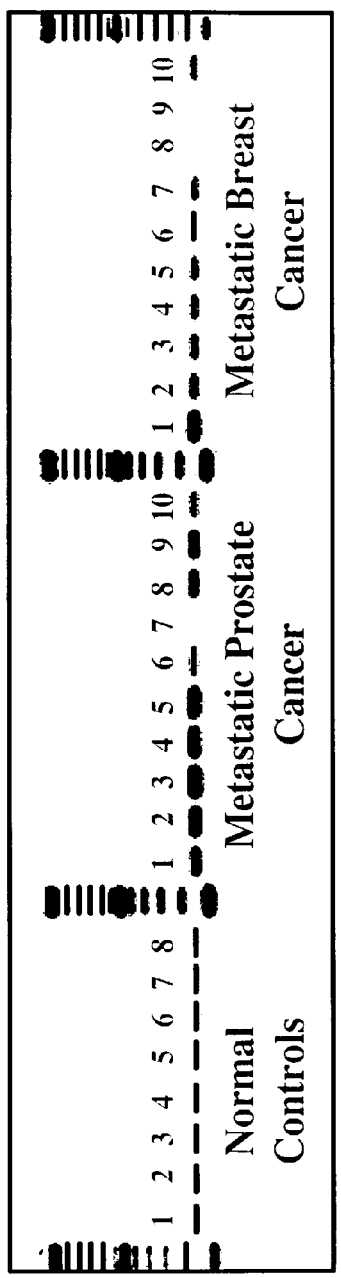

FIG. 13B. Relative quantitative RT-PCR™ of UC332 cDNA that was reverse transcribed from RNA isolated from the peripheral blood of eight healthy volunteers (N), ten individuals with recurrent metastatic prostate cancer (P), or ten individuals with recurrent metastatic breast cancer (B). PCR™ was for 26 cycles.

Figure 14:
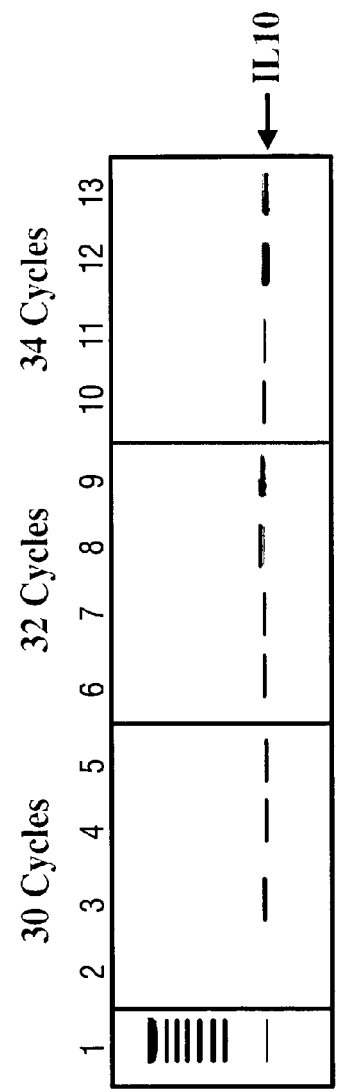

FIG. 14. Relative quantitative RT-PCR™ of IL-10 gene product isolated from the peripheral blood of five healthy volunteers (lanes 2, 6 and 10), eight healthy volunteers (lanes 3, 7 and 11) ten individuals with recurrent metastatic prostate cancer (lanes 4, 8 and 12), or ten individuals with recurrent metastatic breast cancer (lanes 5, 9 and 13). Molecular weight standards are shown in lane 1. PCR™ was for 30 cycles (lanes 2-5), 32 cycles (lanes 6-9) or 34 cycles (lanes 10-13).

4.0 DETAILED DESCRIPTION OF THE INVENTION

The present invention concerns the early detection, diagnosis, and prognosis of human disease states. Markers of a disease state, in the form of expressed RNA molecules of specified sequences or polypeptides expressed from these RNA molecules from the peripheral blood of individuals with the disease state, are disclosed. These markers are indicators of the disease state and, when differentially expressed relative to expression in a normal subject, are diagnostic for the presence of the disease state in patients. Such markers provide considerable advantages over the prior art in this field. Since they are detected in peripheral blood samples, it is not necessary to suspect that an individual exhibits the disease state (such as a tumor) before a sample may be taken, and in addition, the drawing of a blood sample is much less invasive and painful to the patient than tissue biopsies. The detection methods disclosed are thus suitable for widespread screening of asymptomatic individuals. Further, the methods provide for sensitive detection of disease state markers that is relatively unaffected by the presence of normal, non-diseased cells in a biological sample such as peripheral blood.

It will be apparent that the nucleic acid sequences disclosed will find utility in a variety of applications in disease state detection, diagnosis, prognosis and treatment. Examples of such applications within the scope of the present disclosure comprise amplification of markers of the disease state using specific primers, detection of markers of the disease state by hybridization with oligonucleotide probes, incorporation of isolated nucleic acids into vectors, expression of vector-incorporated nucleic acids as RNA and protein, and development of immunologic reagents corresponding to marker encoded products.

The identified disease state markers may in turn be used to design specific oligonucleotide probes and primers. In certain preferred embodiments the term "primer" as used here includes any nucleic acid capable of priming template-dependent synthesis of a nascent nucleic acid. In certain other embodiments the nucleic acid may be able to prime a template, but not be extended for synthesis of nascent nucleic acid that is complementary to the template. As used herein a "primer" may be at least about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 35, about 40, about 50, about, 75, about 100, about 150, about 200, about 300, about 400, about 500, to one base shorter in length than the template sequence at the 3' end of the primer to allow extension a nucleic acid chain, though the 5' end of the primer may extend in length beyond the 3' end of the template sequence. In certain embodiments of the present invention the term "template" may refer to a nucleic acid that is used in the creation of a complementary nucleic acid strand to the "template" strand. The template may be either RNA and/or DNA, and the complementary strand may also be RNA and/or DNA. In certain embodiments the complementary strand may comprise all or part of the complementary sequence to the "template", and/or may include mutations so that it is not an exact, complementary strand to the "template". Strands that are not exactly complementary to the template strand may hybridize specifically to the template strand in detection assays described here, as well as other assays known in the art, and such complementary strands that can be used in detection assays are part of the invention.

Such probes and primers may be of any length that would specifically hybridize to the identified marker gene sequences and may be at least about 14, about 15, about 16, about 17, about 18, about 19, about 20, about 21, about 22, about 23, about 24, about 25, about 26, about 27, about 28, about 29, about 30, about 35, about 40, about 50, about, 75, about 100, about 150, about 200, about 300, about 400, about 500, and in the case of probes, up to the full length of the sequences of the marker genes identified herein. Probes may also include additional sequence at their 5' and/or 3' ends so that they extent beyond the target sequence with which they hybridize.

When used in combination with nucleic acid amplification procedures, these probes and primers enable the rapid analysis of peripheral blood samples. In certain aspects of the invention, the term "amplification" may refer to any method or technique known in the art or described herein for duplicating or increasing the number of copies or amount of a target nucleic acid or its complement. In certain aspects of the invention, the term "amplicon" refers to the target sequence for amplification, and/or the amplification products of the target sequence for amplification. In certain other embodiments an "amplicon" may include the sequence of probes or primers used in amplification. This analysis assists physicians in detecting and diagnosing the disease state and in determining optimal treatment courses for individuals at varying stages of disease state progression.

The identified markers may also be used to identify and isolate full length gene sequences, including regulatory elements for gene expression, from genomic human DNA libraries. The cDNA sequences identified in the present disclosure may be used as hybridization probes to screen genomic human DNA libraries by conventional techniques. Once partial genomic clones have been identified, full-length genes may be isolated by "chromosomal walking" (also called "overlap hybridization"). See, Chinault & Carbon "Overlap Hybridization Screening: Isolation and Characterization of Overlapping DNA Fragments Surrounding the LEU2 Gene on Yeast Chromosome III." *Gene* 5: 111-126, 1979. Once a partial genomic clone has been isolated using a cDNA hybridization probe, nonrepetitive segments at or near the ends of the partial genomic clone may be used as hybridization probes in further genomic library screening, ultimately allowing isolation of entire gene sequences for the disease state markers of interest. It will be recognized that full length genes may be obtained using the small expressed sequence tags (ESTs) described in this disclosure using technology currently available and described in this disclosure (Sambrook et al., 1989; Chinault & Carbon, 1979). Sequences identified and isolated by such means may be useful in the detection of the prostate marker genes using the detection methods described herein, and are part of the invention.

The identified markers may be used to identify and isolate cDNA sequences. The EST sequences identified in the present disclosure may be used as hybridization probes to screen human cDNA libraries by conventional techniques. It will be recognized that these techniques would start by obtaining a high quality human cDNA library, many of which are readily available from commercial or other sources. The library may be plated on, for example, agarose plates containing nutrients, antibiotics and other conventional ingredients. Individual colonies may then be transferred to nylon or nitrocellulose membranes and the EST probes hybridized to complementary sequences on the membranes. Hybridization may be detected by radioactive or enzyme-linked tags associated with the hybridized probes. Positive colonies may be grown up and sequenced by, for example, Sanger dideoxynucleotide sequencing or similar methods well known in the art. Comparison of cloned cDNA sequences with known human or animal cDNA or genomic sequences may be performed using computer programs and databases well known in the art. Sequences identified and isolated by such means may be useful in the detection of the prostate marker genes using the detection methods described herein, and are part of the invention.

One of ordinary skill in the art could select segments from the identified marker genes for use in the different detection, diagnostic, or prognostic methods, vector constructs, antibody production, kit, and/or any of the embodiments described herein as part of the present invention. Marker gene sequences that are preferred for use in the invention are those published in the Genbank database that match the identified marker genes: Genbank Accession numbers D87451, T03013, X03558, M28130, Y00787, M57627 and D87451, as well as the sequences disclosed herein as SEQ ID NO:1, SEQ ID NO:2, SEQ ID NO:3, SEQ ID NO:29, SEQ ID NO:30, SEQ ID NO:34, SEQ ID NO:48 and SEQ ID NO:49 which also include sequences for previously uncharacterized marker genes (UC 302, SEQ ID NO:1; UC331 (human), SEQ ID NO:29; UC 331 (mouse), SEQ ID NO:30; UCPB 35, SEQ ID NO:48; UC 321, SEQ ID NO:49) identified in the present invention. For example, in certain embodiments, the sequences used to design probes and primers may include repetitive stretches of adenine nucleotides (poly-A tails) normally attached at the ends of the RNA for the identified marker genes. In certain other embodiments, probes and primers may be specifically designed to not include these or other segments from the identified marker genes, as one of ordinary skilled in the art may deem certain segments more suitable for use in the detection methods disclosed.

An example would be the use of sequences selected from a isolated genomic sequence of an identified marker gene that only contains exon sequence regions. One such metastatic cancer marker disclosed herein whose published sequence includes both exon and intron sequences is for the IL-8 gene that includes intron 3 (Genbank Accession # M28130). Exon sequences in the gene structure, as described in the Genbank listing for Accession # M28130, include bases 1482 to 1647, 2464 to 2599, 2871 to 2954, and 3370 to 4236. One of ordinary skill in the art may select segments from the published exon sequences, or may assemble them into a reconstructed mRNA sequence that does not contain intronic sequences, such as intron 3. Alternatively, the published sequence for IL-8 that reports a spliced form from which intron 3 is missing (Genbank Accession # Y00787) may be used. Similarly, one of ordinary skill in the art may select and/or assemble segments from any of the identified marker gene sequences into other useful forms, such as coding segment reconstructions of mRNA sequences from published genomic sequences of the identified marker genes, as part of the present invention. Such assembled sequences would be useful in designing probes and primers for detection, diagnosis, and prognosis embodiments of the invention described herein, as well as providing coding segments for protein translation.

For example, primers to detect the message of IL 8 using the transcribed portions of the marker sequence as set forth in the listing in Genbank Accession # M28130 may hybridize to nucleotides 1482 to 1503 and the complement of nucleotides 1626-1647. These particular primers would amplify a segment of message of the marker gene 166 base pairs in length. Primers designed to nucleotides 1482 to 1503 and the complement of nucleotides 2464 to 2483 would amplify a segment of message of the marker gene 186 base pairs long in messages that have the intervening intron between nucleotides 1648 to 2463 removed. Thus, one skilled in the art would be able to calculate the expected size of transcribed sequences from marker genes identified herein whose sequences are published either as genomic sequence, mRNA, or cDNA, as well as the sequences disclosed herein, taking into account the differences in size of the products produced depending on the presence or absence of intronic sequences. In preferred embodiments, the differences in size of amplification products using primers designed to regions flanking both sides of intron 3 in the IL-8 marker gene sequences identified (Genbank Accession # Y00787 and # M28130) can be used in detection, diagnosis, and/or prognosis of metastatic cancer. However, primers designed to regions of IL-8 sequences that do not flank intron 3, or the other marker genes, would not be expected to produce amplification products that include intronic segments. For example, primers designed to nucleotides 1 to 20 and the complement of nucleotides 200 to 220 of SEQ ID NO:1 would amplify a metastatic marker gene segment 220 base pairs long. Primers designed to nucleotides 115 to 138 and the complement of nucleotides 730 to 744 of SEQ ID NO:29 would amplify a metastatic marker gene segment 630 base pairs long. Primers designed to nucleotides 102 to 120 and the complement of nucleotides 381 to 401 of the IL-8 marker gene sequence identified in Genbank Accession # Y00787 would amplify a metastatic marker gene segment 302 base pairs long that would be approximately sevenfold less abundant in normal patients when compared to patients with metastatic prostate cancer. Primers can be designed to amplify the transcribed portions of the metastatic cancer markers that would include any length of nucleotide segment of the transcribed sequences, up to and including the full length of each marker gene message. It is preferred that the amplified segments of identified marker genes be an amplicon of at least about 50 to about 500 base pairs in length. It is particularly preferred that the amplified segments of identified marker genes be an amplicon of at least about 100 to about 415 base pairs in length, and/or no longer in length than the amplified segment used to normalize the quantity of message being amplified in the detection assays described herein. Such assays include RNA fingerprinting methods, however, differential expression detected by any other means, including other RNA fingerprinting methods known in the art would fall within the scope of the present invention. The predicted size of the amplified metastatic cancer marker gene segment, calculated by the location of the primers relative to the transcribed sequence, would be used to determine if the detected amplification product is indeed the marker gene being amplified. Sequencing the band that matches the expected size of the amplification product and comparison to the known or disclosed sequence of the marker gene would confirm that the marker gene is being amplified and detected.

Other embodiments would not remove all or part of the intronic sequences. A preferred embodiment would be a reconstructed IL-8 mRNA sequence, using the published sequence as described in the Genbank listing for Accession # M28130, that would include intron 3. Similarly, in certain embodiments regions of non-coding sequence may or may not be selected from the identified marker genes.

It is important to note that UC-325 (IL-8) serology in combination with PSA and f/t PSA can more accurately differentially diagnose prostate cancer and BPH. This method provides significant advantages over previous methodologies for detecting prostatic cancer, which often failed to differentiate between prostatic cancer and BPH.

In certain embodiments of the invention the terms "expression" or "gene expression" may refer to either production of RNA message or translation of RNA message into proteins or polypeptides. Detection of either types of gene expression in use of any of the methods described herein are part of the invention.

As used herein in the context of various of the instant compositions and methods, the term "protein" will be understood to mean a proteinaceous segment that is longer than about 75 contiguous amino acids and/or, in most aspects, comprises more that about 70% of the amino acids encoded by a gene. As used herein in the context of various of the instant compositions and methods, the term "polypeptide" will be understood to mean a proteinaceous segment that is longer than about 50 contiguous amino acids in length, and the term "peptide" will be understood to mean a proteinaceous segment that is between about 6 and about 50 contiguous amino acids in length.

4.1 Terms Used

| | |
|---|---|
| HK2: | human kallekrein 2 gene product |
| PAP: | prostatic acid phosphatase |
| PSA: | prostate specific antigen |
| PSMA: | prostate specific membrane antigen (Folic Acid Hydrolase) |
| $PSP_{94}$: | prostate secreted protein (94 kDa) |
| t-PSA: | total PSA |

-continued

| | |
|---|---|
| f/t (Free,Total PSA): | ratio of free to total PSA, measured in serum specimens with moderately elevated t-PSA |
| IL-8: | Interleukin-8 (UC 325) |
| IL-10: | Interleukin-10 |
| SENSITIVITY = | (True Positives/(True Positives + False Negatives); plotted on y-axis of ROC curve. |
| SPECIFICITY = | (True Negatives/(True Negatives + False Positives); plotted on x-axis (as 1-Specficity) of ROC curve |
| ROC: | Receiver Operator Character Curve; a means of plotting sensitivity and specificity over a range of cut-off (threshold) values. |
| BPH: | benign prostatic hyperplasia (or hypertrophy) |
| CaP: | adenocarcinoma of the prostate |
| Stage A CaP: | organ-confined clinical stage of prostate cancer in which tumor is not palpable by a digital rectal exam (DRE) (Walsh & Worthington, 1995). |
| Stage B CaP: | organ-confined clinical stage of prostate cancer in which tumor is palpable by a digital rectal exam and involves one or both lobes of the gland (Walsh & Worthington, 1995). |
| Stage C CaP: | non-organ-confined clinical stage of prostate cancer in which tumor is palpable by a DRE and invades beyond the capsule and/or the seminal vesicles (Walsh & Worthington, 1995). |
| Stage D CaP: | non-organ-confined clinical stage of prostate cancer characterized by metastasis to lymph nodes, bone or other distant organ site (Walsh & Worthington, 1995). |

4.2 Nucleic Acids

As described in Examples 1 through 7, the present disclosure provides eight markers of a disease state, identified by RNA fingerprinting. These include five previously uncharacterized gene products, as well as nucleic acid products of the IL-8 (interleukin 8), IL-10 (interleukin 10) and human elongation factor 1-alpha genes.

In one embodiment, the sequences of isolated nucleic acids disclosed herein find utility as hybridization probes or amplification primers. These nucleic acids may be used, for example, in diagnostic evaluation of tissue samples or employed to clone full length cDNAs or genomic clones corresponding thereto. In certain embodiments, these probes and primers comprise oligonucleotide fragments. Such fragments are of sufficient length to provide specific hybridization to an RNA or DNA sample extracted from tissue. The sequences typically will be 10-20 nucleotides, but may be longer. Longer sequences, e.g., 40, 50, 100, 500 and even up to full length, are preferred for certain embodiments.

Nucleic acid molecules having contiguous stretches of about 10, 15, 17, 20, 30, 40, 50, 60, 75 or 100 or 500 nucleotides of a sequence SEQ ID NO:1, SEQ ID NO:2, SEQ ID NO:3, SEQ ID NO:29, SEQ ID NO:30, SEQ ID NO:34, SEQ ID NO:48, SEQ ID NO:49, or a product of the IL-10 gene are contemplated. Molecules that are complementary to the above mentioned sequences and that bind to these sequences under high stringency conditions are also contemplated. These probes are useful in a variety of hybridization embodiments, such as Southern and northern blotting. In some cases, it is contemplated that probes may be used that hybridize to multiple target sequences without compromising their ability to effectively diagnose the disease state.

Various probes and primers may be designed around the disclosed nucleotide sequences. Primers may be of any length but, typically, are 10-20 bases in length. By assigning numeric values to a sequence, for example, the first residue is 1, the second residue is 2, etc., an algorithm defining all primers may be proposed:

n to n+y where n is an integer from 1 to the last number of the sequence and y is the length of the primer minus one (9 to 19), where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

The values of n in the algorithm above for each of the nucleic acid sequences is: SEQ ID NO:1, n=387; SEQ ID NO:2, n=366; SEQ ID NO:3, n=598; SEQ ID NO:29, n=1614; SEQ ID NO:30, n=1268; SEQ ID NO:34, n=3205; SEQ ID NO:48, n=253; SEQ ID NO:49, n=183.

In certain embodiments, it is contemplated that multiple probes may be used for hybridization to a single sample. For example, an alternatively spliced form of IL-8 mRNA, containing intron 3, may be detected by probing human tissue samples with oligonucleotides specific for intron 3 and for exon portions of the IL-8 transcript. Hybridization with the intron 3 and exon sequences probe would be indicative of a normal individual and binding to only the exon probe would be indicative of metastatic prostate cancer.

The use of a hybridization probe of between 17 and 100 nucleotides in length allows the formation of a duplex molecule that is both stable and selective. Molecules having complementary sequences over stretches greater than 20 bases in length are generally preferred in order to increase stability and selectivity of the hybrid, and thereby improve the quality and degree of hybrid molecules. It is generally preferred to design nucleic acid molecules having stretches of 20 to 30 nucleotides, or even longer. Such fragments may be readily prepared by, for example, directly synthesizing the fragment by chemical means or by introducing selected sequences into recombinant vectors for recombinant production.

The complement of a nucleic acid sequence is well known in the art and is based on the anti-parallel, Watson-Crick pairing of nucleotides (bases) for a given nucleic acid polymer (strand). Two complementary strands of DNA are formed into a duplex by pairing of bases, e.g. "G" to "C", "C" to "G", "A" to "T" (in the case of DNA) or "U" (in the case of RNA) and all "T" or "U" to "A", in reverse 5' to 3' orientation (anti-parallel). As used herein therefore, the term "complement" defines a second strand of nucleic acid which will hybridize to a first strand of nucleic acid to form a duplex molecule in which base pairs are matched as G:C, C:G, A:T/U or T/U:A.

A complement may also be described as a fragment of DNA (nucleic acid segment) or a synthesized single stranded oligomer that may contain small mismatches or gaps when hybridized to its complement, but that is able to hybridize to the complementary DNA under high stringency conditions. To hybridize is understood to mean the forming of a double stranded molecule or a molecule with partial double stranded nature. High stringency conditions are those that allow hybridization between two homologous nucleic acid sequences, but precludes hybridization of random sequences. For example, hybridization at low temperature and/or high ionic strength is termed low stringency. Hybridization at high temperature and/or low ionic strength is termed high stringency. Low stringency is generally performed at 0.15 M to 0.9 M NaCl at a temperature range of 20° C. to 50° C. High stringency is generally performed at 0.02 M to 0.15 M NaCl at a temperature range of 50° C. to 70° C. It is understood that the temperature and ionic strength of a desired stringency are determined in part by the length of the particular probe, the length and base content of the target sequences, and to the presence of formamide, tetramethylammonium chloride or other solvents in the hybridization mixture. It is also understood that these ranges are mentioned by way of example only, and that the desired stringency for a particular hybridization reaction is often determined empirically by comparison to positive and negative controls.

Accordingly, the nucleotide sequences of the disclosure may be used for their ability to selectively form duplex molecules with complementary stretches of genes or RNAs or to provide primers for amplification of DNA or RNA from tissues. Depending on the application envisioned, it is preferred to employ varying conditions of hybridization to achieve varying degrees of selectivity of probe towards target sequence.

For applications requiring high selectivity, it is preferred to employ relatively stringent conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions may be rendered more stringent by the addition of increasing amounts of formamide.

For certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition may be provided by about 0.1 to 0.25 M NaCl at temperatures of about 37° C. to about 55° C., while a low stringency condition may be provided by about 0.15 M to about 0.9 M salt, at temperatures ranging from about 20° C. to about 55° C. Thus, hybridization conditions may be readily manipulated depending on the desired results.

The following codon chart may be used, in a site-directed mutagenic scheme, to produce nucleic acids encoding the same or slightly different amino acid sequences of a given nucleic acid:

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |

TABLE 1-continued

| Amino Acids | | | Codons | |
|---|---|---|---|---|
| Tryptophan | Trp | W | UGG | |
| Tyrosine | Tyr | Y | UAC | UAU |

In other embodiments, hybridization may be achieved under conditions of, for example, 50 mM Tris-HCl (pH 8.3), 75 mM KCl, 3 mM MgCl$_2$, 10 mM dithiothreitol, at temperatures between approximately 20° C. to about 37° C. Other hybridization conditions utilized may include approximately 10 mM Tris-HCl (pH 8.3), 50 mM KCl, 1.5 mM MgCl$_2$, at temperatures ranging from approximately 40° C. to about 72° C.

In certain embodiments, it is preferred to employ isolated nucleic acids of the present disclosure in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may employ a fluorescent label or an enzyme tag such as urease, alkaline phosphatase or peroxidase, instead of radioactive or other environmentally undesirable reagents. In the case of enzyme tags, colorimetric indicator substrates are known which may be employed to provide a detection means visible to the human eye or spectrophotometrically, to identify specific hybridization with complementary nucleic acid-containing samples.

In general, it is contemplated that the hybridization probes described herein are useful both as reagents in solution hybridization, as in PCR, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under selected conditions. The selected conditions depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

It is understood that this disclosure is not limited to the particular probes disclosed herein and particularly is intended to encompass at least isolated nucleic acids that are hybridizable to nucleic acids comprising the disclosed sequences or that are functional sequence analogs of these nucleic acids. For example, a nucleic acid of partial sequence may be used to identify a structurally-related gene or the full length genomic or cDNA clone from which it is derived. Methods for generating cDNA and genomic libraries which may be used as a target for the above-described probes are known in the art (Sambrook et al., 1989).

For applications in which the nucleic acid segments of the present disclosure are incorporated into vectors, such as plasmids, cosmids or viruses, these segments may be combined with other DNA sequences, such as promoters, polyadenylation signals, restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol.

DNA segments encoding a specific gene may be introduced into recombinant host cells for expressing a specific structural or regulatory protein. Alternatively, through the application of genetic engineering techniques, subportions or derivatives of selected genes may be employed. Upstream regions containing regulatory regions such as promoter regions may be isolated and subsequently employed for expression of the selected gene.

Where an expression product is to be generated, it is possible for the nucleic acid sequence to be varied while retaining the ability to encode the same product. Reference to the codon chart, provided in Table 1, enables the design of any nucleic acid encoding the same protein or peptide product.

4.2.1 Engineering Expression Constructs

In certain embodiments, the present invention involves the manipulation of genetic material to produce expression constructs that encode therapeutic genes. Such methods involve the generation of expression constructs containing, for example, a heterologous DNA encoding a gene of interest and a means for its expression, replicating the vector in an appropriate helper cell, obtaining viral particles produced therefrom, and infecting cells with the recombinant virus particles.

The gene will be a therapeutic gene such as one or more of the cancer marker genes discussed herein above. In the context of gene therapy, the gene will be a heterologous DNA, meant to include DNA derived from a source other than the viral genome which provides the backbone of the vector. Finally, the virus may act as a live viral vaccine and express an antigen of interest for the production of antibodies there against. The gene may be derived from a prokaryotic or eukaryotic source such as a bacterium, a virus, a yeast, a parasite, a plant, or even an animal. The heterologous DNA also may be derived from more than one source, i.e., a multigene construct or a fusion protein. The heterologous DNA also may include a regulatory sequence which may be derived from one source and the gene from a different source.

4.2.2 Antisense Constructs

The IL-8 gene products identified herein (SEQ ID NO:2 and SEQ ID NO:3) are suitable targets for therapies directed towards modification of immune response to tumors. Other suitable targets for such therapies include SEQ ID NO:1, SEQ ID NO:29, SEQ ID NO:34, SEQ ID NO:48, SEQ ID NO:49 or nucleic acid products of the IL-10 gene. For therapeutic benefit, these would be expressed as an antisense nucleic acid, so as to inhibit the expression of these nucleic acids in peripheral leukocytes. The term "antisense nucleic acid" is intended to refer to the oligonucleotides complementary to the base sequences of UCPB 35, UC 302, UC 321, UC 331, UC 332, IL-8 or IL-10-encoding DNA and RNA. Antisense oligonucleotides, when introduced into a target cell, specifically bind to their target nucleic acid and interfere with transcription, RNA processing, transport and/or translation. Targeting double-stranded (ds) DNA with oligonucleotide leads to triple-helix formation; targeting RNA will lead to double-helix formation.

Antisense constructs may be designed to bind to the promoter and other control regions, exons, introns or even exon-intron boundaries of a gene. Antisense RNA constructs, or DNA encoding such antisense RNAs, may be employed to inhibit gene transcription or translation or both within a host cell, either in vitro or in vivo, such as within a host animal, including a human subject. Nucleic acid sequences comprising "complementary nucleotides" are those which are capable of base-pairing according to the standard Watson-Crick complementary rules. That is, that the larger purines will base pair with the smaller pyrimidines to form only combinations of guanine paired with cytosine (G:C) and adenine paired with either thymine (A:T), in the case of DNA, or adenine paired with uracil (A:U) in the case of RNA.

As used herein, the terms "complementary" or "antisense sequences" mean nucleic acid sequences that are substantially complementary over their entire length and have very few base mismatches. For example, nucleic acid sequences of fifteen bases in length may be termed complementary when they have a complementary nucleotide at thirteen or fourteen positions with only single or double mismatches. Naturally, nucleic acid sequences which are "completely complementary" will be nucleic acid sequences which are entirely complementary throughout their entire length and have no base mismatches.

While all or part of the gene sequence may be employed in the context of antisense construction, statistically, any sequence 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

4.2.3 Vectors for Cloning, Gene Transfer and Expression

Within certain embodiments expression vectors are employed in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

4.2.3.1 Regulatory Elements

Throughout this application, the term "expression construct" is meant to include any type of genetic construct containing a nucleic acid coding for a gene product in which part or all of the nucleic acid coding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box. However, in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp before activity begins to decline. Depending on the promoter, it appears that individual elements can function either co-operatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter, and glyceraldehyde-3-phosphate dehydrogenase promoter can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several elements/promoters which may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers, and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) also could be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

| ENHANCER/PROMOTER |
| --- |
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Prealbumin (Transthyretin) |
| Muscle Creatine Kinase |
| Elastase I |
| Metallothionein |
| Collagenase |
| Albumin Gene |
| α-Fetoprotein |
| τ-Globin |
| β-Globin |
| e-fos |
| c-HA-ras |
| Insulin |
| Neural Cell Adhesion Molecule (NCAM) |
| α1-Antitrypsin |
| H2B (TH2B) Histone |
| Mouse or Type I Collagen |
| Glucose-RegulatedProteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |

TABLE 2-continued

ENHANCER/PROMOTER

Retroviruses
Papilloma Virus
Hepatitis B Virus
Human Immunodeficiency Virus
Cytomegalovirus

TABLE 3

| Element | Inducer |
| --- | --- |
| MT II | Phorbol Ester (TPA) |
|  | Heavy metals |
| MMTV (mouse mammary tumor virus) | Glucocorticoids |
| β-Interferon | poly(rI)X |
|  | poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

Where a cDNA insert is employed, typically one will typically include a polyadenylation signal to effect proper polyadenylation of the gene transcript. The nature of the polyadenylation signal is not believed to be crucial to the successful practice of the invention, and any such sequence may be employed, such as human growth hormone and SV40 polyadenylation signals. Also contemplated as an element of the expression construct is a terminator. These elements can serve to enhance message levels and to minimize read through from the construct into other sequences.

4.2.3.2 Selectable Markers

In certain embodiments of the invention, the cells containing nucleic acid constructs of the present invention may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin, and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

4.2.3.3 Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome, and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). Preferred gene therapy vectors are generally viral vectors.

Although some viruses that can accept foreign genetic material are limited in the number of nucleotides they can accommodate and in the range of cells they infect, these viruses have been demonstrated to successfully effect gene expression. However, adenoviruses do not integrate their genetic material into the host genome and therefore do not require host replication for gene expression, making them ideally suited for rapid, efficient, heterologous gene expression. Techniques for preparing replication defective viruses are well known in the art.

Of course in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

Viruses used as gene vectors were DNA viruses may include the papovaviruses (e.g., simian virus 40, bovine papilloma virus, and polyoma) (Ridgeway, 1988; Baichwal and Sugden, 1986) and adenoviruses (Ridgeway, 1988; Baichwal and Sugden, 1986).

One of the preferred methods for in vivo delivery involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to express an antisense polynucleotide that has been cloned therein.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retroviral infection, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNAs issued from this promoter possess a 5'-tripartite leader (TPL) sequence which makes them preferred mRNAs for translation.

In currently used systems, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of adenovirus vectors which are replication deficient depend on a unique helper cell line, designated 293, which is transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3, or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells, may be derived from the cells of other mammalian species that are permissive for human adenovirus. Such cells include, e.g., Vero cells or other monkey embryonic mesenchymal or epithelial cells. As discussed, the preferred helper cell line is 293.

Recently, Racher et al., (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) are employed as follows. A cell innoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking is initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking is commenced for another 72 hr.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

A typical vector applicable to practicing the present invention is replication defective and will not have an adenovirus E1 region. Thus, it will be most convenient to introduce the polynucleotide encoding the HRT gene at the position from which the E1-coding sequences have been removed. However, the position of insertion of the construct within the adenovirus sequences is not critical. The polynucleotide encoding the HET gene may also be inserted in lieu of the deleted E3 region in E3 replacement vectors as described by Karlsson et al., (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Other gene transfer vectors may be constructed from retroviruses. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env. that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences, and also are required for integration in the host cell genome (Coffin, 1990).

In order to construct a retroviral vector, a nucleic acid encoding a HET gene is inserted into the viral genome in the place of certain viral sequences to produce a virus that is replication-defective. In order to produce virions, a packaging cell line containing the gag, pol, and env genes, but without the LTR and packaging components, is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are capable of infecting a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses has been designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bear those surface antigens with an ecotropic virus in vitro was demonstrated (Roux et al., 1989).

There are certain limitations to the use of retrovirus vectors. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This may result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs. Vectors derived from viruses such as vaccinia virus (Ridgeway, 1988; Baichwal and Sugden, 1986; Coupar et al., 1988), adeno-associated virus (AAV) (Ridgeway, 1988; Baichwal and Sugden, 1986; Hermonat and Muzycska, 1984), and herpes viruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight has been gained into the structure-function relationship of different viral sequences. In vitro studies showed that the virus could retain the ability for helper-dependent packaging and reverse transcription despite the deletion of up to 80% of its genome (Horwich et al., 1990). This suggests that large portions of the genome can be replaced with foreign genetic material. The hepatotropism and persistence (integration) are particularly attractive properties for liver-directed gene transfer. Chang et al. (1991) recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

To effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990), DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the HET gene may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a HET gene may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa, and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a HET gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a HET gene also may be specifically delivered into a cell type such as lung, epithelial, or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia), and MAA (melanoma) can be used similarly as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

Examples of useful mammalian host cell lines are Vero and HeLa cells and cell lines of Chinese hamster ovary, W138, BHK, COS-7, 293, HepG2, NIH3T3, RIN, and MDCK cells. In addition, a host cell strain may be chosen that modulates the expression of the inserted sequences, or modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, antimetabolite resistance can be used as the basis of selection for dhfr: that confers resistance to methotrexate; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent T-cells.

Large scale suspension culture of mammalian cells in stirred tanks is a common method for production of recombinant proteins. Two suspension culture reactor designs are in wide use—the stirred reactor and the airlift reactor. The stirred design has been used successfully on an 8000 liter capacity for the production of interferon. Cells are grown in a stainless steel tank with a height-to-diameter ratio of 1:1 to 3:1. The culture usually is mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid which is free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

4.3 Encoded Proteins

Once the entire coding sequence of a marker-associated gene has been determined, the gene may be inserted into an appropriate expression system. The gene may be expressed in any number of different recombinant DNA expression systems to generate large amounts of the polypeptide product, which may then be purified and used to vaccinate animals to generate antisera which may also be useful in the practice of the disclosed invention. For example, polyclonal or monoclonal antibodies may be prepared that specifically bind to the protein product(s) of the marker-associated gene. Such antibodies may be incorporated into kits that may in turn be used for detection and diagnosis of the disease state in peripheral blood or other tissue samples.

Examples of expression systems known in the art include bacteria such as *E. coli*, yeast such as *Saccharomyces cerevisia* and *Pichia pastoris*, baculovirus, and mammalian expression systems such as in Cos or CHO cells. In one embodiment, polypeptides are expressed in *E. coli* and in baculovirus expression systems. A complete gene may be expressed or, alternatively, fragments of the gene encoding portions of polypeptide may be produced.

In one embodiment, the gene sequence encoding the polypeptide is analyzed to detect putative transmembrane sequences. Such sequences are typically very hydrophobic and are readily detected by the use of sequence analysis software, such as Lasergene (DNAstar, Madison, Wis.). The presence of transmembrane sequences is often deleterious when a recombinant protein is synthesized in many expression systems, especially *E. coli*, as it leads to the production of insoluble aggregates that are difficult to renature into the native conformation of the protein. Deletion of transmembrane sequences typically does not significantly alter the conformation of the remaining protein structure.

Moreover, transmembrane sequences, being by definition embedded within a membrane, are inaccessible. Antibodies to these sequences will not prove useful for in vivo or in situ studies. Deletion of transmembrane-encoding sequences from the genes used for expression may be achieved by conventional techniques. For example, restriction enzyme sites may be used to excise the desired gene fragment, or PCR-type amplification may be used to amplify only the desired part of the gene.

In another embodiment, computer sequence analysis is used to determine the location of predicted major antigenic determinant epitopes of the polypeptide. Software capable of carrying out this analysis is readily available commercially. Such software typically uses conventional algorithms such as the Kyte/Doolittle or Hopp/Woods methods for locating hydrophilic sequences which are characteristically found on the surface of proteins and are, therefore, likely to act as antigenic determinants.

Once this analysis is made, polypeptides may be prepared which contain at least the essential features of the antigenic determinant and which may be employed in the generation of antisera against the polypeptide. Minigenes or gene fusions encoding these determinants may be constructed and inserted into expression vectors by conventional methods, for example, using PCR cloning methodology.

A gene or gene fragment encoding a polypeptide may be inserted into an expression vector by conventional subcloning techniques. In one embodiment, an *E. coli* expression vector is used which produces the recombinant polypeptide as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6×His system (Qiagen, Chatsworth, Calif.).

Some of these systems produce recombinant polypeptides bearing only a small number of additional amino acids, which are unlikely to affect the antigenic character of the recombinant polypeptide. For example, both the FLAG system and the 6×His system add only short sequences, both of which are known to be poorly antigenic and which do not adversely affect folding of the polypeptide to its native conformation. Other fusion systems produce polypeptide where it is desirable to excise the fusion partner from the desired polypeptide. In one embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

In another embodiment, the expression system used is one driven by the baculovirus polyhedron promoter. The gene encoding the polypeptide may be manipulated by conventional techniques in order to facilitate cloning into the baculovirus vector. One baculovirus vector is the pBlueBac vector (Invitrogen, Sorrento, Calif.). The vector carrying the gene for the polypeptide is transfected into *Spodoptera frugiperda* (Sf9) cells by conventional protocols, and the cells are cultured and processed to produce the recombinant antigen. See Summers et al., A MANUAL OF METHODS FOR BACULOVIRUS VECTORS AND INSECT CELL CULTURE PROCEDURES, Texas Agricultural Experimental Station; U.S. Pat. No. 4,215,051 (incorporated by reference).

As an alternative to recombinant polypeptides, synthetic peptides corresponding to the antigenic determinants may be prepared. Such peptides are at least six amino acid residues long, and may contain up to approximately 50 residues, which is the approximate upper length limit of automated peptide synthesis machines, such as those available from Applied Biosystems (Foster City, Calif.). Use of such small peptides for vaccination typically requires conjugation of the peptide to an immunogenic carrier protein such as hepatitis B surface antigen, keyhole limpet hemocyanin or bovine serum albumin. Methods for performing this conjugation are well known in the art.

In one embodiment, amino acid sequence variants of the polypeptide may be prepared. These may, for instance, be minor sequence variants of the polypeptide which arise due to natural variation within the population or they may be homologues found in other species. They also may be sequences which do not occur naturally but which are sufficiently similar that they function similarly and/or elicit an immune response that cross-reacts with natural forms of the polypeptide. Sequence variants may be prepared by conventional methods of site-directed mutagenesis such as those described above for removing the transmembrane sequence.

Amino acid sequence variants of the polypeptide may be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. An example of the latter sequence is the SH2 domain, which induces protein binding to phosphotyrosine residues.

Substitutional variants typically exchange one amino acid for another at one or more sites within the protein and may be designed to modulate one or more properties of the polypeptide, such as stability against proteolytic cleavage. Substitutions preferably are conservative, that is, one amino acid is replaced with another of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; histidine to asparagine or glutamine; isoleucine to leucine or valine; leucine to valine or isoleucine; lysine to arginine or glutamine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Insertional variants include fusion proteins such as those used to allow rapid purification of the polypeptide and also may include hybrid proteins containing sequences from other homologous proteins and polypeptides. For example, an insertional variant may include portions of the amino acid sequence of the polypeptide from one species, together with portions of the homologous polypeptide from another species. Other insertional variants may include those in which additional amino acids are introduced within the coding sequence of the polypeptide. These typically are smaller insertions than the fusion proteins described above and are introduced, for example, to disrupt a protease cleavage site.

In one embodiment, major antigenic determinants of the polypeptide are identified by an empirical approach in which portions of the gene encoding the polypeptide are expressed in a recombinant host, and the resulting proteins tested for their ability to elicit an immune response. For example, PCR may be used to prepare a range of peptides lacking successively longer fragments of the C-terminus of the protein. The immunoprotective activity of each of these peptides then identifies those fragments or domains of the polypeptide which are essential for this activity. Further studies in which only a small number of amino acids are removed at each iteration then enables the location of the antigenic determinants of the polypeptide.

Another embodiment for the preparation of polypeptides according to the disclosure is the use of peptide mimetics. Mimetics are peptide-containing molecules which mimic elements of protein secondary structure. See, for example, Johnson et al., "Peptide Turn Mimetics" in *BIOTECHNOLOGY AND PHARMACY*, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule.

Successful applications of the peptide mimetic concept have thus far focused on mimetics of β-turns within proteins, which are known to be highly antigenic. Likely β-turn structure within an polypeptide may be predicted by computer-based algorithms as discussed above. Once the component amino acids of the turn are determined, peptide mimetics may be constructed to achieve a similar spatial orientation of the essential elements of the amino acid side chains.

4.4 Preparation of Antibodies Specific for Encoded Proteins 4.4.1 Expression of Proteins from Cloned cDNAs The cDNAs of sequences comprising SEQ ID NO:1, SEQ ID NO:2, SEQ ID NO:3, SEQ ID NO:29, SEQ ID NO:30, SEQ ID NO:34, SEQ ID NO:48 and SEQ ID NO:49 may be expressed as encoded peptides or proteins. The engineering of DNA segment(s) for expression in a prokaryotic or eukaryotic system may be performed by techniques generally known in the art of recombinant expression. It is believed that virtually any expression system may be employed in the expression of the claimed isolated nucleic acids.

Both cDNA and genomic sequences are suitable for eukaryotic expression, as the host cell generally processes the genomic transcripts to yield functional mRNA for translation into protein. In addition, it is possible to use partial sequences for generation of antibodies against discrete portions of a gene product, even when the entire sequence of that gene product remains unknown. Computer programs are available to aid in the selection of regions which have potential immunologic significance. Software capable of carrying out this analysis is readily available commercially, for example MacVector (IBI, New Haven, Conn.). The software typically uses conventional algorithms such as the Kyte/Doolittle or Hopp/Woods methods for locating hydrophilic sequences which are characteristically found on the surface of proteins and are therefore likely to act as antigenic determinants.

It may be more convenient to employ as the recombinant gene a cDNA version of the gene. It is believed that the use of a cDNA version provides advantages in that the size of the gene is generally much smaller and more readily employed to transfect the targeted cell than a genomic gene, which is typically up to an order of magnitude larger than the cDNA gene. However, the possibility of employing a genomic version of a particular gene or fragments thereof is specifically contemplated.

As used herein, the terms "engineered" and "recombinant" cells are intended to refer to a cell into which an exogenous DNA segment or gene, such as a cDNA or gene has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic gene, and also include genes positioned adjacent to a promoter not naturally associated with the particular introduced gene.

To express a recombinant encoded protein or peptide, whether mutant or wild-type, in accordance with the present disclosure one prepares an expression vector that comprises one of the claimed isolated nucleic acids under the control of, or operatively linked to, one or more promoters. To bring a coding sequence "under the control of" a promoter, or to "operatively link" to a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded recombinant protein. This is the meaning of "recombinant expression" in this context.

Many conventional techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium*, *Serratia marcescens*, and various *Pseudomonas* species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is often transformed using pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which may be used by the microbial organism for expression of its own proteins.

In addition, phage vectors containing replicon and control sequences that are compatible with the host microorganism may be used as transforming vectors in connection with these hosts. For example, the phage lambda GEM™-11 may be utilized in making a recombinant phage vector which may be used to transform host cells, such as *E. coli* LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling their ligation into plasmid vectors.

For expression in *Saccharomyces*, the plasmid YRp7, for example, is commonly used. This plasmid already contains the trp1 gene which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autographia californica* nuclear polyhidrosis virus (AcNPV) is used as a vector to express foreign genes. The virus grows in *Spodoptera frugiperda* cells. The isolated nucleic acid coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051 (Smith)).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cells lines or host systems may be chosen to help ensure the correct modification and processing of the foreign protein expressed. Expression vectors for use in mammalian cells ordinarily include an origin of replication, a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible to utilize promoter or control sequences normally associated with the gene sequence of interest, provided such control sequences are compatible with the host cell systems.

A number of viral based expression systems may be utilized. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) results in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG codon, may additionally need to be provided. This need is readily determinable and the necessary signals readily provided. It is well known that the initiation codon must be in-frame (or in-phase) with the reading frame of the desired coding sequence to help ensure translation of the entire insert. These exogenous translational control signals and initiation codons may be of a variety of origins, both natural and synthetic. The efficiency of expression may be enhanced by the inclusion of appropriate transcription enhancer elements or transcription terminators (Bittner et al., 1987).

In eukaryotic expression, it is typically preferred to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells may be transformed with vectors controlled by appropriate expression control elements (e.g., promoter or enhancer sequences, transcription terminators, polyadenylation sites, etc.), and a selectable marker. Following the introduction of foreign DNA, engineered cells may be allowed to grow for 1-2 days in an enriched medium and then are switched to a selective media. The selectable marker in the recombinant plasmid confers resistance to the transformant and allows cells to stably integrate the plasmid into their chromosomes and grow to form foci which in turn may be cloned and expanded into cell lines.

A number of selection systems may be used, including, but not limited, to the herpes simplex virus thymidine kinase (Wigler et al., 1977), hypoxanthine-guanine phosphoribosyltransferase (Szybalska et al., 1962) and adenine phosphoribosyltransferase genes (Lowy et al., 1980), in tk-, hgprt- or aprt-cells, respectively. Also, antimetabolite resistance may be used as the basis of selection for dhfr, that confers resistance to methotrexate (Wigler et al., 1980; O'Hare et al., 1981); gpt, that confers resistance to mycophenolic acid (Mulligan et al., 1981); neo, that confers resistance to the aminoglycoside G-418 (Colberre-Garapin et al., 1981); and hygro, that confers resistance to hygromycin.

It is contemplated that the isolated nucleic acids of the disclosure may be "overexpressed", i.e., expressed in increased levels relative to their natural expression in normal human cells, or even relative to the expression of other proteins in the recombinant host cell. Such overexpression may be assessed by a variety of methods, including radiolabeling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell and, e.g., visible on a gel.

4.4.2 Purification of Expressed Proteins

Further aspects of the present disclosure concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state, i.e., in this case, relative to its purity within a cell extract. A purified protein or peptide therefore also refers to a protein or peptide, free from the environment in which it may naturally occur.

Generally, "purified" refers to a protein or peptide composition which has been subjected to fractionation to remove various other components, and which composition substantially retains its expressed biological activity. Where the term "substantially purified" is used, this refers to a composition in which the protein or peptide forms the major component of the composition, such as constituting about 50% or more of the proteins in the composition.

Various methods for quantifying the degree of purification of the protein or peptide are known in the art. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, assessed by a "-fold purification number". The actual units used to represent the amount of activity is dependent upon the particular assay technique chosen to follow the purification and whether or not the expressed protein or peptide exhibits an enzymatic or other activity.

Various techniques suitable for use in protein purification are known in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that a protein or peptide always be provided in its most purified state. Indeed, it is contemplated that less substantially purified products have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus generally results in a greater-fold purification than the same technique utilizing a low pressure chromatography system. Methods exhibiting a lower degree of relative purification may have advantages in total recovery of protein product, or in maintaining the activity of an expressed protein.

It is known that the migration of a polypeptide may vary, sometimes significantly, with different conditions of SDS/PAGE (Capaldi et al., *Biochem. Biophys. Res. Comm.*, 76:425, 1977). It is therefore appreciated that under differing electrophoresis conditions, the apparent molecular weights of purified or partially purified expression products may vary.

4.4.3 Antibody Generation

For some embodiments, it is preferred to produce antibodies that bind with high specificity to the protein product (s) of an isolated nucleic acid of a sequence comprising SEQ ID NO:1, SEQ ID NO:2, SEQ ID NO:3, SEQ ID NO:29, SEQ ID NO:30, SEQ ID NO:34, SEQ ID NO:48 or SEQ ID NO:49. Means for preparing and characterizing antibodies are well known in the art (See, e.g., Antibodies: A Laboratory Manual, Cold Spring Harbor Laboratory, 1988).

Methods for generating polyclonal antibodies are well known in the art. Briefly, a polyclonal antibody is prepared by immunizing an animal with an immunogenic composition and collecting antisera from that immunized animal. A wide range of animal species may be used for the production of antisera, including rabbits, mice, rats, hamsters, guinea pigs or goats. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin may also be used as carriers. Means for conjugating a polypeptide to a carrier protein are well known in the art and include glutaraldehyde, m-maleimidobenzoyl-N-hydroxysuccinimide ester, carbodiimide and bisbiazotized benzidine.

As is also well known in the art, the immunogenicity of a particular immunogen composition may be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies with the nature of the immunogen as well as the animal used for immunization. A variety of routes may be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal may be bled and the serum isolated and stored, and/or the animal may be used to generate monoclonal antibodies. For production of rabbit polyclonal antibodies, the animal may be bled through an ear vein or alternatively by cardiac puncture. The removed blood is allowed to coagulate and then centrifuged to separate serum components from whole cells and blood clots. The serum may be used as is for various applications or else a particular antibody fraction may be purified by well-known methods, such as affinity chromatography using another antibody or a peptide bound to a solid matrix.

Monoclonal antibodies (MAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified expressed protein, polypeptide or peptide. The immunizing composition is administered in a manner effective to stimulate antibody producing cells, as described above.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60-61), but mice are preferred, with the BALB/c mouse being most preferred as this generally gives a higher percentage of stable fusions.

The animals are injected with antigen as described above. The antigen may be coupled to carrier molecules such as keyhole limpet hemocyanin if necessary. The antigen is typically mixed with adjuvant, such as Freund's complete or incomplete adjuvant. Booster injections with the same antigen typically occur at approximately two-week intervals.

Following immunization, somatic cells with the potential for producing antibodies, specifically B leukocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals are immunized and the spleen of the animal with the highest antibody titer is removed and the spleen leukocytes obtained by homogenizing the spleen with a syringe. Typically, a spleen from an immunized mouse contains approximately $5 \times 10^7$ to $2 \times 10^8$ leukocytes.

The antibody-producing B leukocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in selective media which support the growth of only the desired fused cells (hybridomas).

Any one of a number of myeloma cells may be used, as are known in the art (Goding, pp. 65-66, 1986; Campbell, pp. 75-83, 1984). For example, where the immunized animal is a mouse, one may use P3-X63/Ag8, X63-Ag8.653, NS1/1.Ag 41, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71-74, 1986).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells may operate this pathway, but they have a limited life span in culture and generally die within about two weeks. Therefore, the only cells that may survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas are then serially diluted and cloned into individual antibody-producing cell lines, which clones may then be propagated indefinitely to provide MAbs. The cell lines may be exploited for MAb production in two basic ways. A sample of the hybridoma may be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, may then be tapped to provide MAbs in high concentration. The individual cell lines may also be cultured in vitro, where the MAbs are naturally secreted into the culture medium from which they may be readily obtained in high concentrations. MAbs produced by either means may be further purified as needed, using filtration, centrifugation and various chromatographic methods such as HPLC or affinity chromatography.

Large amounts of the monoclonal antibodies of the present disclosure may also be obtained by multiplying hybridoma cells in vivo. Cell clones are injected into mammals which are histocompatible with the parent cells, e.g., syngeneic mice, to cause growth of antibody-producing tumors. Optionally, the animals are primed with a hydrocarbon, especially oils such as pristane (tetramethylpentadecane) prior to injection.

In accordance with the present invention, fragments of monoclonal antibodies may be obtained by methods which include digestion of monoclonal antibodies with enzymes such as pepsin or papain and/or cleavage of disulfide bonds by chemical reduction. Alternatively, monoclonal antibody fragments encompassed by the present disclosure may be synthesized using an automated peptide synthesizer.

The monoclonal conjugates of the present disclosure are prepared by methods known in the art, e.g., by reacting a monoclonal antibody prepared as described above with, for instance, an enzyme in the presence of a coupling agent such as glutaraldehyde or periodate. Conjugates with fluorescein markers are prepared in the presence of these coupling agents or by reaction with an isothiocyanate. Conjugates with metal chelates are similarly produced. Other moieties to which antibodies may be conjugated include radionuclides such as $^3$H, $^{125}$I, $^{131}$I $^{32}$P, $^{35}$S, $^{14}$C, $^{51}$Cr, $^{36}$Cl, $^{57}$Co, $^{58}$Co, $^{59}$Fe, $^{75}$Se, $^{152}$Eu, and $^{99m}$Tc, or other useful labels which may be conjugated to antibodies. Radioactively labeled monoclonal antibodies of the present disclosure are produced according to well-known methods in the art. For instance, monoclonal antibodies may be iodinated by contact with sodium or potassium iodide and a chemical oxidizing agent such as sodium hypochlorite, or an enzymatic oxidizing agent, such as lactoperoxidase. Monoclonal antibodies according to the disclosure may be labeled with technetium$^{99}$ by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as $SNCl_2$, a buffer solution such as sodium-potassium phthalate solution, and the antibody.

It will be appreciated that monoclonal or polyclonal antibodies specific for proteins that are preferentially expressed in the peripheral blood of individuals with the disease state have utilities in several types of applications. These may include the production of diagnostic kits for use in detecting or diagnosing the disease state. It will be recognized that such uses are within the scope of the present invention.

4.5 Immunodetection Assays

4.5.1 Immunodetection Methods

In still further embodiments, the present disclosure concerns immunodetection methods for binding, purifying, removing, quantifying or otherwise generally detecting biological components. The encoded proteins or peptides of the present disclosure may be employed to detect antibodies having reactivity therewith, or, alternatively, antibodies prepared in accordance with the present invention, may be employed to detect the encoded proteins or peptides. The steps of various useful immunodetection methods have been described in the scientific literature, such as, e.g., Nakamura et al. (1987).

In general, the immunobinding methods include obtaining a sample suspected of containing a protein, peptide or antibody, and contacting the sample with an antibody or protein or peptide in accordance with the present invention, as the case may be, under conditions effective to allow the formation of immunocomplexes.

The immunobinding methods include methods for detecting or quantifying the amount of a reactive component in a sample, which methods require the detection or quantitation of any immune complexes formed during the binding process. Here, one obtains a sample suspected of containing a disease state-marker encoded protein, peptide or a corresponding antibody, and contacts the sample with an antibody or encoded protein or peptide, as the case may be, and then detects or quantifies the amount of immune complex formed under the specific conditions.

In terms of antigen detection, the biological sample analyzed would ordinarily consist of peripheral blood. However, it may be any sample that is suspected of containing a disease state-specific antigen, such as a lymph node tissue section or specimen, a homogenized tissue extract, an isolated cell, a cell membrane preparation, separated or purified forms of any of the above protein-containing compositions, or any other biological fluid that comes into contact with diseased tissues, including lymphatic fluid, urine and even seminal fluid.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any antigens present. After this time, the sample-antibody composition, such as a tissue section, ELISA plate, dot blot or Western blot, is generally washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of conventional use in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The encoded protein, peptide or corresponding antibody employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

The immunodetection methods of the present disclosure have evident utility in the diagnosis of human disease states. A biological or clinical sample suspected of containing either the encoded protein or peptide or corresponding antibody is used. However, these embodiments also have applications to non-clinical samples, such as in the titering of antigen or antibody samples, in the selection of hybridomas, and the like.

In the clinical diagnosis or monitoring of patients with a disease state, the detection of an antigen encoded by a disease state marker nucleic acid, or an increase in the levels of such an antigen, in comparison to the levels in a corresponding biological sample from a normal subject is indicative of a patient with the disease state. The basis for such diagnostic methods lies, in part, with the finding that the nucleic acid disease state markers identified in the present disclosure are overexpressed in peripheral blood samples from individuals with the disease state (see Examples 1 through 5 below). By extension, it may be inferred that at least some of these markers produce elevated levels of encoded proteins, that may also be used as disease state markers.

Methods of differentiating between significant expression of a biomarker, which represents a positive identification, and low level or background expression of a biomarker are well known in the art. Background expression levels are often used to form a "cut-off" above which increased staining is scored as significant or positive. Significant expression may be represented by high levels of antigens in tissues or within body fluids, or alternatively, by a high proportion of cells from within a tissue that each give a positive signal.

4.5.2 Immunohistochemistry

The antibodies of the present disclosure may also be used in conjunction with both fresh-frozen and formalin-fixed, paraffin-embedded tissue blocks prepared from study by immunohistochemistry (IHC) or fixed cells on microscope slides for immunocytochemistry. The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25-50 serial sections containing an average of about 500 intact cells.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

4.5.3 Flow Cytometry

Expressed proteins may also be detected by flow cytometry as described in Fujishima et al, 1996. In the practice of the method, the cells are fixed and then incubated with a monoclonal antibody against the expressed protein to be detected. The bound antibodies are then contacted with labeled anti-IgG for example for detection. A typical label is FITC. The fluorescent intensity may then be measured by flow cytometer such as Ortho Cytron, Ortho diagnostics, or FACScan; Becton Dickinson.

FACS permits the separation of sub-populations of cells initially on the basis of their light scatter properties as they pass through a laser beam. The forward light scatter (FALS) is related to cell size and the right angle light scatter to cell density, cell contour and nucleo-cytoplasmic ratio. Since cells are tagged with fluorescent labeled antibody they can then be further characterized by fluorescence intensity and positive and negative windows set on the FACS to collect bright fluorescence and low fluorescence cells. Cells are sorted at a flow rate of about 3000 cells per second and collected in positive and negative cells.

4.5.4 ELISA

As noted, it is contemplated that the encoded proteins or peptides of the disclosure have utility as immunogens, e.g., in connection with vaccine development, in immunohistochemistry and in ELISA assays. One evident utility of the encoded antigens and corresponding antibodies is in immunoassays for the detection of disease state marker proteins, as needed in diagnosis and prognostic monitoring.

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it is readily appreciated that detection is not limited to such techniques, and Western blotting, dot blotting, FACS analyses, and the like may also be used.

In one exemplary ELISA, antibodies binding to the encoded proteins of the disclosure are immobilized onto a selected surface exhibiting protein affinity, such as a well in a polystyrene microtiter plate. Then, a test composition suspected of containing the disease state marker antigen, such as a clinical sample, is added to the wells. After binding and washing to remove non-specifically bound immunecomplexes, the bound antigen may be detected. Detection is generally achieved by the addition of a second antibody specific for the target protein, that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the disease state marker antigen are immobilized onto the well surface and then contacted with the antibodies of the invention. After binding and washing to remove non-specifically bound immunecomplexes, the bound antigen is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Another ELISA in which the proteins or peptides are immobilized, involves the use of antibody competition in the detection. In this ELISA, labeled antibodies are added to the wells, allowed to bind to the disease state marker protein, and detected by means of their label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and reduces the amount of antigen available to bind the labeled antibodies.

Irrespective of the format employed, ELISAs have certain features in common, such as coating, incubating or binding, washing to remove non-specifically bound species, and detecting the bound immunecomplexes. These are described as follows:

In coating a plate with either antigen or antibody, it is typical to incubate the wells of the plate with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is more customary to use a secondary or tertiary detection means rather than a direct procedure. Thus, after binding of a protein or antibody to the well, coating with a non-reactive material to reduce background, and washing to remove unbound material, the immobilizing surface is contacted with the control and/or clinical or biological sample to be tested under conditions effective to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand.

"Under conditions effective to allow immunecomplex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody has an associated label to allow detection. Preferably, this is an enzyme that generates color development upon incubating with an appropriate chromogenic substrate. Thus, for example, one may contact and incubate the first or second immunecomplex with a urease, glucose oxidase, alkaline phosphatase or hydrogen peroxidase-conjugated antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl)-benzthiazoline-6-sulfonic acid [ABTS] and $H_2O_2$, in the case of peroxidase as the enzyme label. Quantitation is then achieved by measuring the degree of color generation, e.g., using a spectrophotometer.

4.5.5 Use of Antibodies for Radioimaging

The antibodies of this disclosure are used to quantify and localize the expression of the encoded marker proteins. The antibody, for example, may be labeled by any one of a variety of methods and used to visualize the localized concentration of the cells producing the encoded protein.

A radionuclide may be bound to an antibody either directly or indirectly by using an intermediary functional group. Intermediary functional groups which are often used to bind radioisotopes which exist as metallic ions to antibody are diethylenetriaminepentaacetic acid (DTPA) and ethylene diaminetetraacetic acid (EDTA). Examples of metallic ions suitable for use in this disclosure are $^{99m}Tc$, $^{123}I$, $^{131}I$ $^{111}In$, $^{97}Ru$, $^{67}Cu$, $^{67}Ga$, $^{125}I$, $^{68}Ga$, $^{72}As$, $^{89}Zr$, and $^{201}Tl$.

In accordance with this disclosure, the monoclonal antibody or figment thereof may be labeled by any of several techniques known to the art. The methods of the present disclosure may also use paramagnetic isotopes for purposes of in vivo detection. Elements particularly useful in Magnetic Resonance Imaging ("MRI") include $^{157}Gd$, $^{55}Mn$, $^{162}Dy$, $^{52}Cr$, and $^{56}Fe$.

Administration of the labeled antibody may be local or systemic and accomplished intravenously, intraarterially, via the spinal fluid or the like. Administration may also be intradermal or intracavitary, depending upon the body site under examination. After a sufficient time has lapsed for the monoclonal antibody or fragment thereof to bind with the diseased tissue, for example 30 minutes to 48 hours, the area of the subject under investigation is examined by routine imaging techniques such as MRI, SPECT, planar scintillation imaging and emerging imaging techniques, as well. The exact protocol necessarily varies depending upon factors specific to the patient, as noted above, and depending upon the body site under examination, method of administration and type of label used. The determination of specific procedures is routine in the art. The distribution of the bound radioactive isotope and its increase or decrease with time is then monitored and recorded. By comparing the results with data obtained from studies of clinically normal individuals, the presence and extent of the diseased tissue may be determined.

The instant disclosure addresses detection of disease state cells by their effect on gene expression in immune system leukocytes. In early stages of the disease state, such immune response may be localized. For example, the response may be limited to lymph nodes immediately surrounding a metastasizing tumor or other localized form of a disease state. Localization of differentially expressed disease state markers may be of utility for separating disease states of widespread distribution from those of limited distribution within the patient. Such a detection means is therefore of significance in the management and care of patients with the disease state. It will be recognized that this utility is included within the scope of the present disclosure.

4.5.6 Kits

In still further embodiments, the present disclosure concerns immunodetection kits for use with the immunodetection methods described above. As the encoded proteins or peptides may be employed to detect antibodies and the corresponding antibodies may be employed to detect encoded proteins or peptides, either or both of such components may be provided in the kit. The immunodetection kits thus comprise, in suitable container means, an encoded protein or peptide, or a first antibody that binds to an encoded protein or peptide, and an immunodetection reagent.

In certain embodiments, the encoded protein or peptide, or the first antibody that binds to the encoded protein or peptide, may be bound to a solid support, such as a column matrix or well of a microtiter plate.

The immunodetection reagents of the kit may take any one of a variety of forms, including those detectable labels that are associated with or linked to the given antibody or antigen, and detectable labels that are associated with or attached to a secondary binding ligand. Exemplary secondary ligands are those secondary antibodies that have binding affinity for the first antibody or antigen, and secondary antibodies that have binding affinity for a human antibody.

Further suitable immunodetection reagents for use in the present kits include the two-component reagent that comprises a secondary antibody that has binding affinity for the first antibody or antigen, along with a third antibody that has binding affinity for the second antibody, the third antibody being linked to a detectable label.

The kits may further comprise a suitably aliquoted composition of the encoded protein or polypeptide antigen, whether labeled or unlabeled, as may be used to prepare a standard curve for a detection assay.

The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits generally includes at least one vial, test tube, flask, bottle, syringe or other container means, into which the antibody or antigen may be placed, and preferably, suitably aliquoted. Where a second or third binding ligand or additional component is provided, the kit also generally contains a second, third or other additional container into which this ligand or component may be placed. The kits of the present disclosure also typically include a means for containing the antibody, antigen, and any other reagent containers in close confinement for commercial sale. Such containers may include injection or blow-molded plastic containers into which the desired vials are retained.

4.6 Detection and Quantitation of RNA Species

One embodiment of the instant disclosure comprises a method for identification of a disease state in a biological sample by amplifying and detecting nucleic acids corresponding to disease state markers. The biological sample may be any tissue or fluid in which leukocyte cells might be present. Various embodiments include bone marrow aspirate, bone marrow biopsy, lymph node aspirate, lymph node biopsy, spleen tissue, fine needle aspirate, skin biopsy or organ tissue biopsy. Other embodiments include samples of body fluid such as peripheral blood, lymph fluid, ascites, serous fluid, pleural effusion, sputum, cerebrospinal fluid, lacrimal fluid, stool or urine.

Nucleic acid used as a template for amplification is isolated from cells contained in the biological sample, according to conventional methodologies. (Sambrook et al., 1989) The nucleic acid may be genomic DNA or fractionated or whole cell RNA. Where RNA is used, it may be desired to convert the RNA to a complementary cDNA. In one embodiment, the RNA is whole cell RNA and is used directly as the template for amplification.

Pairs of primers that selectively hybridize to nucleic acids corresponding to disease state-specific markers are contacted with the isolated nucleic acid under conditions that permit selective hybridization. Once hybridized, the nucleic acid: primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology; Bellus, 1994).

Following detection, one may compare the results seen in a given patient with statistically significant reference groups of normal individuals and patients with the disease state. In this way, it is possible to correlate the amount of marker detected with various clinical states.

4.6.1 Primers

The term primer, as defined herein, is meant to encompass any nucleic acid that is capable of priming the synthesis of a nascent nucleic acid in a template-dependent process.

Typically, primers are oligonucleotides from ten to twenty base pairs in length, but longer sequences may be employed. Primers may be provided in double-stranded or single-stranded form, although the single-stranded form is preferred.

4.6.2 Template Dependent Amplification Methods

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety.

Briefly, in PCR, two primer sequences are prepared which are complementary to regions on opposite complementary strands of the marker sequence. An excess of deoxynucleoside triphosphates is added to a reaction mixture along with a DNA polymerase, e.g., Taq polymerase. If the marker sequence is present in a sample, the primers bind to the marker and the polymerase causes the primers to be extended along the marker sequence by adding on nucleotides. By raising and lowering the temperature of the reaction mixture, the extended primers dissociate from the marker to form reaction products, excess primers bind to the marker and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641 filed Dec. 21, 1990. Polymerase chain reaction methodologies are well known in the art.

Alternatively, RNA species can be quantitated by means that do not necessarily require amplification by PCR. These means may include other amplification techniques, for example, isothermic amplification techniques such as the one developed by Gen-Probe (San Diego, Calif.), and the ligase chain reaction ("LCR"), disclosed in EPA No. 320 308, incorporated herein by reference in its entirely. In LCR, two complementary probe pairs are prepared, and in the presence of the target sequence, each pair binds to opposite complementary strands of the target such that they abut. In the presence of a ligase, the two probe pairs link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA which has a region complementary to that of a target is added to a sample in the presence of an RNA polymerase. The polymerase copies the replicative sequence which may then be detected.

An isothermal amplification method, in which restriction endonucleases and ligases are used to achieve the amplification of target molecules that contain nucleoside 5'-[alpha-thio]-triphosphates in one strand of a restriction site may also be useful in the amplification of nucleic acids in the present invention. Walker et al., *Proc. Nat'l Acad. Sci. USA* 89:392-396 (1992), incorporated herein by reference in its entirety.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases may be added as biotinylated derivatives for easy detection. A similar approach is used in SDA. Target specific sequences may also be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated.

Other amplification methods are described in GB Application No. 2 202 328, and in PCT Application No. PCT/US89/01025, each of which is incorporated herein by reference in its entirety, may be used in accordance with the present invention. In the former application, "modified" primers are used in a PCR like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR. Kwoh et al., *Proc. Nat'l Acad. Sci. USA* 86:1173 (1989); Gingeras et al., PCT Application WO 88/10315, incorporated herein by reference in their entirety. In NASBA, the nucleic acids may be prepared for amplification by conventional phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate target specific sequences.

Davey et al., EPA No. 329 822 (incorporated herein by reference in its entirely) disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence may be used by the appropriate RNA polymerase to make many RNA copies of the DNA. These copies may then re-enter the cycle leading to very swift amplification. With proper choice of enzymes, this amplification may be done isothermally without addition of enzymes at each cycle. Because of the cyclical nature of this process, the starting sequence may be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR." Frohman, M. A., In: *PCR PROTOCOLS: A GUIDE TO METHODS AND APPLICATIONS*, Academic Press, N.Y. (1990) and Ohara et al., *Proc. Nat'l Acad. Sci. USA*, 86:5673-5677 (1989), each herein incorporated by reference in their entirety.

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., *Genomics* 4:560 (1989), incorporated herein by reference in its entirety.

An example of a technique that does not require nucleic acid amplification, that can also be used to quantify RNA in some applications is a nuclease protection assay. There are many different versions of nuclease protection assays known to those practiced in the art. The characteristic that all versions of nuclease protection assays share in common is that they involve hybridization of an antisense nucleic acid with the RNA to be quantified. The resulting hybrid double stranded molecule is then digested with a nuclease that digests single stranded nucleic acids more efficiently than double stranded molecules. The amount of antisense nucleic acid that survives digestion is a measure of the amount of the target RNA species to be quantified. An example of a nuclease protection assay that is commercially available is the RNase protection assay manufactured by Ambion, Inc. (Austin, Tex.).

4.6.3 Separation Methods

Following amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using conventional methods. See Sambrook et al., 1989.

Alternatively, chromatographic techniques may be employed to effect separation. There are many kinds of chromatography which may be used in the present invention: adsorption, partition, ion-exchange and molecular sieve, HPLC, and many specialized techniques for using them including column, paper, thin-layer and gas chromatography (Freifelder, 1982).

Another example of a separation methodology is done by covalently labeling the oligonucleotide primers used in a PCR reaction with various types of small molecule ligands. In one such separation, a different ligand is present on each oligonucleotide. A molecule, perhaps an antibody or avidin if the ligand is biotin, that specifically binds to one of the ligands is used to coat the surface of a plate such as a 96 well ELISA plate. Upon application of the PCR reactions to the surface of such a prepared plate, the PCR products are bound with specificity to the surface. After washing the plate to remove unbound reagents, a solution containing a second molecule that binds to the first ligand is added. This second molecule is linked to some kind of reporter system. The second molecule only binds to the plate if a PCR product has been produced whereby both oligonucleotide primers are incorporated into the final PCR products. The amount of the PCR product is then detected and quantified in a commercial plate reader much as ELISA reactions are detected and quantified. An ELISA-like system such as the one described here has been developed by the Raggio Italgene company under the C-Track trade name.

4.6.4 Identification Methods

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products may then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, where the other member of the binding pair carries a detectable moiety.

In one embodiment, detection is by Southern blotting and hybridization with a labeled probe. The techniques involved in Southern blotting are well known to those of skill in the art and may be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

4.6.5 Kit Components

All the essential materials and reagents required for detecting disease state markers in a biological sample may be assembled together in a kit. This generally comprises preselected primers for specific markers. Also included may be enzymes suitable for amplifying nucleic acids including various polymerases (RT, Taq, etc.), deoxynucleotides and buffers to provide the necessary reaction mixture for amplification.

Such kits generally comprise, in suitable means, distinct containers for each individual reagent and enzyme as well as for each marker primer pair. Preferred pairs of primers for amplifying nucleic acids are selected to amplify the sequences specified in SEQ ID NO:1, SEQ ID NO:2, SEQ ID NO:3, SEQ ID NO:29, SEQ ID NO:30, SEQ ID NO:34, SEQ ID NO:48 and SEQ ID NO:49.

In another embodiment, such kits comprise hybridization probes specific for disease state markers, chosen from a group including nucleic acids corresponding to the sequences specified SEQ ID NO:1, SEQ ID NO:2, SEQ ID NO:3, SEQ ID NO:29, SEQ ID NO:30, SEQ ID NO:34, SEQ ID NO:48 or SEQ ID NO:49. Such kits generally comprise, in suitable means, distinct containers for each individual reagent and enzyme as well as for each marker hybridization probe.

4.7 Use of RNA Fingerprinting to Identify Markers of Human Disease

RNA fingerprinting is a means by which RNAs isolated from many different tissues, cell types or treatment groups may be sampled simultaneously to identify RNAs whose relative abundances vary. Two forms of this technology were developed simultaneously and reported in 1992 as RNA fingerprinting by differential display (Liang and Pardee, 1992; Welsh et al., 1992). (See also Liang and Pardee, U.S. Pat. No. 5,262,311, incorporated herein by reference in its entirety.) Some of the studies described herein were performed similarly to Donahue et al., J. Biol. Chem. 269: 8604-8609, 1994.

All forms of RNA fingerprinting by PCR are theoretically similar but differ in their primer design and application. The most striking difference between differential display and other methods of RNA fingerprinting is that differential display utilizes anchoring primers that hybridize to the poly A tails of mRNAs. As a consequence, the PCR products amplified in differential display are biased towards the 3' untranslated regions of mRNAs.

The basic technique of differential display has been described in detail (Liang and Pardee, 1992). Total cell RNA is primed for first strand reverse transcription with an anchoring primer composed of oligo dT. The oligo dT primer is extended using a reverse transcriptase, for example, Moloney Murine Leukemia Virus (MMLV) reverse transcriptase. The synthesis of the second strand is primed with an arbitrarily chosen oligonucleotide, using reduced stringency conditions. Once the double-stranded cDNA has been synthesized, amplification proceeds by conventional PCR techniques, utilizing the same primers. The resulting DNA fingerprint is analyzed by gel electrophoresis and ethidium bromide staining or autoradiography. A side by side comparison of fingerprints obtained from different cell derived RNAs using the same oligonucleotide primers identifies mRNAs that are differentially expressed.

RNA fingerprinting technology has been demonstrated as being effective in identifying genes that are differentially expressed in cancer cells (Liang et al., 1992; Wong et al., 1993; Sager et al., 1993; Mok et al., 1994; Watson et al., 1994; Chen et al., 1995; An et al., 1995). The present disclosure utilizes the RNA fingerprinting technique or other techniques described herein to identify genes that are differentially expressed in peripheral blood cells in human disease states.

4.7 Design and Theoretical Considerations for Relative Quantitative RT-PCR

Reverse transcription (RT) of RNA to cDNA followed by relative quantitative PCR (RT-PCR) may be used to determine the relative concentrations of specific mRNA species in a series of total cell RNAs isolated from peripheral blood of normal individuals and individuals with a disease state. By determining that the concentration of a specific mRNA species varies, it is shown that the gene encoding the specific mRNA species is differentially expressed. This technique may be used to confirm that mRNA transcripts shown to be differentially regulated by RNA fingerprinting are differentially expressed in disease state progression.

In PCR, the number of molecules of the amplified target DNA increase by a factor approaching two with every cycle of the reaction until some reagent becomes limiting. Thereafter, the rate of amplification becomes increasingly diminished until there is not an increase in the amplified target between cycles. If one plots a graph on which the cycle number is on the X axis and the log of the concentration of the amplified target DNA is on the Y axis, one observes that a curved line of characteristic shape is formed by connecting the plotted points. Beginning with the first cycle, the slope of the line is positive and constant. This is said to be the linear portion of the curve. After some reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR is directly proportional to the starting concentration of the target before the PCR was begun. By determining the concentration of the PCR products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived may be determined for the respective tissues or cells. This direct proportionality between the concentration of the PCR products and the relative mRNA abundances is only true in the linear range portion of the PCR reaction.

The final concentration of the target DNA in the plateau portion of the curve is determined by the availability of reagents in the reaction mix and is independent of the original concentration of target DNA. Therefore, the first condition that must be met before the relative abundances of a mRNA species may be determined by RT-PCR for a collection of RNA populations is that the concentrations of the amplified PCR products must be sampled when the PCR reactions are in the linear portion of their curves.

The second condition that must be met for an RT-PCR study to successfully determine the relative abundances of a particular mRNA species is that relative concentrations of the amplifiable cDNAs must be normalized to some independent standard. The goal of an RT-PCR study is to determine the abundance of a particular mRNA species relative to the average abundance of all mRNA species in the sample. In the studies described below, mRNAs for β-actin, asparagine synthetase and lipocortin II were used as external and internal standards to which the relative abundance of other mRNAs are compared.

Most protocols for competitive PCR utilize internal PCR standards that are approximately as abundant as the target. These strategies are effective if the products of the PCR amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons may be made between RNA samples.

The discussion above describes the theoretical considerations for an RT-PCR assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR is performed as a relative quantitative RT-PCR with an internal standard in which the internal standard is an amplifiable cDNA fragment that is larger than the target cDNA fragment and in which the abundance of the mRNA encoding the internal standard is roughly 5-100 fold higher than the mRNA encoding the target. This assay measures relative abundance, not absolute abundance of the respective mRNA species.

Other studies may be performed using a more conventional relative quantitative RT-PCR with an external standard protocol. These assays sample the PCR products in the linear portion of their amplification curves. The number of PCR cycles that are optimal for sampling must be empirically determined for each target cDNA fragment. In addition, the reverse transcriptase products of each RNA population isolated from the various tissue samples must be carefully normalized for equal concentrations of amplifiable cDNAs. While empirical determination of the linear range of the amplification curve and normalization of cDNA preparations are tedious and time consuming processes, the resulting RT-PCR assays may, in certain cases, be superior to those derived from a relative quantitative RT-PCR with an internal standard.

One reason for this is that without the internal standard/competitor, all of the reagents may be converted into a single PCR product in the linear range of the amplification curve, increasing the sensitivity of the assay. Another reason is that with only one PCR product, display of the product on an electrophoretic gel or some other display method becomes less complex, has less background and is easier to interpret.

4.8 Diagnosis and Prognosis of Human Cancer

In certain embodiments, the present disclosure enables the diagnosis and prognosis of human cancer by screening for marker nucleic acids. Various markers have been proposed to be correlated with metastasis and malignancy. They may be classified generally as cytologic, protein or nucleic acid markers.

Cytologic markers include such things as "nuclear roundedness" (Diamond et al., 1982) and cell ploidy. Protein markers include prostate specific antigen (PSA) and CA125.

Nucleic acid markers have included amplification of Her2/neu, point mutations in the p53 or ras genes, and changes in the sizes of triplet repeat segments of particular chromosomes.

All of these markers exhibit certain drawbacks, associated with false positives and false negatives. A false positive result occurs when an individual without malignant cancer exhibits the presence of a "cancer marker". For example, elevated serum PSA has been associated with prostate carcinoma. However, it also occurs in some individuals with non-malignant, benign hyperplasia of the prostate. A false negative result occurs when an individual actually has cancer, but the test fails to show the presence of a specific marker. The incidence of false negatives varies for each marker, and frequently also by tissue type. For example, ras point mutations have been reported to range from a high of 95 percent in pancreatic cancer to a low of zero percent in some gynecologic cancers.

Additional problems arise when a marker is present only within the transformed cell itself. Ras point mutations may only be detected within the mutant cell, and are apparently not present in, for example, the serum or urine of individuals with ras-activated carcinomas. This means that, in order to detect a malignant tumor, one must take a sample of the tumor itself, or its metastatic cells. Essentially one must first identify and sample a tumor before the presence of the cancer marker may be detected.

Finally, specific problems occur with markers that are present in normal cells but absent in cancer cells. Most tumor samples contain mixed populations of both normal and transformed cells. If one is searching for a marker that is present in normal cells, but occurs at reduced levels in transformed cells, the "background" signal from the normal cells in the sample may mask the presence of transformed cells.

The ideal disease state marker would be one that is present in individuals with the disease state, and either missing or expressed at significantly lower levels in normal individuals. The present disclosure addresses this need, in the case of metastatic prostate cancer for example, by identifying several new nucleic acid markers that are expressed at higher levels in individuals with metastatic prostate cancer than in normal individuals. In particular, the results for markers UC302 (SEQ ID NO:1), UC325 (SEQ ID NO:2), UC331 (SEQ ID NO:29), and UC332 (SEQ ID NO:34) are quite promising in that these markers are apparently only overexpressed in the peripheral blood of individuals with metastatic tumors and are present at relatively low levels in normal individuals.

Further, since the markers are present in the whole blood of individuals with the disease state, the present detection method avoids the problem of having to suspect a tumor is in place before it may be sampled. The instant disclosure has utility as a general screening tool for asymptomatic individuals, as well as a means of differentially diagnosing those patients whose tumors have already metastasized. Depending upon the type of tumor involved, such individuals may be selected for systemic forms of anti-cancer therapy rather than surgical removal of localized tumor masses. Certain individuals with advanced forms of highly malignant metastatic tumors may be optimally treated by pain management alone.

It is anticipated that in clinical applications, human tissue samples will be screened for the presence of the disease state markers identified herein. Such samples would normally consist of peripheral blood, but may also consist of needle biopsy cores or lymph node tissue. In certain embodiments, nucleic acids would be extracted from these samples and amplified as described above. Some embodiments would utilize kits containing pre-selected primer pairs or hybridization probes. The amplified nucleic acids would be tested for the markers by, for example, gel electrophoresis and ethidium bromide staining, or Southern blotting, or a solid-phase detection means as described above. These methods are well known within the art. The levels of selected markers detected would be compared with statistically valid groups of individuals with metastatic, non-metastatic malignant, or benign tumors or normal individuals. The diagnosis and prognosis of the individual patient would be determined by comparison with such groups.

Another embodiment of the present disclosure involves application of RT-PCR techniques to detect a disease state using probes and primers selected from sequences comprising SEQ ID NO:1, SEQ ID NO:2, SEQ ID NO:3, SEQ ID NO:29, SEQ ID NO:30, SEQ ID NO:34, SEQ ID NO:48 and SEQ ID NO:49. Similar techniques have been described in PCT Patent Application No. WO 94/10343, incorporated herein by reference.

In this embodiment, the disease state is detected in hematopoietic samples by amplification of disease state-specific nucleic acid sequences. Samples taken from blood or lymph nodes are treated as described below to purify total cell RNA. The isolated RNA is reverse transcribed using a reverse transcriptase and primers selected to bind under high stringency conditions to a nucleic acid sequence from a group comprising SEQ ID NO:1, SEQ ID NO:2, SEQ ID NO:3, SEQ ID NO:29, SEQ ID NO:30, SEQ ID NO:34, SEQ ID NO:48 and SEQ ID NO:49. Following reverse transcription, the resulting cDNAs are amplified using conventional PCR techniques and a thermostable DNA polymerase.

The presence of amplification products corresponding to disease state-marker nucleic acids may be detected by several alternative means. In one embodiment, the amplification product may be detected by gel electrophoresis and ethidium bromide staining. Alternatively, following the gel electrophoresis step the amplification product may be detected by conventional Southern blotting techniques, using an hybridization probe selected to bind specifically to a disease state-marker nucleic acid sequence. Probe hybridization may in turn be detected by a conventional labeling means, for example, by incorporation of $[^{32}P]$-nucleotides followed by autoradiography. The amplification products may alternatively be detected using a solid phase detection system such as those utilizing a disease state-marker specific hybridization probe and an appropriate labeling means, or even the ELISA-like system known as C-track™ as described above.

The following examples are included to demonstrate preferred embodiments of the invention. It should be appreciated by those of skill in the art that the techniques disclosed in the examples which follow represent techniques discovered by the inventors to function well in the practice of the invention, and thus may be considered to constitute preferred modes for its practice. However, those of skill in the art should, in light of the present disclosure, appreciate that many changes may be made in the particular embodiments which are disclosed and still obtain a like or similar result without departing from the spirit and scope of the invention.

4.9 Materials and Methods

4.9.1 Application of RNA Fingerprinting to Discover Biomarkers for Disease States RNA fingerprinting (according to Liang and Pardee, 1992; Welsh et al., 1992; Liang and Pardee, 1993) was applied to nucleic acids isolated from the peripheral blood of individuals with metastatic prostate cancer, compared with normal individuals.

Blood was drawn from cancer patients and normal individuals into Vacutainer CPT tubes with ficoll gradients (Becton Dickinson and Company, Frankin Lanes, N.J.). The tubes were centrifuged to separate the red blood cells from various types of nucleated cells, collectively referred to as the buffy coat, and from blood plasma. Total cell RNA was isolated from the buffy coats by the RNA STAT-60 method (Tel-Test, Inc., Friendswood, Tex.). After RNA isolation, the nucleic acids were precipitated with ethanol. The precipitates were pelleted by centrifugation and redissolved in water. The redissolved nucleic acids were then digested with RNase-free DNase I (Boehringer Mannheim, Inc.) following the manufacturer's instructions, followed by organic extraction with phenol:chloroform:isoamylalcohol (25:24:1) and re-precipitation with ethanol.

The DNase I treated RNA was then pelleted by centrifugation and redissolved in water. The purity and concentration of the RNA in solution was estimated by determining optical density at wave lengths of 260 nm and 280 nm (Sambrook et al., 1989). The RNA was then examined by electrophoresis on a native TAE agarose gel (Sambrook et al., 1989) to determine its integrity. The RNA was then divided into three aliquots. One aliquot was set aside for relative quantitative RT-PCR confirmation using the external standard method described below.

A second aliquot was used to fingerprint the RNA by converting the RNA to first strand cDNA using random hexamers and reverse transcriptase; fingerprinting the cDNA by PCR using arbitrarily chosen oligonucleotides, (10 nucleotides in length); displaying the resulting PCR amplified products on an agarose gel stained with ethidium bromide and cutting differentially appearing bands out of the gel. The excised bands were then cloned and sequenced.

The RNA of the third aliquot was pooled to make a pool of blood RNA from normal individuals and a pool of RNA from the blood of patients with metastatic prostate cancer. The pools were fingerprinted using the sequential pairwise method of arbitrarily primed PCR fingerprinting of RNA (McClelland et al., 1994, *Nucleic Acids Research* 22, 4419-4431, incorporated herein by reference) with several changes. For example, arbitrary oligonucleotides of 15 to 24 nucleotides were used with Taq polymerase, and one tenth of each first strand cDNA reaction in each arbitrarily primed PCR reaction. One hundred and 200 ng were used in each first strand cDNA synthesis, respectively. Certain genes disclosed herein were discovered by the sequential pairwise method.

4.9.2 Methods Utilized in the RNA Fingerprinting Technique

The second type of RNA fingerprinting studies performed more closely resembled the protocol of Welsh et al. (1992). This approach used a variation of the above as modified by the use of agarose gels and non-isotopic detection of bands by ethidium bromide staining (An et al., 1995). Total RNAs were isolated from peripheral blood samples as described (Chomczynski & Sacchi, 1987). Ten micrograms of total cellular RNAs were treated with 5 units of RNAse-free DNAse I (GIBCO/BRL) in 20 mM Tris-HCl (pH 8.4), 50 mM KCl, 2 mM $MgCl_2$, and 20 units of RNAse inhibitor (Boehringer Mannheim). After extraction with phenol/chloroform and ethanol precipitation, the RNAs were redissolved in DEPC-treated water.

Two µg of each total cell RNA sample was reverse transcribed into cDNA using randomly selected hexamer primers and MMLV reverse transcriptase (GIBCO/BRL). PCR was performed using one or two arbitrarily chosen oligonucleotide primers (10-12mers). PCR conditions were: 10 mM Tris-HCl (pH 8.3), 50 mM KCl, 1.5 mM $MgCl_2$, 50 mM dNTPs, 0.2 mM of primer(s), 1 unit of Taq DNA polymerase (GIBCO/BRL) in a final volume of 20 ml. The amplification parameters included 35 cycles of reaction with 30 sec denaturing at 94° C., 90 sec annealing at 40° C., and 60 sec extension at 72° C. A final extension at 72° C. was performed for 15 min. The resulting PCR products were resolved into a fingerprint by size separation by electrophoresis through 2% agarose gels in TBE buffer (Sambrook et al., 1989). The fingerprints were visualized by staining with ethidium bromide. No re-amplification was performed.

Differentially appearing PCR products, that might represent differentially expressed genes, were excised from the gel with a razor blade, purified from the agarose using the Geneclean kit (Bio 101, Inc.), eluted in water and cloned directly into plasmid vectors using the TA cloning strategy (Invitrogen, Inc., and Promega, Inc.). These products were not re-amplified after the initial PCR fingerprinting protocol.

4.9.3 Confirmation of Differential Expression by Relative Quantitative RT-PCR: Protocols for RT-PCR

4.9.3.1 Reverse Transcription

One to five µg of total cell RNA from each tissue sample was reverse transcribed into cDNA. Reverse transcription was performed with 400 units of MMLV reverse transcriptase (GIBCO/BRL) in the presence of 50 mM Tris-HCl (pH 8.3), 75 mM KCl, 3 mM $MgCl_2$, 10 mM DTT, 500 mM dNTP, 50 ng random hexamers per microgram of RNA, and 1 U/ml RNase inhibitor. The reaction volume was 60 µl. The reaction mixture was incubated at room temperature for 10 minutes, then at 37° C. for 50 minutes. After reverse transcription the enzyme was denatured by heating to 65° C. for 10 minutes. After heat denaturation the samples were diluted with water to a final volume of 300 µl.

RT-PCR was utilized to examine mRNAs for differential expression. The sequences of oligonucleotides used as primers to direct the amplification of the various cDNA fragments are presented in Table 5.

4.9.3.2 Relative Quantitative RT-PCR with an Internal Standard

The concentrations of the original total cell RNAs were determined by measurement of $OD_{260/280}$ (Sambrook et al., 1989) and confirmed by examination of ribosomal RNAs on ethidium bromide stained agarose gels. It is required that all quantitative PCR reactions be normalized for equal amounts of amplifiable cDNA after the reverse transcription is completed. One solution to this is to terminate the reactions by driving the PCR reactions into plateau phase. This approach was utilized in some studies because it is quick and efficient. Lipocortin II was used as the internal standard or competitor. These PCRs were set up as follows:

Reagents: 200 mM each dNTP, 200 nM each oligonucleotide primer, 1×PCR buffer (Boehringer Mannheim including 1.5 mM $MgCl_2$), 3 ml diluted cDNA, and 2.5 units of Taq DNA polymerase/100 ml of reaction volume.

Cycling parameters: 30 cycles of 94° C. for 1 min; 55° C. for 1 min; and 72° C. for two min. Thermocyclers were either the MJ research thermocycler or the Stratagene Robocycler.

4.9.3.3 Relative Quantitative RT-PCR with an External Standard

There are three problems with the relative quantitative RT-PCR strategy described above. First, the internal standard must be roughly 4-10 times more abundant than the target for this strategy to normalize the samples. Second, because most of the PCR products are templated from the more abundant internal standard, the assay is less than optimally sensitive. Third, the internal standard must be truly unvarying. The result is that while the strategy described above is fast, convenient and applicable to samples of varying quality, it lacks sensitivity to modest changes in abundances.

To address these issues, a normalization was performed using the β-actin mRNA as external standard. These PCR reactions were performed with sufficient cycles to observe the products in the linear range of their amplification curves. The intensities of the ethidium bromide stained bands were documented and quantified using the Is1000 imaging analysis system manufactured by the Alpha Innotech, Corp. The quantified data was then normalized for variations in the starting concentrations of amplifiable cDNA by comparing the quantified data from each study with that derived from a similar study which amplified a cDNA fragment copied from the β-actin mRNA.

4.9.4 Multivariate Analysis of Prostate Disease State

4.9.4.1 Specimen Collection

Blood specimens (8-10 mls) were collected by venipuncture into standard serum or serum-separating tubes (Becton-Dickinson), allowed to coagulate for 30 minutes at room temperature, and then centrifuged at low speed (1000×g) for 10 minutes. Some specimens sent were immediately frozen and shipped overnight by delivery courier. Others were collected, processed, frozen, and shipped on dry ice by overnight mail. Upon arrival, all specimens were stored at −20° C. Repeated freeze-thaw cycles were avoided.

4.9.4.2 Measurement of Free and Total PSA

Two commercially available assays were utilized to measure PSA concentrations, an IMMULITE solid-phase chemiluminescence-based assay to measure free PSA (Diagnostic Products Corp.; Los Angeles, Calif.), and the FDA approved assay from TOSOH (San Diego, Calif.) that utilizes an enzyme-conjugated monoclonal antibody and fluorescent substrate to measure total PSA. However, since two different instruments were utilized to measure the components of the f/t PSA ratio, the international reference standards for free and total PSA were utilized to calibrate both assays and calculate the "corrected" f/t PSA ratio (Stamey, 1995).

4.9.4.3 F/T PSA Reference Standards and Correction of F/T PSA Ratio

The corrected f/t PSA ratio was determined according to Marley et al., 1996. Reference standards for free and total PSA assays were purchased from the Stanford University Prostate Center and consisted of an equimolar mixture of 90% PSA-α-1-antichymotrypsin and 10% free-PSA (Stamey, 1995; Chen et al., 1995). All testing dilutions were performed with 1% bovine serum albumin (Fraction V; Sigma Chemical Co.) in 20 mM phosphate-buffered saline (PBS), pH 7.4. Expected concentrations of the reference standards, determined from molar extinction coefficients ($\epsilon$), were also provided.

Free and total PSA assays were standardized as follows. Based upon the mean of seven linear standard curve runs of the reference standards (Stamey, 1995), correlation factors for free and total PSA measurement were calculated. Slope (m) deviations were measured relative to the linear plot based upon the PSA molar extinction coefficients ($\epsilon$) of the reference standards. Since all curves passed through the origin, the correction factor for the free/total PSA ratio was calculated from the difference in slopes. Intra-assay coefficients of variation for free PSA (range=0-2.0 ng/ml) and total PSA (range=0-20.0 ng/ml) assays were 7% and 8%, respectively. The correction factors applied to the free and total PSA values were 1.19 and 0.83, respectively. For analysis purposes, only the f/t PSA ratio values were corrected.

The (TOSOH) total PSA assay reacted equally to the free and bound (PSA-ACT) forms of PSA. The (Immulite) free PSA assay system was unable to detect the bound fraction of PSA (PSA-ACT) below a concentration of 20 ng/ml. Antibodies for detecting both total and free PSA were unable to detect PSA covalently linked to α-2 macroglobulin (PSA-MG or occult PSA).

4.9.4.4 Statistical Methods

Differences in free and total serum PSA data between BPH and cancer samples were examined using the non-parametric statistical method of Wilcoxon rank-sum tests (Vollmer, 1996). The binary dependent variable assessed was the clinical outcome of BPH or CaP. Sensitivity, specificity and Receiver Operator Characteristics (ROC) Curves analyses were derived by Logistic regression modeling using the STATA™ software package (Stata Corporation, College Station, Tex.). Classification and Regression Tree (CART) analysis (CART v1.01, SYSTAT Inc., Evanston, Ill.), was used to determine the optimal cutoff for the serum assays as well as the logistic regression models (Breiman et al., 1984; Steinberg and Colla, 1992). The correlation values of the independent parameters were also determined using the STATA™ software package.

4.9.4.5 IL-8 Quantitation

A commercial IL-8 immunoassay kit was purchased for use in this study (IL-8 Solid Phase Immunoassay, Cat. #D8050, 96 well microtiter plate format, from R&D Systems, 614 McKinley Pl. NE; Minneapolis, Minn. 55413). Solutions consisted of wash buffer, substrate solution (color reagents A&B), calibrator diluent RD6Z, assay diluent RD1-8, stop solution and IL-8 stock solution (2000 pg/ml). To prepare the IL-8 standards, 500 μl of calibrator diluent RD6Z was pipetted into each of a series of dilution tubes. A serial dilution of the IL-8 stock solution (2000 pg/ml) was prepared to yield standards of the following concentrations: 1000, 500, 250, 125, 62.5, 31.2, 15.6, 7.8 pg/ml.

The manufacturer's recommended protocol was used to assay IL-8 concentrations. All reagents and samples were first brought to room temperature. The assay mixture contained in each well; 100 μl of assay diluent RD1-8, 50 μl of sample (or appropriate standard) and 100 μl of IL-8 conjugate. The wells were covered with the provided adhesive strip and samples were incubated for 3 hours at room temperature. Each assay well was aspirated and washed with wash buffer for a total of six washes. After the final wash, the plate was inverted onto a paper towel to wick up excess moisture. Then 200 μl of substrate solution was added to each assay well and incubated for 30 min at room temperature. Fifty μl of stop solution was added to each assay well and mixed by gentle tapping. Optical density was measured within 30 min of addition of stop solution, using a Bio-Tek EL-808 microplate reader (96 well format) at 450 nm.

4.9.4.6 IL-8 Standard Curve and Coefficient of Variation (CV)

The IL-8 standard curve consisted of eight concentrations: 1000, 500, 250, 125, 62.5, 31.2, 15.6, 7.8 pg IL-8/ml. The mean of six different measurements of each standard dilution was plotted (x-axis) vs. the mean optical density measured (y-axis). Results were plotted using the KC3 software package (Bio-Tek Instruments; Winooski, Vt.).

Coefficient of variation (CV): From the eight data points for each concentration of the standard curve, Coefficient of Variation (CV)=Standard Deviation/Mean was calculated to be 6.9, 6.4, 11.1, 10.1, 4.5, 4.4, 13.0 and 34.1%, respectively for the standard curve concentrations listed above. Points with a CV of greater than 13% were not utilized for this study.

4.10 IL-8

UC325-1 is derived from the IL-8 gene (Genbank Accession #M28130). UC325-1 and UC325-2, an alternatively spliced form that includes the third intron of the IL-8 primary transcript, are transcribed from the IL-8 gene. Our definition of IL-8 gene products means all mRNAs transcribed from the IL-8 gene, the polypeptides encoded by those mRNAs and their post-translationally processed protein products.

Those practiced in the art will realize that there exists naturally occurring genetic variation between individuals. As a result, some individuals may synthesize IL-8 gene products that differ from those described by the sequences entailed in the Genbank number listed above. We include in our definition of IL-8, those products encoded by IL-8 genes that vary in sequence from those described above. Those practiced in the art will realize that modest variations in DNA sequence will not significantly obscure the identity of a gene product as being derived from the IL-8 gene.

The following examples are included to demonstrate preferred embodiments of the invention. It should be appreciated by those of skill in the art that the techniques disclosed in the examples which follow represent techniques discovered by the inventors to function well in the practice of the invention, and thus may be considered to constitute preferred modes for its practice. However, those of skill in the art should, in light of the present disclosure, appreciate that many changes may be made in the particular embodiments which are disclosed and still obtain a like or similar result without departing from the spirit and scope of the invention.

4.11 Detection and Diagnosis of Metastatic Breast and Prostate Cancer

4.11.1 Preparation of RNA

Ten ml of peripheral blood was collected from healthy volunteers, patients with clinically and biopsy confirmed BPH, localized or advanced metastatic prostate cancer, or from patients with advanced metastatic breast cancer. Prostate and breast cancer patients with metastatic disease were selected that had failed a primary therapy and had evidence of recurrence of disease. The metastatic prostate cancer patients had high ($\geq$50 ng/ml) serum concentrations of PSA.

RNA was prepared from nucleated circulating peripheral blood cells as described in Section 4.9.1 above. For the PCR™ based applications of RNA fingerprinting and relative quantitative RT-PCR™, it is absolutely critical that the total RNA is completely free of genomic DNA. Typically, 5.0 to 10.0 µg of total RNA was digested with 20-40 units of RNase free DnaseI in 100-200 µl of reaction volume for 20 minutes at 37° C. Following digestion, the total RNAs were extracted with phenol (pH=4.3, Amresco, Inc., Solon, Ohio) and ethanol precipitated.

To confirm that the RNA was free of contaminating genomic DNA, 500 ng to 1.0 µg of each DNaseI treated RNA was resuspended in water. These samples were used as templates for PCR™ using oligonucleotide primers that anneal to exons 3 and 4 of the gene encoding PSA (exon 3: 5'-GCCTCAGGCTGGGGCAGCATT-3' (SEQ ID NO:15), exon 4: 5'-GGTCACCTTCTGAGGGTGAACTTGC-3' (SEQ ID NO:16)). These primers anneal to opposite strands of genomic DNA that flank the 145 bp intron 3 of the PSA gene. PCR™ was performed at 94° C. for 75 seconds, followed by 40 cycles of 94° C. for 45 seconds, 55° C. for 45 seconds, and 72° C. for 75 seconds, then a final extension of 72° C. for 5 minutes. RNA was considered DNA free if no PCR™ products could be visualized upon gel electrophoresis that co-migrated with the product derived from a positive control of known human genomic DNA. If PSA gene products were observed after PCR™, the RNA was redigested with DNaseI and analyzed again for contaminating genomic DNA. After it was confirmed that the RNAs were free of genomic DNA, 500 ng to 1.0 µg of RNA was electrophoresed on a 1.2% agarose Tris Acetate EDTA (TAE) gel to visualize the ribosomal RNAs (Sambrook et al., 1989). Only RNA preparations for which the 28S ribosomal RNA could be visualized were selected for further analysis by RNA fingerprinting and relative quantitative RT-PCR™.

4.11.2 RNA Fingerprinting

RNA fingerprinting with arbitrarily chosen oligonucleotide primers (Welsh et al., 1992) was performed as described in Section 4.9.2 above, except that the oligonucleotides of arbitrary sequence were used in a sequential pairwise strategy that optimizes the amount of mRNA complexity that can be surveyed with limited numbers of primers and starting RNA.

Two RNA pools were fingerprinted. Combining peripheral blood total RNA from five healthy individuals made one pool. Combining peripheral blood total RNA from five individuals with recurring metastatic prostate cancer similarly made another pool. Using the pooled RNAs as templates, first strand cDNA synthesis was primed by annealing an oligonucleotide of arbitrary sequence to the pooled RNAs at low stringency. All fingerprinting studies were performed in duplicate using different initial concentrations of template RNA. Replicate fingerprints were initiated by using either 75 ng or 150 ng of RNA as template during first strand cDNA synthesis. Reaction conditions for first strand cDNA synthesis were 250 units of SuperScript II™ (GIBCO-BRL) in 1x supplier's reaction buffer (25 mM Tris-HCl [pH=8.3], 37.5 mM KCl, 3.0 mM $MgCl_2$), 10 mM DTT, 400 µM each dNTP, and 2.0 µM arbitrary oligonucleotide in a 40 µl volume. The latter was incubated for 1 h at 37° C. Following first strand cDNA synthesis, the RNA was digested with RNase H and heat inactivated at 70° C. as directed by the supplier.

One-tenth (4.0 µl) of the first strand cDNA reaction mixture was used in the fingerprinting PCR™ reaction. As many as ten different RNA fingerprints were generated from each first strand cDNA reaction. To the first strand cDNA was added 36 µl of a PCR™ mix solution. The latter contained 50 mM Tris-Cl (pH=8.3), 50 mM KCl, 200 µM each dNTP, 1.0/µl µCi of $\alpha^{32}$P-dCTP, 2.0 µM second oligonucleotide of arbitrary sequence and 1.0 units of recombinant Taq DNA polymerase (GIBCO-BRL). Note that the concentration of the first oligonucleotide is now slightly less that 200 nM.

PCR™ fingerprinting was performed with one cycle of 94° C. for 2 min, 37° C. for 5 min then 72° C. for 5 min. This was followed by 40 cycles of 94° C. for 45 sec, 37° C. for 1 min, and 72° C. for 2 min. A final extension step of 72° C. for 5 min was performed. Next, 4.0 µl of the final PCR™ products were mixed with 6.0 µl of sequencing formamide dye mix and denatured by heating to 75° C. for 5 min. About 2.5 µl of the denatured PCR™ products in formamide dye was electrophoresed through a 6% polyacrylamide, 7M urea DNA sequencing style gel. PCR™ products were visualized by autoradiography.

Interleukin-8 was identified in a study in which the first arbitrary primer had the sequence 5'-AACAACTGGCAA-3' (SEQ ID NO:17). The second oligonucleotide of arbitrary sequence used in the PCR™ fingerprinting reaction that identified interleukin-8 was 5'-GGCGACAAGGAG-3' (SEQ ID NO:18). After autoradiography, bands that appeared differentially in fingerprinting reactions on the pooled total RNAs described above were cut out of the gels and reamplified by PCR™. Reamplified PCR™ products were cloned by the TA cloning method of Invitrogen, Inc. (San Diego, Calif.). The DNA sequence of multiple independent clones of each PCR™ product was determined.

4.11.3 Relative Quantitative RT-PCR™

DNA-free total RNA from the peripheral blood of healthy volunteers or patients with either metastatic prostate or breast cancer were converted into first strand cDNA using the *SuperScript™ Preamplification System for First Strand cDNA Synthesis* (GIBCO-BRL, Cat# 18089-011) following the directions obtained from the supplier. These cDNAs were then normalized to contain equal amounts of amplifiable cDNA by PCR™ amplification of β-actin cDNA using the primers 5'-GGAGCTGCCTGACGGCCAGGTCATC-3' (SEQ ID NO:19) and 5'-GAAGCATTTGCGGTGGAC-GATGGAG-3' (SEQ ID NO:7).

A typical PCR™ program would be 94° C. for 75 sec, followed by 22 cycles of 94° C. for 45 sec, 55° C. for 45 sec and 72° C. for 75 sec. This was followed by final extension of 72° C. for 5 min. PCR™ products were visualized by gel electrophoresis through 1.5% agarose TAE gels stained with ethidium bromide. Images of gels were captured, digitized and analyzed using the IS-1000 Digital Imaging System (Alpha Innotech Corp.). The concentrations of the cDNAs were adjusted by adding various amounts of water to create cDNA stocks that contained equal amounts of amplifiable β-actin cDNA.

Equal amounts of the normalized cDNA stock from individuals having the same disease state were pooled. Pools of cDNAs from healthy volunteers, patients with metastatic prostate cancer and metastatic breast cancer were constructed. The pools were then examine by PCR™ for β-actin to determine that they contained equal amounts of amplifiable cDNA.

To demonstrate that all observations were made in the log-linear phase of the PCR™ amplification curve, multiple PCR™ reactions were performed on each cDNA pool for each gene (primer pair) examined. The various PCR™ reactions were then removed from the thermocycler after different cycle numbers. Display of the PCR™ products on electrophoretic gels and analysis with the IS 1000 Digital Imaging System demonstrates that the mass of the PCR™ products is increased exponentially with increasing cycle number confirming observed results are in the log-linear portion of the PCR™ amplification curve.

Four oligonucleotides were used to examine the differential expression of IL-8 by relative quantitative RT-PCR™. The first primer anneals to the second exon and extends towards the poly A tail of the mRNA (5'-TTGCCAAG-GAGTGCTAAAGAAC-3', SEQ ID NO:20). Two similarly oriented oligonucleotides that anneal to exon 3 have the sequences 5'-TGGACCCCAAGGAAAACT-3' (SEQ ID NO:21) and 5'-GGGCCCAAGGAAAACT-3' (SEQ ID NO:22). An oligonucleotide that anneals to the fourth exon, extending towards the 5' cap of the mRNA, was used in pairwise combinations with the other three oligonucleotides in PCR™ (5'-TGGCAACCCTACAACAGACC-3', SEQ ID NO:11).

Relative quantitative RT-PCR of IL-10 gene products was performed as described for IL-8, except that the primers utilized were as listed below.

5'-TGACCCAGCCCCTTGAGAAACCT-3' (SEQ ID NO:14)

5'-AAGCCCCAAGCCCAGAGACAAGAT-3' (SEQ ID NO:47)

4.11.4 Serum Assays

Free and total PSA measurements were performed as described in sections 4.9.4.2 and 4.9.4.3 above. IL-8 was assayed as described in section 4.9.4.5, with one modification. All samples were run in triplicate with positive serum controls at three concentration levels. Microplates were rejected if the positive controls varied more than 10% at the low serum control concentration. However, the acceptance criteria for the R&D Systems resulted in a microplate rejection rate of 50%. Using these criteria the assay was sensitive to approximately 5.0 pg/ml.

4.11.5 Statistical Methods

Differences in free and total serum PSA and IL-8 data between BPH and cancer samples were examined using univariate logistic regression analysis (Stata Corporation, College Station, Tex.). In order to select a specific cutoff for continuous variables relevant to a binary outcome a Classification and Regression Tree analysis (CART) was applied (Sambrook et al., 1989). To assess the ability of the combined serum IL-8, total PSA and the corrected f/t PSA ratio results to predict the likelihood of cancer presence in men with an existing elevated total serum PSA, backwards stepwise logistic regression modeling was used (Hosmer and Lemeshow, 1989). The binary dependent variable assessed was the clinical outcome of BPH or cancer of the prostate (CAP). Receiver operator characteristic (ROC) curves were generated to predict the dependent outcome variable, BPH or CaP.

4.12 Identification of UC 331 and UC 332

4.12.1 Preparation of RNA

Eight ml of peripheral blood was collected from healthy volunteers, patients with clinically and biopsy confirmed BPH, localized and advanced metastatic prostate cancer, and from patients with advanced metastatic breast cancer. Metastatic prostate and breast cancer patients that had failed a primary therapy and had evidence of recurrence of disease were selected. The metastatic prostate cancer patients had high ($\geq 50$ ng/ml) serum concentrations of PSA.

4.12.2 RNA Fingerprinting

RNA was prepared as described in section 4.11.1 above. RNA fingerprinting with arbitrarily chosen oligonucleotide primers (Welsh et al., 1992) was performed as described in section 4.11.2, with certain modifications. In Example 7, the strategy of RNA fingerprinting used was similar to that described in Ralph et al. (1993) except that oligonucleotide primers used were composed of two discrete domains. The 5' domain of these oligonucleotides consisted of ten nucleotides that complemented sequences from either the T7 promotor or the M13 reverse sequencing primer. The 3' domains of these oligonucleotides were 8-mer sequences predicted to anneal frequently to the protein-coding regions of mRNAs in a promiscuous fashion (Lopez-Nieto and Nigam, 1996). These oligonucleotides were then used in a sequential pairwise strategy that optimizes the amount of mRNA complexity that can be surveyed with limited numbers of primers and starting RNA. Care was taken to ensure that the two oligonucleotides used to produce any single fingerprint did not share sequence similarity in either their 5' or 3' domains. Because these oligonucleotides were constructed of short sequence domains that have specific functions within this experimental design, the oligonucleotides are promiscuous rather than truly arbitrary in nature.

Two RNA pools were fingerprinted as described in section 4.11.2. Using the pooled RNAs as templates, first strand cDNA synthesis was primed by annealing one of the promiscuous oligonucleotide primers to the pooled RNAs at low stringency. The replicate fingerprints were initiated by using either 125 ng or 250 ng of RNA as template during first strand cDNA synthesis. Reaction conditions were as in section 4.11.2.

One-tenth (4.0 µl) of the first strand cDNA reaction mixture was used in the fingerprinting PCR™ reaction. PCR™ fingerprinting was performed as in section 4.11.2, except that PCR™ cycles consisted of one cycle of 94° C. for 2 min, 48° C. for 5 min then 72° C. for 5 min. This was followed by 35 cycles of 94° C. for 45 sec, 48° C. for 75 sec, and 72° C. for 2 min. A final extension step of 72° C. for 5 was performed. Next, 4.0 µl of the final PCR™ products were mixed with 6.0 µl of sequencing formamide dye solution and denatured by heating to 75° C. for 5 min. Approximately 2.5 µl of the denatured PCR™ products in formamide dye was electrophoresed through a 6% polyacrylamide, 7M urea DNA sequencing gel. PCR™ products were visualized by autoradiography.

5.0 EXAMPLES

5.1 Example 1

Relative Quantitative Reverse Transcriptase-Polymerase Chain Reaction—A Method to Evaluate Novel Genes (ESTS) as Diagnostic Biomarkers The reverse transcription-polymerase chain reaction (RT-PCR) protocols described in the following examples were developed as a means to determine the relative abundances of mRNA species that are expressed in various tissues, organs and cells. This protocol has been described as applied to prostate tissue in U.S. application Ser. No. 08/692,787, incorporated in relevant part herein by reference. The protocols used to meet this need must be robust, reproducible, relatively quantitative, sensitive, conservative in its use of resources, rapid and have a high throughput rate. Relative quantitative RT-PCR has the technical features that, in theory, meet all of these criteria. In practice there are six important barriers to implementing an RT-PCR based assay that compares the relative abundances of mRNA species. The protocol described herein addresses each of these six barriers and has permitted the realization of the potential of RT-PCR for this application. Although the present example is drawn to the identification and confirmation of differential expression in various physiological states in prostate tissue, the methods described herein may be applied to any type of tissue, and particularly to peripheral blood cells to provide a sensitive method of identifying differential expression.

The examination of candidate genes by this method that were partial cDNA fragments identified by RNA fingerprinting methodologies is described. This necessitated development of a relatively quantitative approach to independently confirm the differential expression of the mRNAs from which these partial cDNA fragments were derived. The key objective of the described screening protocol is the assessment of changes in the relative abundances of mRNA.

One advantage of RT-PCR is that it consumes relatively small quantities of RNA. With 20 µg of RNA per examined sample, the amount of RNA required to perform a single Northern blot experiment, 50-200 RT-PCR assays may be performed with up to four data points per assay. Another advantage is a high throughput, eight independent experiments which examine eight different mRNA species for differential expression may be performed simultaneously in a single PCR machine with 96 wells. A single individual skilled in this technique may thereby examine and evaluate eight genes per day without significant time constraints. By comparison, even if RNA of sufficient quality and quantity were available to do this number of Northern blots, a similarly skilled individual performing Northern blots would be hard pressed to examine and evaluate eight genes per week. In addition to the lower throughput rate of Northern blots, eight Northern blots per week would require the consumption of about 400 µCi of $^{32}P$ per week. While not dangerous to use in the hands of a skilled individual, $^{32}P$ is certainly inconvenient to use. RT-PCR avoids the use of radioactive materials.

An additional advantage of RT-PCR over Northern blots as a technological platform for evaluating the relative expression of mRNA species is that RT-PCR is much less sensitive to differences in quality of the RNA being examined. The human tissues described were removed from patients for treatment purposes and were only incidentally saved for further studies. Hence the RNA, an extremely labile molecule, is expected to be at least partially degraded. Because the RNA is separated by size on a gel in the Northern blot assay, partially degraded RNA appears as a smear, rather than discrete bands. By contrast, RT-PCR amplifies only a section or domain of an RNA molecule, and as long as that portion is intact, the size or degradation state of the entire molecule is irrelevant. As a result, RNAs that are identical except that they vary by degree of partial degradation will give much more variable signals in a Northern blot than they will in an RT-PCR. When samples are of variable quality, as is often the case in human studies, the relative sensitivities of the techniques to variation in sample quality is an important consideration.

In the practice of this method, total cell RNA is first converted into cDNA using reverse transcriptase primed with random hexamers. This protocol results in a cDNA population in which each RNA has contributed according to its relative proportion in original total cell RNA. If two RNA species differ by ten fold in their original relative abundances in the total cell RNA, then the cDNA derived from these two RNAs will also differ by ten fold in their relative abundances in the resulting population of cDNA. This is a conservation of relative proportionality in the conversion of RNA to cDNA.

Another consideration is the relative rates of amplification of a targeted cDNA by PCR. In theory, the amount of an amplified product synthesized by PCR will be equal to $M(E^C)$. Where M is the mass of the targeted cDNA molecules before the beginning of PCR and C is the number of PCR cycle performed. E is an efficiency of amplification factor. This factor is complex and varies between 1 and 2. The important consideration in this assay is that over most of a PCR amplification, E will be nearly constant and nearly equal to 2. In PCR reactions that are identical in every way except the cDNAs being used as templates are derived from different total cell RNAs, then E will have the same value in each reaction. If a cDNA target has an initial mass of $M_1$ in one PCR reaction and a mass of $M_2$ in another PCR reaction and if E has the same value in each reaction, then after C cycles of PCR there will be a mass of $M_1(E^C)$ of the amplified target in the first reaction and a mass of $M_2(E^C)$ of the amplified target in the second reaction. The ratios of these masses is unaltered by PCR amplification. That is $M1/M2=[M_1(E^C)]/M_2(E^C)$. Hence, there is a conservation of relative proportionality of amplified products during PCR.

Since both reverse transcription and PCR may be performed in such a way as to conserve proportionality, it is possible to compare the relative abundance of an mRNA species in two or more total cell RNA populations by first converting the RNA to cDNA and then amplifying a fragment of the cDNA derived from the specific mRNA by PCR. The ratio of the amplified masses of the targeted cDNA is very close to or identical to the ratios of the mRNAs in the original total cell RNA populations.

Six major challenges or barriers to be overcome in order to best use RT-PCR to quantify the relative abundances of RNA are as follows:

1) Degradation of RNA must be minimized during RNA preparation.

2) Genomic DNA must be eliminated.

3) RNA must be free of contaminants that might interfere with reverse transcription.

4) The efficiency of RT is variable. cDNAs, not RNA, must be normalized for equal concentrations of amplifiable cDNA.

5) Limited linear range requires multiple sampling points in any amplification curve.

6) Tube to tube variability in PCR

It is the development of techniques to overcome these barriers and to provide a sensitive and accurate method of quantitative RT-PCR that is applicable to any tissue type, or cell type such as peripheral blood cells, or physiological state that is a part of the present invention.

The first three barriers to successful RT-PCR are all related to the quality of the RNA used in this assay. The protocols described in this section address the first two barriers as described in the last section. These are the requirements that degradation of RNA must be minimized during RNA preparation and that genomic DNA must be eliminated from the RNA.

These preferred methods for RNA isolation are the guanidinium thiocyanate and STAT-60 methods, which are well known in the art, and kits for RNA isolation manufactured by Qiagen, Inc. (Chatworth, Calif.) and Tel-Test, Inc. (Friendswood, Tex.) respectively, with the kits being the most preferred for convenience. Four protocols are performed on the RNA isolated by either method (or any method) before the RNA is be used in RT-PCR.

The first of these four protocols is digestion of the RNAs with DnaseI to remove all genomic DNA that was co-isolated with the total cell RNA. Prior to DNaseI digestion, the RNA is in a particulate suspension in 70% ethanol. Approximately 50 µg of RNA (as determined by $OD_{260/280}$) is removed from the suspension and precipitated. This RNA is resuspended in DEPC treated sterile water. To this is added 10× DNaseI buffer (200 mM Tris-HCl; pH 8.4, 20 mM $MgCl_2$, 500 mM KCl), 10 units of RNase Inhibitor (GIBCO-BRL Cat#15518-012) and 20 units of DNaseI (GIBCO-BRL # 18068-015). The volume is adjusted to 50 µl with additional DEPC treated water. The reaction is incubated at 37° C. for 30 minutes. After DNaseI digestion the RNAs are organic solvent-extracted with phenol and chloroform followed by ethanol precipitation. This represents the second ethanol precipitation of the isolated RNA. Empirical observations suggest that this repeated precipitation improves RNA performance in the RT reaction to follow.

Following DNaseI digestion, an aliquot of the RNA suspension in ethanol is removed and divided into thirds. A different procedure is performed on each one of the aliquot thirds. These three procedures are: (1). An $OD_{260/280}$ is obtained using a standard protocol and is used to estimate the amount of RNA present and its likely quality. (2). An aliquot is run out on an agarose gel, and the RNA is stained with ethidium bromide. Observation that both the 28S and 18S RNAs are visible as discreet bands and that there is little staining above the point at which the 28S rRNA migrates indicate that the RNA is relatively intact. While it is not critical to assay performance that the examined RNAs be completely free of partial degradation, it is important to determine that the RNA is not so degraded as to significantly affect the appearance of the 28S rRNA. (3). The total cell RNAs are run using a PCR-based test that confirms that the DNaseI treatment actually digested the contaminating genomic DNA to completion. It is very important to confirm complete digestion of genomic DNA because genomic DNA may act as a template in PCR reactions resulting in false positive signals in the relative quantitative RT-PCR assay described below. The assay for contaminating genomic DNA utilizes gene specific oligonucleotides that flank a 145 nucleotide long intron (intron #3) in the gene encoding Prostate Specific Antigen (PSA). This is a single copy gene with no pseudogenes. It is a member of the kallikrein gene family of serine proteases, but the oligonucleotides used in this assay are specific to PSA. The sequences of these oligonucleotides are:

5'CGCCTCAGGCTGGGGCAGCATT 3', SEQ ID NO:4
and
5'ACAGTGGAAGAGTCTCATTCGAGAT 3', SEQ ID NO:5.

In the assay for contaminating genomic DNA, 500 ng to 1.0 µg of each of the DNaseI treated RNAs are used as templates in a standard PCR (35-40 cycles under conditions described below) in which the oligonucleotides described above are used as primers. Human genomic DNA is used as the appropriate positive control. This DNA may be purchased from a commercial vender. A positive signal in this assay is the amplification of a 242 nucleotide genomic DNA specific PCR product from the RNA sample being tested as visualized on an ethidium bromide stained electrophoretic gel. There should be no evidence of genomic DNA as indicated by this assay in the RNAs used in the RT-PCR assay described below. Evidence of contaminating genomic DNA results in re-digestion of the RNA with DNaseI and reevaluation of the DNase treated RNA by determining its $OD_{260/280}$ ratio, examination on electrophoretic gel and re-testing for genomic DNA contamination using the described PCR assay.

The standard conditions used for PCR (as mentioned in the last paragraph) are:

1×GIBCO-BRL PCR reaction buffer [20 mM Tris-Cl (pH 8.4), 50 mM KCl]

1.5 mM $MgCl_2$

200 μM each of the four dNTPs 200 nM each oligonucleotide primer concentration of template as appropriate 2.5 units of Taq polymerase per 100 μl of reaction volume.

Using these conditions, PCR is performed with 35-40 cycles of:

94° C. for 45 sec

55°-60° C. for 45 sec

72° C. for 1 minute.

The protocols described in the above section permit isolation of total cellular RNA that overcomes two of the six barriers to successful RT-PCR, i.e. the RNA is acceptably intact and is free from contaminating genomic DNA.

Reverse transcriptases, also called RNA dependent DNA polymerases, as applied in currently used molecular biology protocols, are known to be less processive than other commonly used nucleic acid polymerases. It has been observed that not only is the efficiency of conversion of RNA to cDNA relatively inefficient, there is also several fold variation in the efficiency of cDNA synthesis between reactions that use RNAs as templates that otherwise appear indistinguishable. The sources of this variation are not well characterized, but empirically, it has been observed that the efficiencies of some reverse transcription (RT) reactions may be improved by repeated organic extractions and ethanol precipitations. This implies that some of the variation in RT is due to contaminants in the RNA templates. In this case, the DNaseI treatment described above may be aiding the efficiency of RT by subjecting the RNA to an additional cycle of extraction with phenol and chloroform and ethanol precipitation. Contamination of the template RNA with inhibitors of RT is an important barrier to successful RT that is partially overcome by careful RNA preparation and repeated organic extractions and ethanol precipitations.

Reverse transcription reactions are performed using the Superscript™ Preamplification System for First Strand cDNA Synthesis kit which is manufactured by GIBCO-BRL LifeTechnologies (Gaithersburg, Md.). Superscript™ is a cloned form of M-MLV reverse transcriptase that has been deleted for its endogenous Rnase H activity in order to enhance its processivity. In the present example, the published protocols of the manufacturer are used for cDNA synthesis primed with random hexamers. cDNA synthesis may also be primed with a mixture of random hexamers (or other small oligonucleotides of random sequence) and oligo dT. The addition of oligo dT increases the efficiency of conversion of RNA to cDNA proximal to the polyA tail. As template, either 5 or 10 micrograms of RNA is used (depending on availability). After the RT reaction has been completed according to the protocol provided by GIBCO-BRL, the RT reaction is diluted with water to a final volume of 100 μl.

Even with the best prepared RNA and the most processive enzyme, there may be significant variation in the efficiency of RT. This variation would be sufficiently great that cDNA made in different RTs could not be reliably compared. To overcome this possible variation, cDNA populations made from different RT reactions may be normalized to contain equal concentrations of amplifiable cDNA synthesized from mRNAs that are known not to vary between the physiological states being examined. In the present examples, cDNAs made from total cell RNAs are normalized to contain equal concentrations of amplifiable β-actin cDNA.

One μl of each diluted RT reaction is subjected to PCR using oligonucleotides specific to β-actin as primers. These primers are designed to cross introns, permitting the differentiation of cDNA and genomic DNA. These β-actin specific oligonucleotides have the sequences:

5' CGAGCTGCCTGACGGCCAGGTCATC 3', SEQ ID NO:6 and

5' GAAGCATTTGCGGTGGACGATGGAG 3', SEQ ID NO:7

PCR is performed under standard conditions as described previously for either 19 or 20 cycles. The resulting PCR product is 415 nucleotides in length. The product is examined by PCR using agarose gel electrophoresis followed by staining with ethidium bromide. The amplified cDNA fragment is then visualized by irradiation with ultra violet light using a transilluminator. A white light image of the illuminated gel is captured by an IS-1000 Digital Imaging System manufactured by Alpha Innotech Corporation. The captured image is analyzed using either version 2.0 or 2.01 of the software package supplied by the manufacturer to determine the relative amounts of amplified β-actin cDNA in each RT reaction.

To normalize the various cDNAs, water is added to the most concentrated cDNAs as determined by the assay described in the last paragraph. PCR using 1 μl of the newly rediluted and adjusted cDNA is repeated using the β-actin oligonucleotides as primers. The number of cycles of PCR must be increased to 21 or 22 cycles in order to compensate for the decreased concentrations of the newly diluted cDNAs. With this empirical method the cDNAs may be adjusted by dilution to contain roughly equal concentrations of amplifiable cDNA. Sometimes this process must be repeated to give acceptable final normalization. By dividing the average optical density of all observed bands by that of a particular band, a normalization statistic may be created that will permit more accurate comparisons of the relative abundances of RNAs examined in the normalized panel of cDNAs.

Once the normalization statistics are derived, PCR may be performed using different gene specific oligonucleotides as primers to determine the relative abundances of other mRNAs as represented as cDNAs in the normalized panel of diluted RT reaction products. The relative intensities of the bands is then adjusted and normalized to β-actin expression by multiplying the intensity quantities by the normalization statistics derived.

In the next section an RT-PCR assay is discussed that uses pooled cDNAs and is more likely to capture data from PCRs while in the linear portions of their amplification curves. The error caused by observing PCRs after the linear portion of PCR is in the direction of quantitatively underestimating mRNA abundance differences. To determine quantitative differences in mRNA expression, it is necessary that the data is collected in the linear portion of the respective PCR amplification curves. This requirement is met in the assay described in following paragraphs.

The last two barriers to RT-PCR are addressed in the sections that follow involving the use of pooled cDNAs as templates in RT-PCR. In practice, the protocols using pooled templates are usually performed before the protocol described above.

There are two additional barriers to relative mRNA quantitation with RT-PCR that frequently compromise interpretations of results obtained by this method. The first of these involves the need to quantify the amplification products while the PCR is still in the linear portion of the process where "E" behaves as a constant and is nearly equal to two. In the "linear" portion of the amplification curve, the log of the mass of the amplified product is directly proportional to the cycle number. At the end of the PCR process, "E" is not constant. Late in PCR, "E" declines with each additional cycle until there is no increase in PCR product mass with additional cycles.

The most important reason why the efficiency of amplification decreases at high PCR cycle number, may be that the concentration of the PCR products becomes high enough that the two strands of the product begin to anneal to each other with a greater efficiency than that at which the oligonucleotide primers anneal to the individual product strands. This competition between the PCR product strands and the oligonucleotide primers creates a decrease in PCR efficiency. This part of the PCR where the efficiency of amplification is decreased is called the "plateau" phase of the amplification curve. When "E" ceases to behave as a constant and the PCR begins to move towards the plateau phase, the conservation of relative proportionality of amplified products during PCR is lost. This creates an error in estimating the differences in relative abundance of an mRNA species occurring in different total cell RNA populations. This error is always in the same direction, in that it causes differences in relative mRNA abundances to appear less than they actually are. In the extreme case, where all PCRs have entered the plateau phase, this effect will cause differentially expressed mRNAs to appear as if they are not differentially expressed at all.

To control for this type of error, it is important that the PCR products be quantified in the linear portion of the amplification curve. This is technically difficult because currently used means of DNA quantitation are only sensitive enough to quantify the PCR products when they are approaching concentrations at which the product strands begin to compete with the primers for annealing. This means that the PCR products may only be detected at the very end of the linear range of the amplification curve. Predicting in advance at what cycle number the PCR products should be quantified is technically difficult.

Practically speaking, it is necessary to sample the PCR products at a variety of cycle numbers that are believed to span the optimum detection range in which the products are abundant enough to detect, but still in the linear range of the amplification curve. It is impractical to do this in a study that involves large numbers of samples because the number of different PCR reactions and/or number of different electrophoretic gels that must be run becomes prohibitively large.

To overcome these limitations, a two tiered approach was designed to relatively quantify mRNA abundance levels using RT-PCR. In the first tier, pools of cDNAs produced by combining equal amounts of normalized cDNA are examined to determine how mRNA abundances vary in the average individual with a particular physiological state. This reduces the number of compared samples to a very small number such as two to four. In the studies described herein, two pools are examined. These are pools of normal individuals and those individuals with metastatic prostate cancer. Each pool may contain a large number of individuals. While this approach does not discriminate differences between individuals, it may easily discern broad patterns of differential expression. The great advantage of examining pooled cDNAs is that it permits many duplicate PCR reactions to be simultaneously set up.

The individual duplicates may be harvested and examined at different cycle numbers of PCR. In studies described below, four duplicate PCR reactions were set up. One duplicate was collected at 31, 34, 37, and 40 PCR cycles. Occasionally, PCR reactions were also collected at 28 cycles. Examining the PCRs at different cycle numbers yielded the following benefits. It is very likely that at least one of the RT-PCRs will be in the optimum portion of the amplification curves to reliably compare relative mRNA abundances. In addition, the optimum cycle number will be known, so that studies with much larger sample sizes are much more likely to succeed. This is the second tier of a two tiered approach that has been taken to relatively quantify mRNA abundance levels using RT-PCR. Doing the RT-PCR with the pooled samples permits much more efficient application of RT-PCR to the samples derived from individuals. A further benefit, also as discussed below, tube to tube variability in PCR may be discounted and controlled because most studies yield multiple data points due to duplication.

Like the previously described protocol involving individuals, the first step in this protocol is to normalize the pooled samples to contain equal amounts of amplifiable cDNA. This is done using oligonucleotides that direct the amplification of β-actin. In this example, a PCR amplification of a cDNA fragment derived from the β-actin mRNA from pools of normal individuals and individuals with metastatic prostate cancer was performed. This study was set up as four identical PCR reactions. The products of these PCRs were collected and electrophoresed after 22, 25, 28 and 31 PCR cycles. Quantitation of these bands using the IS 1000 system showed that the PCRs were still in the linear ranges of their amplification curves at 22, 25 and 28 cycles but that they left linearity at 31 cycles. This is known because the ratios of the band intensities remain constant and internally consistent for the data obtained from 22, 25 and 28 cycles, but these ratios become distorted at 31 cycles. This quantitation will also permit the derivation of normalizing statistics for the three pools relative to each other in exactly the same manner as was done previously for individuals.

This study is then repeated using gene specific primers for a gene other than β-actin. The intensities of the relevant bands were quantitated using the IS 1000 and normalized to the β-actin signals.

The central question to be answered in analyzing this data is whether the PCRs have been examined in the linear portions of their amplification curves. A test for this may be devised by determining if the proportionality of the PCR products has been conserved as PCR cycle number has increased. If the ratio between the two pools of a given PCR product remains constant with increasing cycle number, this is strong evidence that the PCRs were in the linear portions of their amplification curves when these observations were made. (This is better conservation of proportionality than is frequently observed. In some studies, data was excepted when the ratios were similar but not identical.) This conservation of proportionality was lost at 40 cycles. This indicates that these PCRs are nearing the plateau phases of their amplification curves.

The final major barrier to quantifying relative mRNA abundances with RT-PCR is tube to tube variability in PCR. This may result from many factors, including unequal heating and cooling in the thermocycler, imperfections in the PCR tubes and operator error. To control for this source of variation, the Cole-Parmer digital thermocouple Model # 8402-00 was used to calibrate the thermocyclers used in these studies. Only slight variations in temperature were observed.

To rigorously demonstrate that PCR tube to tube variability was not a factor in the studies described above, 24 duplicate PCRs for β-actin using the same cDNA as template were performed. These PCR tubes were scattered over the surface of a 96 well thermocycler, including the corners of the block where it might be suspected the temperature might deviate from other areas. Tubes were collected at various cycle numbers. Nine tubes were collected at 21 cycles. Nine tubes were collected at 24 cycles, and six tubes were collected at 27 cycles. Quantitation of the intensities of the resulting bands with the IS 1000 system determined that the standard error of the mean of the PCR product abundances was ±13%. This is an acceptably small number to be discounted as a major source of variability in an RT-PCR assay.

The RT-PCR protocol examining pooled cDNAs is internally controlled for tube to tube variability that might arise from any source. By examining the abundance of the PCR products at several different cycle numbers, it may be determined that the mass of the expected PCR product is increasing appropriately with increasing PCR cycle number. Not only does this demonstrate that the PCRs are being examined in the linear phase of the PCR, where the data is most reliable, it demonstrates that each reaction with the same template is consistent with the data from the surrounding cycle numbers. If there was an unexplained source of variation, the expectation that PCR product mass would increase appropriately with increasing cycle number would not be met. This would indicate artifactual variation in results. Internal duplication and consistency of the data derived from different cycle numbers controls for system derived variation in tube to tube results.

As described in the preceding paragraphs, the RT-PCR protocol using pooled cDNA templates overcomes the last two barriers to effective relative quantitative RT-PCR. These barriers are the need examine the PCR products while the reactions are in the linear portions of their amplification curves and the need to control tube to tube variation in PCR. The described protocol examines PCR products at three to four different cycle numbers. This insures that the PCRs are quantitated in their linear ranges and, as discussed in the last paragraph, controls for possible tube to tube variation.

One final question is whether β-actin is an appropriate internal standard for mRNA quantitation. β-actin has been used by many investigators to normalize mRNA levels. Others have argued that β-actin is itself differentially regulated and therefore unsuitable as an internal normalization standard. In the protocols described herein differential regulation of β-actin is not a concern. More than fifty genes have been examined for differential expression using these protocols. Fewer than half were actually differentially expressed. The other half were regulated similarly to β-actin within the standard error of 13%. Either all of these genes are coordinately differentially regulated with β-actin, or none of them are differentially regulated. The possibility that all of these genes could be similarly and coordinately differentially regulated with β-actin seems highly unlikely. This possibility has been discounted.

β-actin has also been criticized by some as an internal standard in PCRs because of the large number of pseudogenes of β-actin that occur in mammalian genomes. This is not a consideration in the described assays because all of the RNAs used herein are demonstrated to be free of contaminating genomic DNA by a very sensitive PCR based assay. In addition, the cycle number of PCR needed to detect β-actin cDNA from the diluted RT reactions, usually between 19 and 22 cycles, is sufficiently low to discount any contribution that genomic DNA might make to the abundance of amplifiable β-actin templates.

5.2 Example 2

Identification of Markers of Metastatic Prostate Cancer by Use of RNA Fingerprinting by PCR Primed with Oligonucleotides of Arbitrary Sequence RNA fingerprinting by PCR, primed with oligonucleotides of arbitrary sequence was performed on RNAs isolated from peripheral human blood. Bands which appeared to be differentially expressed were cloned.

For this study, total cell RNA was isolated from buffy coat cells as described above. cDNA was made from one to five μg of each isolated RNA. All cDNAs were normalized for similar amounts of β-actin cDNA by RT-PCR. RT-PCR products were electrophoresed through agarose.

For relative quantitative RT-PCR with an external standard, quantitation of band intensities on ethidium bromide stained gels was performed using the IS-1000 image analysis system manufactured by the Alpha Innotech Corp. A normalizing statistic was generated for each cDNA sample, as the average of all β-actin signals divided by the β-actin signal for each cDNA sample respectively. Data for each sample was then normalized by multiplying the observed densitometry observation by the individual normalizing statistics. Normalized values predict differences in the steady state abundances of the respective mRNAs in the original total cell RNA samples.

The nucleotide sequences of all cloned PCR products were determined by dideoxy termination sequencing using either the ABI or Pharmacia automated sequencers.

This protocol resulted in the discovery of an mRNA species that was 2-3 fold less abundant in the peripheral blood of metastatic prostate cancer patients than in the peripheral blood of normal individuals of both sexes. The sequence of this band, referred to as UCBP Band #35 (SEQ ID NO:1), matches an EST derived from a fetal brain cDNA library (GenBank Accession #T03013). Down regulation of this band in the peripheral blood of metastatic prostate cancer patients was confirmed by relative quantitative RT-PCR.

5.3 Example 3

Identification of Markers of Metastatic Prostate Cancer by Use of RNA Fingerprinting by the Pairwise Sequential Method RNA fingerprinting was used to identify differentially expressed RNA species according to the pairwise sequential method of McClelland et al. (1994), as modified to use larger (17-25 mer) arbitrary oligonucleotides. PCR amplification products were labeled using α-32P-dCTP and were visualized by autoradiography after electrophoresis on denaturing polyacrylamide gels. A number of bands appeared to be differentially expressed, and were cloned as described above. The differentially expressed bands identified in this Example and in Example 2 above are listed in Table 4.

UC Band #321 was confirmed by RT-PCR to be down regulated in the peripheral blood of prostate cancer patients, with a four-fold decrease observed compared with normal individuals. The DNA sequence of Band #321 does not match any known sequences in the GenBank database. It therefore represents a previously undescribed gene product.

UC Band #302 and UC Band #325 were both observed to be up regulated in the peripheral blood of metastatic prostate cancer patients. UC Band #302 is identical in sequence to a portion of the sequence of elongation factor 1-α (GenBank Accession #X03558). This band was modestly increased between 1.6 and 2-fold in metastatic cancer patients compared with normal individuals.

UC Band #325 was found to consist of two different alternatively spliced forms of mRNA, encoded by the interleukin-8 (IL-8) gene. UC Band #325-1, the previously identified mRNA species of IL-8 (Genbank Accession #Y00787), is approximately seven-fold more abundant in the peripheral blood of metastatic prostate cancer patients. The alternatively spliced IL-8 mRNA, containing intron #3 of the IL-8 gene (Genbank Accession #M28130) is up to seven-fold less abundant in the peripheral blood of metastatic prostate cancer patients. Overall, there is an approximately 30-fold change in the ratios of the two spliced forms of IL-8 mRNA in individuals with metastatic prostate cancer compared with normal individuals. These results have been confirmed by relative quantitative RT-PCR.

As described above, an increased expression of IL-8 mRNA has been previously reported in cancer patients. However, this represents the first finding of an alternatively spliced form of IL-8 mRNA, containing intron 3, that is significantly more abundant in normal individuals compared with metastatic prostate cancer patients. These results are surprising in view of previous reports which had failed to find any alternatively spliced forms of IL-8 mRNA in normal individuals or cancer patients.

It will be recognized that the genes and gene products (RNAs and proteins) for the above described markers of metastatic prostate cancer are included within the scope of the disclosure herein described. It will also be recognized that the diagnosis and prognosis of metastatic prostatic cancer by detection of the nucleic acid products of these genes are included within the scope of the present invention. Serological and other assays to detect these mRNA species or their translation products are also indicated. It is obvious that these assays are of utility in diagnosing metastatic cancers derived from prostate and other tissues.

Most significantly, these Examples demonstrate the feasibility of using RNA fingerprinting to identify mRNA species that are differentially expressed in the peripheral blood of patients with asymptomatic diseases or in patients with symptoms that are insufficient for a definitive diagnosis. It will be appreciated that this technique is applicable not only to the detection and diagnosis of prostate and other cancers, but also to any other disease states which produce significant effects on leukocyte gene expression. Uses which are contemplated within the scope of the present disclosure include the detection and diagnosis of clinically significant diseases that require medical intervention, including but not limited to asthma, lupus erythromatosis, rheumatoid arthritis, multiple sclerosis, myasthenia gravis, autoimmune thyroiditis, ALS, interstitial cystitis and prostatitis.

TABLE 4

GENES WHOSE MRNAS HAVE ABUNDANCES THAT VARY IN METASTATIC PROSTATE CANCER RELATIVE TO NORMAL INDIVIDUALS

| Name of cDNA Fragment | Sequence Determined | Confirmed by RT-PCR | Previously Known |
|---|---|---|---|
| UC 302 SEQ ID NO:1 | Yes | Yes | EF 1-α |
| UC 325-1 SEQ ID NO:2 | Yes | Yes | GB #Y00787 |
| UC 325-2 SEQ ID NO:3 | Yes | Yes | IL-8 |
| UC 331 SEQ ID NO:29 | Yes | Yes | various ESTs |
| UC 332 SEQ ID NO:34 | Yes | Yes | GB #D87451 |
| IL-10 | No | Yes | GB #M57627 |
| UCPB 35 SEQ ID NO:48 | Yes | Yes | GB #T03013 |
| UC 321 SEQ ID NO:49 | Yes | Yes | No |

GB = Genbank Accession Number

TABLE 5

OLIGONUCLEOTIDES USED IN RELATIVE QUANTITATIVE RT-PCR

Oligonucleotides used to examine the expression of genes:

UC Band #302 (elongation factor 1-α).

5' GACAACATGCTGGAGCCAAGTGC3', SEQ ID NO:8

5' ACCACCAATTTTGTAAGAACATCCT3', SEQ ID NO:9

UC Band #325-1 (IL-8).

5' GGGCCCCAAGGAAAACT3', SEQ ID NO:10

5' TGGCAACCCTACAACAGACC3', SEQ ID NO:11

UC Band #325-2 (IL-8).

5' GGGCCCCAAGGAAAACT3', SEQ ID NO:12

5' TGGCAACCCTACAACAGACC3', SEQ ID NO:11

UC Band #331 (various ESTs)

5'-ACGACTCACTATAAGCAGGA-3' (SEQ ID NO:13)

5'-AACAGCTATGACCATCGTGG-3' (SEQ ID NO:23)

5'-CTGGCCTACGGAAGATACGACAC-3' (SEQ ID NO:25)

5'-ACAATCCGGAGGCATCAGAAACT-3' (SEQ ID NO:26)

UC Band #332 (D87451)

5'-ACGACTCACTATGTGGAGAA-3' (SEQ ID NO:24)

5'-AACAGCTATGACCCTGAGGA-3' (SEQ ID NO:46)

5'-AGCCCCGGCCTCCTCGTCCTC-3' (SEQ ID NO:27)

5'-GGCGGCGGCAGCGGTTCTC-3' (SEQ ID NO:28)

IL-10 (M57627)

5'-TGACCCAGCCCCTTGAGAAACCT-3' (SEQ ID NO:14)

5'-AAGCCCCAAGCCCAGAGACAAGAT-3' (SEQ ID NO:47)

TABLE 5-continued

OLIGONUCLEOTIDES USED IN RELATIVE QUANTITATIVE RT-PCR

UCPB Band #35 (previously uncharacterized gene).

SEQ ID NO:50

5' TGCAAACTTTCACCTGGACTT3',

SEQ ID NO:51

5' CTTGTGACTTGCTTTGATAGAATG3',

UC Band #321 (previously uncharacterized gene).

SEQ ID NO:52

5' TGTCCAGAGATCCAAGTGCAGAAGG3',

SEQ ID NO:53

5' GAGCTCCAGGAGACAGAAGCCATAG3',

Controls used to normalize relative quantitative RT-PCR

β-actin

SEQ ID NO:6

5' CGAGCTGCCTGACGGCCAGGTCATC3',

SEQ ID NO:7

5' GAAGCATTTGCGGTGGACGATGGAG3',

Asparagine Synthetase (AS)

SEQ ID NO:54

5' ACATTGAAGCACTCCGCGAC3'

SEQ ID NO:55

5' AGAGTGGCAGCAACCAAGCT3'

5.4 Example 4

DNA Sequences of Markers of Metastatic Prostate Cancer

The DNA sequences of the markers of metastatic prostate cancer were determined by Sanger dideoxy sequencing as detailed above. The identified sequences are provided in Table 6. The sequences of UC Band # 331 and UC Band # 332 are from Example 6 below.

TABLE 6

DNA SEQUENCES OF MARKERS OF METASTATIC PROSTATE CANCER:

UC Band #302 (SEQ ID NO:1) Human Elongation Factor 1-alpha, Genbank Accession #X03558

5'GGTGAGCCCCAGGAGACAGAAGAGATATGAGGAAATTGTTAAGGAAGTC

AGCACTTACATTAAGAAAATTGGCTACAACCCCGACACAGTAGCATTTGTG

CCAATTTCTGGTTGGAATGGTGACAACATGCTGGAGCCAAGTGCTAACATG

CCTTGGTTCAAGGGATGGAAAGTCACCCGTAAGGATGGCAATGCCAGTGGA

ACCACGCTGCTTGAGGCTCTGGACTGCATCCTACCACCAACTCGTCCAACT

GACAAGCCCTTGCGCCTGCCTCTCCAAGGATGTTCTTACAAAATTGGTGGT

ATTGGTACTGTTCCCTGTTTGGCCGAATTGGAAAACTGGTGTTCCTCCAAA

CCCCGGTTATGGTGGGTTTCCTCCTCCTTGGA 3'

UC Band #325-1 (SEQ ID NO:2) Human IL-8 mRNA, Genbank Accession #Y00787

5'GGGCGGAACAAGGGAGCGCTAAAAGGAAATTAGGATGTCAGGTGCATAA

TABLE 6-continued

DNA SEQUENCES OF MARKERS OF METASTATIC PROSTATE CANCER:

AGGACATAATTCCAAAACCTTTCCAAACCCCAAATTTATTCAAAGGAACTG

AGGAGTGGATTGAGGAGTGGGACCAACACTGGCGCCAAACACAGAAATTAT

TGTAAAGCTTTCTGATGGAAGAGAGCTCTGTCTGGGCCCCAAGGAAAACTG

GGTGCAGAGGGTTGTGGAGAAGTTTTTGAAGAGGGCTGAGAATTCATAAAA

AAATTCATTCTCTGTGGTATCCAAGAATCAGTGAAGATGCCAGTGAAACTT

CAAGCAAATCTACTTCAACACTTCATGTATTGTGTGGGTCTGTTGTAGGGT

TGCCAGTTGTT 3'

UC Band #325-2 (SEQ ID NO:3) Human IL-8 mRNA containing intron #3

5'GCTTGGGCCCCAAGGAAAACTGGGTGCAGAGGGTTGTGGAGAAGTTTTT

GAAGAGGTAAGTTATATATTTTTGAATTTAAAATTTGTCATTTATCCGTGA

GACATATAATCCAAAGTCAGCCTATAAATTTCTTTCTGTTGCTAAAAATCG

TCATTAGGTATCTGCCTTTTTGGTTAAAAAAAAAAGGAATAGCATCAATAG

TGAGTGTGTTGTACTCATGACCAGAAAGACCATACATAGTTTGCCCAGGAA

ATTCTGGGTTAAGCTTGTGTCCTATACTCTTAGTAAAGTTCTTTGTCACTC

CCAGTAGTGTCCTATGTTAGATGATAATGTCTTTGATCTCCCTATTTATAG

TTGAGAATATAGAGCATGTCTAACACATGAATGTCAAAGACTATATTGACT

TTTCAAGAACCCTACTTTCCTTCTTATTAAACATGCTCATCTTTATATTGT

GAATTTTATTTTAGGGCTGAGAATTCATAAAAAAATTCATTCTCTGTGGTA

TCCAAGAATCAGTGAAGATGCCAGTGAAACTTCAAGCAAATCTACTTCAAC

ACTTCATGTATTGTGTGGGTCTGTTGTAGGGTTGCCA 3'

UCPB Band #35 (SEQ ID NO:48) Matches a fetal brain EST, GenBank Accession #T03013

5'GGCAGGGGCTTGTGACTCTAAGATGGCTTCATTCACATGCCTAGGGCCT

CAGTAGGATGACTGGCATGGCCCTGGAAAACTGCGAAGTCTTCTCTCTGTG

CAAACTTTCACCTGGACTTTTTATATGATTCTGGAAGTATTCCAAGAAGGC

AAAAGTAAAAACTGCAAAGCGTCTTAAAATAGAAGTTCAGAAGCCACATTA

TATCACTTCTGTTGCATTCTATCAAAGCAAGTCACAAGCCCCTGCCAATCA

3'

UC Band #321 (SEQ ID NO:49) previously uncharacterized Gene

5'CACACACTCCCCCATTCTGAGCCCCAAGAGGCTCATCCCTAAGGATGTC

CAGAGATCCAAGTGCAGAAGGAGAATGTGGTGAGGCTATTTATTCCCCCAG

TGCCTTCCCTGCTGGGCTATGGATGAACAGTGGCTGACTTCATCTAGGAAA

GAGCTATGGCTTCTGTCTCCTGGAGCTCACCA 3'

UC Band #331 (SEQ ID NO:29) various ESTs

5'GCGGCAGGCGCGGCAAATTACGTTGCCGGAGCTGAACGGCGCGGCTGGT

CTGAAGGCAAACAAGCGAGCGAGCGCGCGATAGGGCCGAGAGGACGCGCGC

AGGTGGCGGCGTTGCCATGTCGCACGGTCACAGCCACGGCGGGGGTGGCTG

TABLE 6-continued

DNA SEQUENCES OF MARKERS OF
METASTATIC PROSTATE CANCER:

CCGCTGCGCCGCCGAACGGGAGGAGCCGCCCGAGCAGCGCGGCCTGGCCTA

CGGCCTGTACCTGCGCATCGACCTGGAGCGGCTGCAATGCCTTAACGAGAG

CCGCGAGGGCAGCGGCCGCGGCGTCTTCAAGCCATGGGAGGAGCGGACCGA

CCGCTCCAAGTTTATTGAAAGTGATGCAGATGAAGAGCTTCTGTTTAATAT

TCCATTTACGGGCAATGTCAAGCTCAAAGGCATCATTATAATGGGAGAGGA

TGATGACTCACACCCTCTGAGCATGAGCATGTACAAGAATATTCCACCGAT

GTCCTTTGATGATACAGAAAGGGAGCCAGATCAGACCTTTAGTCTGAACCG

GGATCTTACAGGAGAATTAGAGTATGCTACAAAAATTTCTCGTTTTTCAAA

TGTCTATCATCTCTCAATTCATATTTCAAAAAACTTCGGAGCAGATACGAC

AAAGGTCTTTTATATTGGCCTGAGAGGAGAGTGGACTGAGCTTCGCCGACA

CGAGGTACCATCTGCAATTACGAAGCATCTGCCAACCCAGCAGACCATAGG

GTCCATAGGTTACCCCACAGACACACTTTATTTCCTAAGGGCTGGCCAAGG

CTCCCATAGAGGCGCTGTGTCAGTGAAGATGTACGACTACCTGTTGGGAAG

GACAAAGGGATGAGGCTCCAGAGAGAGTTGGCTGCCACAGCTCTGCCAAGC

TTTGTCTTTGGGGCTTGCTGCAGAAACCTGGCCTACGGAAGATACGACACC

ACTGGGAGGGTTGTGTAGGTGCCAGGGGACCATCGTGGTTCTCTAGGGCGC

TGTGGAAATTGGGTCTTGGGCTGGGTGGCATCTGGCAGTCATGGGTAACAC

TTGCTTTTCCAGTTAATGTGGCCATGTGATTCCAAGTGTCATGTTGCTTTG

TGGAAGATTGTTGTGTGACTTGTTTTTTTGATTTTGTATTTGTTTTTTTAA

AGGAAACTATTGTGGGCTATAGGAAACTTTCTGATGCCTCCGGATTGTGTT

AGTAGTAGCCATCAGGAGGGTCTCCAACTAAAACACTTGTTCCTGCTTGCT

CCTTTCCCCTCTCATGTTCAGCATTCTTGTCAAGTTGCCCAGCTTGGAGGT

TGTCTGTCACGCACATGTGTCCTGTGGTTATAGCTAGAAGGACAGGAGTCT

CCTGCTGATGCGTGATAGCTTAAGCTTGGGGAGAAGGTCTTTTCCACTGCC

TAGCTAAGCAGTCTGGGGAGAGCATGGGGATCATTTCTATGTGTGTGGGTA

ATCTGGTCAGTAAGATTGAGACTTAGTTAAGATTCCCCTTGGAAATTCCTT

AATGTTTATTAGCTTCTAACTAGTGTTGTAAGTCCGATGCCAGAATTTGGA

GATTTGAGTTCTTCTTTTCATGGCTTTTATTCACTGTGACTAATAAGCTTC

CTTGCCAGACTTAAAAAAAAAAA 3'

UC Band #332 (SEQ ID NO:34)

5'CGACTCGTCGCCATTCCCGGAGCAGGTCGGCCTCGGCCCAGGGGCGAGT

ATCCGTTGCTGTGTCGGAGACACTAGTCCCCGACACCGAGACAGCCAGCCC

TCTCCCCTGCCTCGCGGCGGGAGAGCGTGTCCGGCCGGCCGGCCGGCGGGG

CTCGCGCAACCTCCCTCGCCTCCCCTTCCCCGCAGCCTCCGCCCCGCCAG

GCCCGGCCCGGACTCCCGAGCCCCGGCCTCCTCGTCCTCGGTCGCCGCTGC

CGCCGGGCTTAACAGCCCCGTCCGCCGCTTCTCTTCCTAGTTTGAGAAGCC

AAGGAAGGAAACAGGGAAAAATGTCGCCATGAAGGCCGAGAACCGCTGCCG

CCGCCGACCCCCGCCGGCCCTGAACGCCATGAGCCTGGGTCCCCGCCGCGC

TABLE 6-continued

DNA SEQUENCES OF MARKERS OF
METASTATIC PROSTATE CANCER:

CCGCTCCGCTCCGACTGCCGTCGCCGCCGAGGCCCCCGTTGATGCCGCTGA

GCTCCCCCAACGCCGCCGCCACCGCCTCCGACATGGACAAGAACAGCGGCT

CCAACAGCTCCTCCGCCTCTTCGGGGCAGCAGCAAAGGGCAACAGCCGCCC

CGCTCCGCCTCGGCGGGGCCAGCCGGCGAGTCTAAACCCAAGAGCGAATTA

CTAATTTCAGCTGGATTCAATTTGTTGTCAGTTGATTCTGTAGTAAGGCCA

TATGTTGCCCCTCTGGAGGTGCTTGTCAACTCATCTGGATGATGGATGGAA

AGAACTCCAGTGGATCCAAGCGTTATAATCGCAAACGTGAACTTTCCTACC

CCAAAAATGAAAGTTTTAACAACCAGTCCCGTCGCTCCAGTTCACAGAAAA

GCAAGACTTTTAACAAGATGCCTCCTCAAAGGGGCGGCGGCAGCAGCAACT

CTTTAGCTCTTCTTTTAATGGTGGAAGACGAGATGAGGTAGCAGAGGCTCA

ACGGGCAGAGTTTAGCCCTGCCCAGTTCTCTGGTCCTAAGAAGATCAACCT

GAACCACTTGTTGAATTTCACTTTTGAACCCCGTGGCCAGACGGGTCACTT

TGAAGGCAGTGGACATGGTAGCTGGGGAAAGAGGAACAAGTGGGGACATAA

GCCTTTTAACAAGGAACTCTTTTTACAGGCCAACTGCCAATTTGTGGTGTC

TGAAGACCAAGACTACACTGCTCATTTTGCTGATCCTGATACATTAGTTAA

CTGGGACTTTGTGGAACAAGTGCGCATTTGTAGCCATGAAGTGCCATCTTG

CCCAATATGCCTCTATCCACCTACTGCAGCCAAGATAACCCGTTGTGGACA

CATCTTCTGCTGGGCATGCATCCTGCACTATCTTTCACTGAGTGAGAAGAC

GTGGAGTAAATGTCCCATCTGTTACAGTTCTGTGCATAAGAAGGATCTCAA

GAGTGTTGTTGCCACAGAGTCACATCAGTATGTTGTTGGTGATACCATTAC

GATGCAGCTGATGAAGAGGGAGAAAGGGGTGTTGGTGGCTTTGCCAAATCC

AAATGGATGAATGTAGACCATCCCATTCATCTAGGAGATGAACAGCACAGC

CAGTACTCCAAGTTGCTGCTGGCCTCTAAGGAGCAGGTGCTGCACCGGGTA

GTTCTGGAGGAGAAAGTAGCACTAGAGCAGCAGCTGGCAGAGGAGAAGCAC

ACTCCCGAGTCCTGCTTTATTGAGGCAGCTATCCAGGAGCTCAAGACTCGG

GAAGAGGCTCTGTCGGGATTGGCCGGAAGCAGAAGGGAGGTCACTGGTGTT

GTGGCTGCTCTGGAACAACTGGTGCTGATGGCTCCCTTGGCGAAGGAGTCT

GTTTTTCAACCCAGGAAGGGTGTGCTGGAGTATCTGTCTGCCTTCGATGAA

GAAACCACGGAAGTTTGTTCTCTGGACACTCCTTCTAGACCTCTTGCTCTC

CCTCTGGTAGAAGAGGAGGAAGCAGTGTCTGAACCAGAGCCTGAGGGGTTG

CCAGAGGCCTGTGATGACTTGGAGTTAGCAGATGACAATCTTAAAGAGGGG

ACCATTTGCACTGAGTCCAGCCAGCAGGAACCCATCACCAAGTCAGGCTTC

ACCGCCTCAGCAGCTCTCCTTGTTACTACTTTTACCAAGCGGAAGATGGAC

AGCATATGTTCCTGCACCCTGTGAATGTGCGCTGCCTCGTGCGGGAGTACG

GCAGCTGGAGAGGAGCCCCGAGAAGATCTCAGCAACTGTGGTGGCAGATT

GCTGGCTACTCCATGTCTGAGGATGTTCGACAGCGTCACAGATATCTCTCT

ACTTGCCACTCACCTGTGAGTTCAGCATCTGTGAACTGGCTTTGCAACCTC

CTGTGGTCTCTAAGGAAACCCTAGAGATGTTCTCAGATGACATTGAGAAGA

TABLE 6-continued

DNA SEQUENCES OF MARKERS OF METASTATIC PROSTATE CANCER:

```
GGAAACGTCAGCGCCAAAAGAAGGCTCGGGAGGAACGCCGCCGAGAGCGCA

GGATTGAGATAGAGGAGAACAAGAAACAGGGCAAGTACCCAGAAGTCCACA

TTCCCCTCGAGCCTCTACAGCAGTTTCCTGCCTTCAATTCTTATACCTGCT

CCCTGATTCTGCTTTGGGTCCCACCAGCACCGAGGGCCATGGGGCCCTCTC

CATTTCTCCTCTCAGCAGAAGTCCAGGTTCCCATGCAGACTTTCTGCTGAC

CCCTCTGTCACCCACTGCCAGTCAGGGCAGTCCCTCATTCTGCGTTGGGAG

TCTGGAAGAAGACTCTCCCTTCCCTTCCTTTGCCCAGATGCTGAGGGTTGG

AAAAGCAAAAGCAGATGTGTGGCCCAAAACTGCTCCAAAGAAAGATGAGAA

CAGCTTAGTTCCTCCTGCCCCTGTGGACAGCGACGGGGCGCGTGATAATTC

AGACCGTGTTCCTGTGCCCAGTTTTCAAAATTCCTTCAGCCAAGCTATTGA

AGCAGCCTTCATGAAACTGGACACACCAGCTACTTCAGATCCCCTCTCTGA

AGAGAAAGGAGGAAAGAAAAGAAAAAAACAGAACAGAAGCTCCTGTTCAGC

ACCTCAGTCGTCCACACCAAGTGACACTACTGGCCCAGGCTACCTTCTCCA

TCGGTTTTTGTTTTGTTTTTTTTCCCCCATGCTTTTGTTTGGCTGCTGT

AATTTTTAAGTATTTGAGTTTGAACAGATTAGCTCTGGGGGGAGGGGGTTT

CCACAAATGTGAGGGGGAACCAAGAAAATTTTAAATACAGTGTATTTCCAG

CTTCCTGTCTTTACACCAAAATAAAGTATTGACACAAGAG 3'
```

5.5 Example 5

Interleukin 8 (IL-8) mRNA and Protein is up Regulated in Peripheral Blood Leukocytes of Patients with Metastatic Prostate and Breast Cancer This Example compared the abundance of mRNA species in peripheral blood leukocytes of patients with advanced metastatic prostate cancer and healthy individuals to identify mRNAs whose steady state abundance varied between these physiologic states. The technique used to make this comparison was RNA fingerprinting using Arbitrarily Primed PCR™ (AP-PCR™) (Welsh et al., 1992). PCR™ amplified cDNA fragments from differentially expressed genes were cloned, and their DNA sequences were determined. One of the differentially appearing PCR™ amplified cDNA fragments was derived from the mRNA encoding the chemokine, interleukin-8 (IL-8) (Larsen et al., 1989; McClelland et al., 1994).

IL-8 mRNA specific oligonucleotide primers were synthesized and used in relative quantitative RT-PCR™ studies to independently confirm differential expression. Results from these relative quantitative RT-PCR™ studies demonstrated that IL-8 mRNA increases in abundance in the peripheral blood of patients with either metastatic prostate cancer or breast cancer. Based upon these IL-8 mRNA observations, the abilities of IL-8 serum derived protein, PSA serum concentrations and the f/tPSA ratio to detect and differentiate prostate cancers from BPH were compared. Finally, a multivariate algorithm that combined the information in both the IL-8 serum protein concentration and the f/tPSA ratio was also evaluated.

5.5.1 Patient Sample

The total of 193 serum specimens from normal men or men with a biopsy confirmed diagnosis of BPH or prostate cancer is summarized below in Table 7. All patients were biopsy-confirmed for either BPH or prostate carcinoma (stages A, B, and C only) within six months after PSA serum collection and/or a digital rectal exam (DRE)-positive diagnosis. Stage D patients were confirmed using standard radiological diagnostic techniques. All patient sera were obtained prior to any surgical or hormonal therapies. The mean age of the total sample was 69.4±8.6 years (range=37-91 years) old.

TABLE 7

SUMMARY OF PATIENT SAMPLE (N = 193)

| Diagnosis | N | Mean Age ± Std. Dev. (Range) |
|---|---|---|
| Normal | 8 | <50 years |
| BPH | 55 | 66.4 ± 8.6 (37-87) years |
| CaP Stage A | 24 | 74.7 ± 7.8 (61-91) years |
| CaP Stage B | 48 | 68.3 ± 7.9 (51-85) years |
| CaP Stage C | 15 | 68.9 ± 6.9 (60-80) years |
| CaP Stage D | 14 | 72.3 ± 8.6 (58-86) years |

5.5.2 Results

5.5.2.1 Relative Quantitative RT-PCR™

Using RNA fingerprinting, interleukin-8 mRNA was identified as being more abundant in the peripheral blood leukocytes of patients with metastatic prostate than in similar cells from healthy controls. It is preferred to independently confirm the differential regulation of mRNAs identified by RNA fingerprinting. For this purpose, a protocol for performing relative quantitative RT-PCR™ using pools of normalized cDNAs observed at increasing cycles of PCR™ was utilized to independently confirm the results of RNA fingerprinting.

For relative quantitative RT-PCR™ to be informative, it is necessary that the reactions be quantitated in the log-linear phase of the amplification curve. Using pools of normalized cDNA rather than cDNA from individuals reduces the numbers of samples sufficiently that amplifications can be observed over a range of PCR™ cycle numbers. This format provides direct demonstration of exponential increases in PCR™ product mass with increased cycle number as well as internal replication of data on the relative abundance of mRNA species. Other advantages of this format are that no prior knowledge about mRNA abundance or PCR™ efficiency is required. Also, no special equipment or specially modified oligonucleotides are required. Expenditures of time and resources needed to make gene specific PCR™ mimics are unnecessary, and many mRNAs can be examined in a single PCR™ run. Three different physiologic or disease states can be compared at four different PCR™ cycle numbers for six different candidate mRNAs or primer pairs plus appropriate controls in a single 96 well format. This protocol has permitted the screening of large numbers of mRNAs in a relatively short time span.

FIGS. 1A and 1B show the results of a relative quantitative RT-PCR™ study using primers that anneal to exons 3 and 4 of the IL-8 mRNA (FIG. 1A) and to the β-actin mRNA (FIG. 1B). Three pools of peripheral blood cDNA were examined. These pools were derived from healthy volunteers (n=8), patients with metastatic prostate cancer (n=10) and patients with metastatic breast cancer (n=10).

These pools of cDNA contained nearly equal quantities of amplifiable β-actin cDNA (FIG. 1B). This was determined not only from the similar intensities of the observed bands on the agarose gel but also from the relative increases in band intensities that are observed with increasing PCR™ cycle numbers. Uniformly increasing band intensity relative to PCR™ cycle number demonstrates that the PCR™ reactions are being observed while still in the log-linear range. Therefore, near equal band intensities indicate that the abundance of the β-actin cDNA is nearly equal in the various cDNA pools. The actual band intensities were quantitatively determined using the IS1000 Image Analysis System. Identical PCR™ reactions run in this way in different tubes varied in the intensity of their product bands with a standard deviation of less than ±15%.

The results of the relative quantitative RT-PCR™ for IL-8 (FIG. 1A) contrast sharply with those observed for β-actin (FIG. 1B). At lower cycle numbers, RT-PCR™ using primers that anneal to exons 3 and 4 of the IL-8 mRNA failed to detect a PCR™ product of the expected size in the peripheral blood of healthy volunteers. At these same lower cycle numbers, an abundant product of the expected size was clearly detected in peripheral blood RNAs of patients with metastatic breast or prostate cancer (FIG. 1A). This PCR™ product was excised from the gel, reamplified, cloned and sequenced as described above. The DNA sequence of this product was identical to the expected region of the published IL-8 mRNA sequence (Genbank numbers HSMDNCF and HUMMONAP). At higher cycle numbers, a PCR™ product of the expected size class began to appear in the cDNA pool from healthy volunteers, but the intensity of this band was still significantly less than for the metastatic prostate and breast cancer pools (FIG. 1A). Quantitation with the IS1000 Image Analysis System and normalization to the β-actin results indicate that the mRNA for IL-8 is about 15 fold more abundant in the peripheral blood of patients with either metastatic prostate or breast cancer compared to normal individuals.

Another advantage of relative quantitative RT-PCR™ using pools of cDNA observed at different cycle numbers is that the results show what cycle number RT-PCR™ could be performed at to examine differential mRNA abundance in the normalized cDNA from individuals. RT-PCR™ was performed at 25 cycles for IL-8 (FIG. 2A) and at 24 cycles for β-actin (FIG. 2B) for 10 individuals with metastatic prostate and 10 individuals with metastatic breast cancer, compared to a panel of normalized cDNAs from a pool of healthy volunteers (N). Amplification of β-actin cDNA shows that all of the cDNAs in this panel have roughly similar amounts of PCR™ amplifiable cDNA (FIG. 2B).

When oligonucleotides annealing to exons 3 and 4 of the IL-8 mRNA were used to prime PCR™ amplification for 25 cycles, a clearly visible band of expected size appeared in all lanes representing patients with metastatic cancer of the prostate or breast (FIG. 2A). No similar band was observed in lanes from the two duplicate PCR™ reactions derived from the pool of cDNAs from healthy volunteers (FIG. 2A, "N"). Compared to the healthy controls, IL-8 mRNA was more abundant in the peripheral blood of all twenty metastatic cancer patients examined (FIG. 2A). Variation in the abundance of IL-8 mRNA was observed among the individual cancer patients.

An unexpected result of the relative quantitative RT-PCR™ studies of IL-8 expression was the observation of a second PCR™ product in addition to the product of expected size. This band was excised from the gel, cloned and sequenced. Sequence data showed that this 592 basepair product is identical to a portion of the IL-8 gene sequence between the hybridization sites of the exon 3 and the exon 4 primers. It includes the entire sequence of IL-8 intron 3. RT-PCR™ studies with oligonucleotide primers that anneal to exons 2 and 4 demonstrated that this intron 3 containing product was reverse transcribed from an mRNA that includes intron 3 but from which intron 2 has been spliced out. Thus, intron 3 is an alternatively spliced intron within the IL-8 gene. This proposed alternative splicing has only a modest effect on the mature IL-8 polypeptide, resulting in only a four amino acid truncation at the C-terminal end.

5.5.2.2 IL-8 Serum Protein

Table 8 illustrates the distribution of total PSA levels, f/t PSA ratios, IL-8 levels, and age ranges for 193 test cases. Only the BPH, Stage A, Stage B, and Stage C prostate cancer patients were included in the univariate and multivariate statistical analysis. There was a statistically significant difference between all cancer stages and BPH (p<0001).

TABLE 8

SUMMARY OF SERUM BIOMARKERS (N = 193)

| | | Mean Value ± Std. Dev. | | |
|---|---|---|---|---|
| Diagnosis | N | UC325 (pg/ml) | Total PSA (ng/ml) | f/t PSA Ratio |
| Normal | 37 | 6.7 ± 3.8 | N/A | N/A |
| BPH | 55 | 6.8 ± 6.1 | 6.9 ± 4.0 | 21.9 ± 10.9% |
| CaP Stage A & B | 72 | 15.4 ± 10.1 | 7.9 ± 5.7 | 12.8 ± 7.7% |
| CaP Stage C | 15 | 19.1 ± 7.9 | 16.2 ± 7.6 | 11.2 ± 8.3% |
| CaP State D | 14 | 78.9 ± 197 | 244 ± 332 | 12.4 ± 7.1% |

Table 9 illustrates the diagnostic capability to differentiate prostate cancer and BPH using f/t PSA ratio at three different cutoffs. Table 9 also shows the diagnostic capability of IL-8 and t-PSA, analyzed at single Classification And Regression Tree (CART) selected cutoff points for the binary outcome of prostate cancer or BPH. A significant improvement, contributed by the IL-8 serum assay, was observed in both sensitivity and specificity of detecting clinically significant prostate cancer (FIG. 3). The combination of IL-8, treated as a continuous variable, and t-PSA or f/t PSA ratio provided a highly predictive multivariate test system to detect clinical stage A, B and C prostate cancer, without any interference from BPH. The best multivariate model combined f/t PSA with IL-8 detection. FIG. 4 shows a combination of Receiver Operator Characteristic (ROC) curves for total PSA, f/t PSA and IL-8+f/t PSA for the data set excluding state D cancers (n=142) to illustrate the contribution of each biomarker to the combined diagnostic model. It is clearly seen that the combination of IL-8 plus f/t PSA gave unexpectedly superior results compared with f/t PSA ratio or total PSA alone (FIG. 4).

TABLE 9

ABILITY OF SERUM TESTS TO DISCRIMINATE BPH VS. STAGE A, B, & C PROSTATE CANCER (N = 142).

| Serum Test | Cutoff* | Sensitivity | Specificity | AUC | p-value |
|---|---|---|---|---|---|
| f/t PSA Ratio | 11% | 52.9% | 91.9% | 0.7905 | <0.0001 |
| f/t PSA Ratio | 14% | 70.1% | 80.0% | " | " |
| f/t PSA Ratio | 20% | 85.1% | 47.3% | " | " |
| UC325 (IL-8) | 9.8 pg/ml | 72.4% | 74.5% | 0.7973 | <0.0001 |
| Total PSA | 14.8 ng/ml | 17.2% | 98.2% | 0.5995 | 0.0134 |
| f/t PSA & UC325 | 0.69** | 71.3% | 90.9% | 0.8784 | <0.0001 |

TABLE 9-continued

ABILITY OF SERUM TESTS TO DISCRIMINATE BPH VS.
STAGE A, B, & C PROSTATE CANCER (N = 142).

| Serum Test | Cutoff* | Sensitivity | Specificity | AUC | p-value |
|---|---|---|---|---|---|
| Total PSA & UC325 | 0.64** | 62.1% | 85.5% | 0.8069 | <0.0001 |

*All cutoff's determined using Classification and Regression Tree Analysis (CART)
**Predicated Probability value calculated using logistic regression function The data in Table 10 shows a relationship between tumor burden and IL-8 protein concentration using either a 10 pg/ml or 15 pg/ml cutoff. As the biopsy-confirmed clinical stage of the cancer increased, so did the IL-8 serum marker level. The same relationship was not observed with either t-PSA or f/t PSA ratio (data not shown).

TABLE 10

SERUM BIOMARKER DATASET: IL-8 VS. STAGING (N = 193)

| Specimen | | IL-8 (10 pg/ml Cutoff) | | IL-8 (15 pg/ml Cutoff) | |
|---|---|---|---|---|---|
| Stage | N | Negative | Positive | Negative | Positive |
| Normal | 37 | 8 (89%) | 4 (11%) | 37 (100%) | 0 (0%) |
| BPH | 55 | 41 (75%) | 14 (25%) | 50 (91%) | 5 (9%) |
| Stage A & B | 72 | 25 (35%) | 47 (65%) | 43 (60%) | 29 (40%) |
| Stage C | 15 | 0 (0%) | 15 (100%) | 5 (33%) | 10 (67%) |
| Stage D | 14 | 2 (14%) | 12 (86%) | 3 (21%) | 11 (79%) |

Table 11 shows correlation values for the different serum markers discussed above. It clearly shows that the IL-8 biomarker provides new information independent of that provided by the f/t PSA ratio (See IL-8 vs. f/t PSA correlation box).

TABLE 11

CORRELATION VALUES FOR BPH VS STAGES A, B & C
(N = 142)

| | Diagnosis | Total PSA (ng/ml) | f/t PSA Ratio (%) | UC325 (pg/ml) | Age | Clinical Stage |
|---|---|---|---|---|---|---|
| Diagnosis | 1.0000 | 0.5647 | −0.1912 | 0.2262 | 0.1590 | 0.3497 |
| Total PSA (ng/ml) | 0.5647 | 1.000 | −0.2319 | 0.5991 | 0.0898 | 0.3729 |
| f/t PSA Ratio (%) | −0.1912 | −0.2319 | 1.0000 | −0.2142 | 0.0641 | −0.4126 |
| UC325 (pg/ml) | 0.2262 | 0.5991 | −0.2142 | 1.0000 | 0.0881 | 0.2486 |
| Age | 0.1590 | 0.0898 | 0.0641 | 0.0881 | 1.0000 | 0.1372 |
| Clinical Stage | 0.3497 | 0.3729 | −0.4126 | 0.2486 | 0.1372 | 1.0000 |

Early in the investigation of IL-8, it became apparent that the detectable concentrations of IL-8 in serum samples decreased upon repeated freeze-thaw cycles. To quantitate this deterioration in signal, a set of patient sera was examined after one, two or three freeze and thaw cycles. FIG. 5 presents data on an average of twelve patient serum samples stored at −20° C. that were run on three separate occasions using the same lot of IL-8 assay microplates. The period of examination of these samples covered approximately three months. It is evident that IL-8 measurement is decreased by repeat freeze-thaw cycles and must be considered in any retrospective study using samples which have already undergone freeze-thaw. The data also attest to the relative instability of the soluble IL-8 molecule. Based upon this data, only sera that had been thawed once were used in the Example reported here.

The relative quantitative RT-PCR™ studies of Example 5 demonstrated that IL-8 mRNA increases in abundance in the peripheral blood of patients with either metastatic prostate cancer or breast cancer. Genes that were either up regulated or down regulated in blood from metastatic cancer patients were identified. One of the mRNAs identified as being more abundant in the peripheral blood of patients with metastatic prostate cancer was the cytokine interleukin-8 (IL-8) (Larsen et al., 1989). Hence, the immune system is an attractive choice to survey because it would be expected to respond robustly to a malignant disease process (Moreno et al., 1992). As such, by examining the peripheral blood mononuclear cell population, evidence of cancer presence was obtained without requiring any knowledge of its physical location in the body.

An immune response to a particular disease may be specific and definitive or it may be non-specific and generalized, but in either case it may be a valuable diagnostic tool for disease management. The host immune perturbations in cancer could be a useful prescreen or an enhancement of information complimenting other diagnostic procedures. In this Example, IL-8 mRNA expression was found to be up regulated as much as 15-fold (FIG. 1A and FIG. 2A) in peripheral blood leukocytes of both prostate and breast cancer patients. This observation provides a unique method to determine risk for the presence of metastasis by applying an RT-PCR™ assay for IL-8 mRNA to the peripheral blood of prostate or breast cancer patients.

IL-8 and total PSA both correlated to tumor burden and efficiently identified patients with metastatic stage D prostate cancer. While diagnosis of stage D prostate cancer is clinically important, potentially much greater benefit can be derived by patients who can be diagnosed with organ confined prostate cancer that can be effectively cured by surgery.

Total PSA is a relatively poor biomarker for organ confined prostate cancer because the relatively low concentrations of PSA in sera of patients with organ confined disease is frequently matched in patients with non-cancerous prostate conditions such as BPH (Jacobson et al., 1995; Partin and Oesterling, 1994; Babian et al., 1996; Zlotta et al., 1997; McCormack et al., 1995). Because BPH has a high prevalence in populations at risk for prostate cancer, many patients would benefit from a procedure that distinguishes PSA elevations caused by BPH and organ confined prostate cancer, a highly treatable disease.

The f/t PSA ratio is one diagnostic test that improves the differentiation of BPH from organ confined prostate cancer in patients with modestly elevated serum PSA levels (Ralph and Veltri, 1997; Christensson et al., 1993; Stenman et al., 1991; Lilja et al., 1991; Marley et al., 1996; Oesterling et al., 1995; Pettersson et al., 1995; Partin and Oesterling, 1996). BPH tissue tends to secrete a higher proportion of PSA in a molecular form that can not bind to protease inhibitors effectively and therefore is found free in the serum.

In this study a f/t PSA cutoff of 14% distinguished BPH from organ confined prostate cancer with a sensitivity of 70.1% and a specificity of 80.0%, confirming previous results (Marley et al., 1996; Oesterling et al., 1995). These values were compared with data obtained for IL-8 alone. Serum IL-8 concentrations were significantly more elevated in patients with stage A, B or C prostate cancer than in patients with BPH (p>0.0001). Using a cutoff of 9.8 pg/ml, IL-8 distinguished stage A, B, and C prostate cancer from BPH with a sensitivity of 72.4% and a specificity of 74.5%. These values indicate that f/t PSA and IL-8 serum concentrations distinguish BPH from stage A, B or C prostate cancer with approximately equal efficiency.

While both of these assays are informative in the diagnosis of organ confined prostate cancer, combining the information from these two tests into one diagnostic algorithm can make a substantial improvement in the prediction of outcome because the information provided by IL-8 is independent of that contributed by f/t PSA. By optimizing the combined information (FIG. 4) it was possible to distinguish prostate cancer from BPH with a sensitivity of 71.3% and a specificity of 90.9%. Clearly, this is a marked improvement over either test performed independently.

The present Example demonstrates a novel molecular RNA fingerprinting approach to surveying and identifying clinically relevant molecular changes in host immune response genes that occur during the process of malignancy. The peripheral blood fingerprinting approach may also be an important technique to apply to assessment of other chronic disease processes in addition to cancer. For example one might apply the approach to rheumatoid arthritis, autoimmune diseases, AIDS, chronic infectious diseases, chronic degenerative diseases of the central nervous system. The skilled artisan will recognize that application of these methods to detection or diagnosis of other such disease is contemplated within the scope of the instant invention.

5.6 Example 6

Two mRNAs with Conserved Sequence Motifs are Up Regulated in Nucleated Blood Cells of Patients with Metastatic Breast or Prostate Cancer RNA fingerprinting was performed as described in Section 4.12 above. Two additional differentially appearing PCR™ amplified cDNA fragments were identified in these studies, labeled as UC331 and UC332. UC331 was identified using a first promiscuous primer with the sequence 5'-ACGACTCACTATAAGCAGGA-3' (SEQ ID NO:13). The second promiscuous primer used was 5'-AACAGCTAT-GACCATCGTGG-3' (SEQ ID NO:23). UC332 was identified using a first promiscuous primer with the sequence 5'-ACGACTCACTATGTGGAGAA-3' (SEQ ID NO:24). The second promiscuous primer used was 5'-AACAGCTAT-GACCCTGAGGA-3' (SEQ ID NO:52). After autoradiography, bands that appeared differentially in fingerprinting reactions on the pooled total RNAs described above were cut out of the gels and reamplified by PCR™. The reamplified PCR™ products were directly sequenced using the Sequenase™ reagent system (Amersham Life Sciences, Inc., Arlington Heights, Ill.) The resulting sequences are reported as UC331 (SEQ ID NO:29) and UC332 (SEQ ID NO:34).

5.6.1 Comparison of UC331 and UC332 with Genbank

The sequences of UC331 and UC332 were compared to those deposited in release 101 of GenBank (July 1997) using the Lasergene™ software package (DNAstar, Inc., Madison, Wis.). UC331 was identical within the limits of sequencing accuracy to several human EST sequences. These human EST sequences were used to construct a virtual contig. The two ends of this virtual contig were then used to query Genbank again.

Additional, human ESTs were identified that could be used to extend the length of the virtual contig. This process was repeated several times until the poly-A tail and an open reading frame (ORF) were identified. The human ESTs used to construct this virtual contig are described in Table 12. Sequences within the ORF of the human virtual 331 contig demonstrated high similarity to numerous mouse EST sequences. These mouse EST sequences were used to construct a virtual contig in a process that was identical to that used to create the human contig. The mouse ESTs used to construct the mouse virtual contig are described in Table 13. The mouse contig encoded an ORF that was highly similar to the one observed in the human contig. The amino acid sequence of the human UC331 ORF was used to query the Swiss, PIR and Translation release 101 using the Lasergene™ software package.

TABLE 12

| GB Accession Number | UC331 EST Distribution Human | |
|---|---|---|
| | Tissue | Library |
| AA403120 | Total Fetus | Soares |
| AA401845 | Total Fetus | Soares |
| AA121473 | Pregnant Uterus | Soares |
| AA121262 | Pregnant Uterus | Soares |
| R22145[i] | Placenta | Soares |
| R22146[i] | Placenta | Soares |
| R30954[i] | Placenta | Soares |
| R31006[i] | Placenta | Soares |
| R32887[h] | Placenta | Soares |
| R31390[h] | Placenta | Soares |
| R67806[g] | Placenta | Soares |
| R67807[g] | Placenta | Soares |
| AA385620 | Thyroid | TIGR |
| W37985 | Parathyroid Tumor | Soares |
| W37986 | Parathyroid Tumor | Soares |
| AA380401 | Cell line (Supt) | TIGR |
| AA182471 | Cell line (HeLa) | Stratagene (IMAGE) |
| AA181530 | Cell line (HeLa) | Stratagene (IMAGE) |
| W31231 | Senescent Fibroblasts | Soares |
| N22701 | Normal Melanocyte | Soares |
| N31175 | Normal Melanocyte | Soares |
| N34446 | Normal Melanocyte | Soares |
| N34538 | Normal Melanocyte | Soares |
| N36424 | Normal Melanocyte | Soares |
| N36521 | Normal Melanocyte | Soares |
| N42854 | Normal Melanocyte | Soares |
| N44299 | Normal Melanocyte | Soares |
| W56398 | Normal Melanocyte | Soares |
| N66813 | Normal Melanocyte | Soares |
| AA379996 | Skin Tumor | TIGR |
| AA370040 | Prostate Gland | TIGR |
| AA369851 | Prostate Gland | TIGR |
| H08822[k] | Brain (Whole infant) | Soares |
| H08905[k] | Brain (Whole infant) | Soares |
| H19533 | Brain (Whole Adult) | Soares |
| H21379[f] | Brain (Whole Adult) | Soares |
| H21421[f] | Brain (Whole Adult) | Soares |
| H24360[e] | Brain (Whole Adult) | Soares |
| H25176[e] | Brain (Whole Adult) | Soares |
| H38689 | Brain (Whole Adult) | Soares |
| H38791 | Brain (Whole Adult) | Soares |
| H39147[d] | Brain (Whole Adult) | Soares |
| H39148[d] | Brain (Whole Adult) | Soares |
| H45092[c] | Brain (Whole Adult) | Soares |
| H45054[c] | Brain (Whole Adult) | Soares |
| H49928 | Brain (Whole Adult) | Soares |
| H50463 | Brain (Whole Adult) | Soares |
| H51403[a] | Brain (Whole Adult) | Soares |
| H51444[a] | Brain (Whole Adult) | Soares |
| H52811[b] | Brain (Whole Adult) | Soares |
| H52774[b] | Brain (Whole Adult) | Soares |
| R85542 | Brain (Whole Adult) | Soares |
| R84652 | Brain (Whole Adult) | Soares |
| AA324855 | Brain (Cerebellum) | TIGR |

TABLE 12-continued

UC331 EST Distribution
Human

| GB Accession Number | Tissue | Library |
|---|---|---|
| AA317211 | Retina | TIGR |
| AA371911 | Pituitary Gland | TIGR |
| AA302113 | Endothelial Cells, Aorta | TIGR |
| AA247643 | Fetal Heart | U. Toronto |
| W60049 | Fetal Heart | Soares |
| W61359 | Fetal Heart | Soares |
| AA243511 | B-Cells | Soares |
| AA234769 | Pooled; fetal heart, melanocytes, pregnant uterus | Soares |
| AA158239 | Pancreas | Stratagene (IMAGE) |
| AA150585 | Pancreas | Stratagene (IMAGE) |
| AA160836 | Pancreas | Stratagene (IMAGE) |
| H73822 | Fetal Liver Spleen | Soares |
| N58180 | Fetal Liver Spleen | Soares |
| W04414 | Fetal Liver Spleen | Soares |
| N94254 | Fetal Liver Spleen | Soares |
| N75996 | Fetal Liver Spleen | Soares |
| N69644 | Fetal Liver Spleen | Soares |
| T83329 | Fetal Liver Spleen | Soares |
| T72755 | Fetal Liver Spleen | Soares |
| T53976 | Pooled Fetal Spleens | Soares |
| N76701 | Multiple Sclerosis | Soares |
| N90814 | Multiple Sclerosis | Soares |
| N63292 | Multiple Sclerosis | Soares |
| N59233 | Multiple Sclerosis | Soares |
| N53207 | Multiple Sclerosis | Soares |
| N51545 | Multiple Sclerosis | Soares |
| F22624 | Skeletal Muscle. | CRIBI (Italy) |

Note: Paired superscripts indicate opposite ends of the same cDNA clone.

TABLE 13

UC331 EST Distribution
Mouse

| GB Accession Number | Tissue | Library | Clone # |
|---|---|---|---|
| AA027487 | Placenta | Soares | 459407 (5') |
| AA023708 | Placenta | Soares | 456984 (5') |
| AA023154 | Placenta | Soares | 456027 (5') |
| AA024303 | Placenta | Soares | 458313 (5') |
| W35948 | Total Fetus | Soares | 350258 (5') |
| W11581 | Total Fetus | Soares | 318665 (5') |
| W36820 | Total Fetus | Soares | 336707 (5') |
| AA002492 | Mouse Embryo | Soares | 426498 (5') |
| AA097370 | Mouse Embryo | Soares | 493073 (5') |
| AA014313 | Mouse Embryo | Soares | 468491 (5') |
| AA450512 | Beddington embryonic region | IMAGE | 865186 (5') |
| AA408179[L] | Embryo Ectoplacental Cone | Ko | C0025F09 (3') |
| AA408261[L] | Embryo Ectoplacental Cone | Ko | C0025F09 (5') |
| AA117174 | T-cells | Stratagene | 558134 (5') |
| AA119346 | Thymus | Soares | 573567 (5') |
| AA183195 | Lymph Node | Soares | 636222 (5') |
| AA122933 | Kidney | Barstead | 579415 (5') |
| AA423613 | Mammary Gland | Soares | 832219 (5') |

Note: Paired superscripts indicate opposite ends of the same cDNA clone.

To confirm that the human UC331 virtual contig accurately represented the sequence of an authentic mRNA, oligonucleotides were designed to direct the PCR™ amplification of large cDNA fragments predicted to be continuous from the virtual contig but which contain significantly more sequence than can be found in any single EST.

UC332 did not match any EST sequences but was identical to a portion of a previously sequenced full length cDNA with a GenBank accession number of D87451.

5.6.2 Relative Quantitative RT-PCR™

Approximately 1.5-5.0 µg of DNA-free total RNA from the peripheral blood of healthy volunteers or patients with either metastatic prostate or breast cancer were analyzed by relative quantitative RT-PCR as described in section 4.11.3 above. Typically, the cDNA derived from the reverse transcription of 5.0 µg of RNA resulted in enough normalized cDNA to perform 50-200 RT-PCR™ reactions.

The oligonucleotides used in the relative quantitative RT-PCR™ studies that independently confirmed the differential expression of UC331 were designed from the sequence in the human UC331 virtual contig. These UC331 specific oligonucleotides had the sequences of 5' CTGGCCTACGGAAGATACGACAC 3' (SEQ ID NO:25) and 5' ACAATCCGGAGGCATCAGAAACT 3' (SEQ ID NO:26). These oligonucleotides direct the amplification of a 277 nucleotide long PCR™ product that is specific for UC331.

The oligonucleotides used in the relative quantitative RT-PCR™ studies that independently confirmed the differential expression of UC332 were designed using the sequences of the cDNA with the GenBank accession number D87451. These UC332 specific oligonucleotides had the sequences 5' AGCCCCGGCCTCCTCGTCCTC 3' (SEQ ID NO:27) and 5' GGCGGCGGCAGCGGTTCTC 3' (SEQ ID NO:28). These oligonucleotides direct the amplification of a 140 nucleotide long PCR™ product that is specific for UC332.

5.6.3 Results

In this Example, RNA fingerprinting identified two cDNA fragments derived from mRNA species that had higher steady state abundances in the peripheral blood leukocytes of patients with recurrent metastatic prostate cancer as compared to a group of healthy volunteers. The DNA sequence of these cDNA fragments, when compared to the Genbank database, revealed that the mRNAs, from which these cDNA fragments were derived, were previously uncharacterized. For purposes of discussion, these two mRNAs and the genes from which they were transcribed were given the arbitrary designations UC331 and UC332.

5.6.3.1 UC331

While neither UC331 nor UC332 are genes whose products have been previously characterized as being significant in any physiological pathway, both UC331 and UC332 match sequences on the GenBank database. In the case of UC331, these matches are confined to ESTs. The human EST sequences with high similarity to UC331 could be assembled into a virtual contig that predicts the sequence of a larger mRNA. The ends of the UC331 contig were then used to requery the EST data base whereby more ESTs were identified that extended the contig. This process was continued until the UC331 contig predicted a mRNA with an ORF and a poly-A tail. A description of the human ESTs that were used to construct the UC331 contig are provided in Table 12. The sequence of the UC331 contig (SEQ ID NO:29) and the ORF are presented in FIG. 6A, FIG. 6B, FIG. 6C, FIG. 6D, and FIG. 6E.

When the human UC331 contig was used to query the GenBank database many mouse EST sequences were identified with significant similarity. This was especially true in the region spanning the putative ORF. The identified mouse ESTs were found to have areas of overlap and similarity with each other that permitted them to be assembled into a mouse UC331 virtual contig (SEQ ID NO:30). The mouse UC331 virtual contig was observed to have an ORF at its 5' end and a poly-A tail at its 3' end. A description of the mouse ESTs that were used to construct this contig are provided in Table 13.

When the MegAlign™ program of the Lasergene™ DNA analysis software package (DNAstar, Inc.) was used to compare the mouse and human UC331 contigs, the two contigs were predicted to represent mRNA species that were highly similar and nearly collinear throughout their lengths. This similarity was most striking in the region comprising the putative ORFs. Within the ORFs the mouse and human contigs, the DNA sequences are 89% identical. In the predicted 3' untranslated regions of the two contigs, the DNA sequence similarity falls to 73% with several small deletions and insertions.

This higher degree of sequence similarity in the putative ORFs as compared to the proposed 3' untranslated region is interpreted as evidence that the ORFs encode proteins on which natural selection constrains amino acid sequence divergence. The DNA sequence comparison of these two contigs is shown in FIG. 6A, FIG. 6B, FIG. 6C, FIG. 6D, and FIG. 6E. Unlike the human UC331 contig, the mouse contig also encodes a putative ORF that extends all the way to its 5' end. This provides additional support for the contention that the mouse UC331 mRNA contains more sequences at its 5' end than are represented by the EST based contigs presented here.

The ORFs of the mouse and human UC331 contigs were conceptually translated and the amino acid sequences were compared (SEQ ID NO:32 and SEQ ID NO:31, respectively). For the 157 amino acids for which this comparison is possible, the mouse and human sequences are collinear and identical at 151 positions (96%) with five of the six differences being conservative substitutions. This putative protein domain is highly acidic with 26 acidic and 17 basic amino acids. There were also 48 hydrophobic and 41 polar amino acids predicted.

When either the predicted mouse or human UC331 amino acid sequences was compared to amino acid sequences in the public protein sequence data bases, no significant matches were found to any previously characterized vertebrate proteins. However, a significant match was observed to a putative protein, termed ZK353.1 (PIR Accession number S44654; SEQ ID NO:33), encoded in the genome of the nematode, Caenorhabditis elegans. The mammalian amino acid sequence is similar and collinear with the C-terminal 157 amino acids of the putative C. elegans protein. Like the mammalian UC331 amino acid sequences, the C-terminal 157 amino acid sequence of the ZK353.1 is also highly acidic with 31 acidic and only 20 basic amino acids. A comparison of these three amino acid sequences is shown in FIG. 7.

The putative C. elegans protein, ZK353.1, has no currently known function. Its existence is predicted from the C. elegans genome sequencing effort (Sulston et al., 1992). The polypeptide sequence for ZK353.1 is a conceptual translation of an area on the C. elegans chromosome III (GB accession number CELZK353). The predicted sequence for ZK353.1 is 548 amino acids long and includes an additional 337 amino acids that are N-terminal of the domain with similarity to the predicted amino acid sequence of UC331. This may indicate an error in interpreting the possible pattern of mRNA processing from the C. elegans sequence or indicate simply that the mammalian and nematode mRNAs and encoded proteins are significantly different from each other at their 5' and N-terminal ends respectively.

Frequently, mRNAs identified by RNA fingerprinting or differential display as being differentially regulated turn out not to be so when examined by independent means. It is, therefore, critical that the differential expression of all mRNAs identified by RNA fingerprinting be confirmed as such by an independent methodology. To independently confirm the differential expression of UC331 in the peripheral blood of patients with recurrent metastatic cancer compared to the peripheral blood of healthy volunteers, two different formats for a relative quantitative RT-PCR™ were performed.

The first format of this assay examined normalized pools of cDNA constructed by combining equal amounts of cDNA from various individuals representing similar physiologic states. In this study, a cDNA pool representing 8 healthy volunteers was compared to a pool representing 10 individuals with recurrent metastatic prostate cancer. A third pool representing 10 individuals with recurrent metastatic breast cancer was also examined. The inclusion of the breast cancer patient samples in this study was made to determine if the mRNAs examined were being differentially regulated in the immune system in a response that was specific for prostate cancer or if the response was more general to metastatic cancer in general.

Using these pools of cDNA as templates, triplicate PCR™ was performed. Each of the three replicates were terminated at a different cycle number of PCR™. This format of relative quantitative RT-PCR™ insures that the results taken for relative quantitation represent the PCRs™ when they are in the log linear portions of their amplification curves where such quantitation is most accurate. The resulting PCR™ amplified β-actin products were visualized by gel electrophoresis and staining with ethidium bromide. Images of these gels were captured and quantitated using the IS-1000 Digital Imaging System (Alpha Innotech, Inc.).

FIG. 8A shows the results of a relative quantitative RT-PCR™ using the cDNA pools describe above as templates and oligonucleotide primers specific for cDNA that was reverse transcribed from the β-actin mRNA. At all three cycle numbers examined, there are relatively similar band intensities representing the three cDNA pools and increasing band intensity with increasing cycle number. These results show that the three examined cDNA pools contain roughly similar concentrations of amplifiable β-actin cDNA.

The results for relative levels of β-actin expression contrasts sharply with those observed when oligonucleotide primers specific for UC331 were used to direct PCR™ amplification (FIG. 8B). At 25 cycles of PCR™, clear bands are visible in the lanes representing the pools of cDNA from peripheral blood of patients with either metastatic breast or prostate cancer. In the lane representing the peripheral blood of healthy volunteers, only a very faint band is present. At 28 cycles of PCR™, the band intensities representing all three pools are brighter than they were at 25 cycles, but the relative increase in intensity of the bands representing the metastatic cancer patient pools compared to the healthy volunteers remains the same as was observed at 25 cycles of PCR™. This indicates that these observations are being made in the log linear range of the PCR™ amplification curves. At 31 cycles of PCR™, there is still an increase in the intensity of the bands representing the pools of metastatic cancer patients compared to the pool representing the healthy volunteers, but a quantitative analysis of these bands indicates that the PCRs™ have left the log linear range of their amplification curves.

Quantitation of the data for 25 and 28 cycles of PCR™ independently confirms that UC331 mRNA is differentially regulated and is roughly seven fold more abundant in the peripheral blood leukocytes of the average patient with either recurrent metastatic prostate cancer or breast cancer than in the peripheral blood leukocytes of healthy volunteers.

Relative quantitative RT-PCR™ was used to examine the differential expression of UC331 by comparing the relative abundance of UC331 mRNA in the peripheral blood of healthy individuals or individuals with recurrent metastatic cancer. The individuals examined in this study were the same as those whose cDNAs were combined to construct the pools examined as described above. Using the information obtained from the pooled cDNA study to predict at what PCR™ cycle numbers relative quantitative RT-PCR™ would be most informative, these individuals were examined for the relative abundance of β-actin and UC331 mRNAs present in their peripheral blood leukocytes. The results for the β-actin amplifications are shown in FIG. 9A. All individuals examined contain roughly equal amounts of amplifiable β-actin cDNA. Some of the differences in β-actin band intensity observed in this study are probably due to the internal variation inherent of this study. Results from studies designed to quantitate this internal variation indicate that identical replicates of a β-actin PCR™ can be expected to vary in the intensity of product bands with a standard deviation of ±15%.

As was seen in the study using the pooled cDNAs, the results of the relative quantitative RT-PCR™ for UC331 using cDNA from individuals contrasts sharply with that observed for β-actin. As shown in FIG. 9B, the intensity of the band representing the abundance of the UC331 mRNA in peripheral blood leukocytes was greater for all of the patients with either metastatic prostate or breast cancer as compared to the intensity of the UC331 band representing the mRNA level in the peripheral blood leukocytes of healthy volunteers. Therefore, the elevated UC331 mRNA levels indicated by the relative quantitative RT-PCR™ results using the pooled cDNA templates was caused by an elevated mRNA level in all individuals comprising the pools and not from a subset of individuals with very high elevations in UC331 mRNA levels. This study is a second independent confirmation of the differential expression of the UC331 mRNA.

As is indicated by the wide distribution of tissues from which the ESTs used to assemble the UC331 contigs (Tables 12 and 13), UC331 is widely expressed in many tissue and cell types. However, because most of ESTs comprising UC331 are from normalized libraries, little information can be gained from this data on the relative abundance of the UC331 mRNA in different tissues.

To address all of these issues, a Northern blot of poly-A plus RNA from eight different human tissues was probed with the 850 nucleotide long RT-PCR™ product described above labeled with $^{32}$P. An image of the resulting autoradiograph is shown in FIG. 10. FIG. 10 shows that UC331 mRNA is expressed in all eight human tissue and cell types. Interestingly, UC331 is least abundant in peripheral blood leukocytes but is highly expressed in the thymus. The significance of this difference in expression between cells of different developmental stages in the immune system invites further study. UC331 is most abundantly expressed in the testes.

5.6.3.2 UC332

The other gene identified as being differentially regulated in this RNA fingerprinting study was UC332. UC332 was analyzed in much the same way as UC331 was. When the sequence of the cDNA fragment from the RNA fingerprinting gel representing UC332 was used to query GenBank, no ESTs were identified. The sequence of the UC332 cDNA fragment did, however, identify a sequence of a full length cDNA, KA000262 (GB: accession number D87451; SEQ ID NO:34). The sequence of KA000262, (hereafter referred to interchangeably with the name, UC332) was determined as part of a project to examine previously unidentified mRNAs expressed in the bone marrow myeloblast cell line, KG-1 (Nagase et al., 1996). This mRNA contains an ORF encoding a putative protein with 761 amino acid sequence (FIG. 11A, FIG. 11B, FIG. 11C, and FIG. 11D; SEQ ID NO:35). Perhaps the most striking feature of this polypeptide sequence is the appearance of a C3HC4 RING zinc finger or RING finger motif (Freemont, 1993) located between amino acids 175 and 216.

The RING finger domain binds two zinc ions in a conserved structure that has been resolved (Barlow et al., 1994). RING finger domains have been identified in dozens of proteins derived from eukaryotes as diverse as yeasts, flies, birds, nematodes and humans. In most of these cases, the RING finger containing proteins have been shown to be essential for some important biological process although these processes vary considerably one from another. A comparison of the RING finger domains of UC332 and various representative members of this group of proteins is shown in FIG. 12.

Proteins with RING finger motifs exhibit heterogeneity in their subcelluar localizations. Some, that are important regulators of differential gene regulation, localize to the cell nucleus. When the amino acid sequence of UC332 was scanned for evidence of subcellular localization, two domains were identified that contained sequences for putative nuclear localization signals (NLS). NLS are highly basic stretches of six are more amino acids of which at least four are basic that tend to be flanked by acidic amino acids and/or prolines (Boulikas, 1994). Both of the putative NLS in UC332 longer and more basic than the minimum requirements for the consensus NLS motif (FIG. 11A, FIG. 11B, FIG. 11C, and FIG. 11D).

The first of these putative NLS motifs occurs between amino acid 548 and 567. Within this domain, 13 of 19 amino acids are basic. In fact, this domain could be viewed as two NLS in tandem separated by two glutamic acid residues. If divided this way, the first NLS domain would have 8 of eleven positions as basic amino acids while the second motif would have 5 of 6 amino acids being basic. The second NLS motif in UC332 is located near the C-terminal end between positions 739 and 750 in the amino acid sequence. This domain has 8 of 12 amino acids as basic residues with a core of 5 consecutive lysines and arginines. The presence of these putative NLS in the amino acid sequence of UC332 suggest the possibility that UC332 plays an important role in regulating the expression of other genes. Finally, the amino acid sequence of UC332 lacks a signal sequence for cellular export or an obvious hydrophobic transmembrane domains.

To independently verify that UC332 mRNA is more abundant in the peripheral blood leukocytes of patients with recurrent metastatic cancer as compared to the peripheral blood leukocytes of healthy volunteers, relative quantitative RT-PCR™ was performed using the same cDNAs and formats as were used to investigate the differential regulation of UC331. FIG. 13A shows the results of a relative quantitative RT-PCR™ study using UC332 specific oligonucleotide primers and cDNA pools as templates. At 25 and 28 cycles of PCR™, the amplified DNA band representing the relative abundance of the UC332 mRNA is stained more intensely for those reactions that used cDNA template pools constructed from the peripheral blood leukocyte RNA isolated from metastatic prostate and breast cancer patients as compared to a similar pool constructed from RNA from healthy volunteers. Quantitation of this image using the IS-1000 Digital Imaging System (Alpha Innotech, Inc.) indicates that UC332 mRNA is roughly 5 times more abundant in the peripheral blood leukocytes of metastatic cancer patients compared to healthy volunteers. At 31 cycles of PCR™, the reactions have left the log linear range of their amplification curves.

In a second relative quantitative RT-PCR™ study using UC332 specific oligonucleotide primers, peripheral blood leukocyte cDNA from the individuals that comprised the pools were examined separately. As shown in FIG. 13B, the results of this study are similar to those obtained when the pooled cDNAs were used as PCR™ templates. All of the cancer patients had higher levels of UC332 mRNA in their peripheral blood leukocytes than did any of the healthy volunteers.

All of the compositions and methods disclosed and claimed herein may be made and executed without undue experimentation in light of the present disclosure. While the compositions and methods of this disclosure have been described in terms of preferred embodiments, it is apparent that variations may be applied to the composition, methods and in the steps or in the sequence of steps of the method described herein without departing from the concept, spirit and scope of the invention.

More specifically, it is apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

5.7 Example 7

The mRNA for IL-10 is also Upregulated in Metastatic Prostate or Breast Cancers

Probes designed to specifically amplify the mRNA product of the IL-10 gene were designed (SEQ ID NO:14 and SEQ ID NO:47) and utilized for relative quantitative RT-PCR™ studies, using the same protocols described above for the IL-8 gene. Samples of peripheral blood from individuals with metastatic prostate or breast cancer were as described for IL-9 above. Results of relative quantitative RT-PCR™ showed that IL-10 is upregulated in the peripheral blood of patients with metastatic cancers of prostate or breast to the same degree as IL-8 (FIG. 14). As shown in FIG. 14, the IL-10 gene product is consistently present in higher amounts in pooled samples from the peripheral blood of patients with metastatic prostate cancer (lanes 4, 8, 12) or breast cancer (lanes 5, 9, 13) compared to two different pools of peripheral blood from normal individuals (lanes 2, 3, 6, 7, 9, 10). This was true after 30 cycles of amplification (lanes 2-5), 32 cycles (lanes 6-9) or 34 cycles (lanes 10-13). Thus, detection and diagnosis of malignant cancers may be accomplished by measuring gene products of IL-10 in peripheral blood, as described above for IL-8. The skilled artisan will realize that IL-10 expression may be determined by assays directed towards either nucleic acid products or encoded protein or polypeptide products of the IL-10 gene.

6.0 REFERENCES

The following references, to the extent that they provide exemplary procedural or other details supplementary to those set forth herein, are specifically incorporated herein by reference.

Abbondanzo et al., *Breast Cancer Res. Treat.*, 16: 182 (#151), 1990.
Adams et al., *Science*, 252:1651-1656, 1991.
Adams, et al., *Nature* 377: *Supplement: The Genome Directory*, pages 3-174, 1995.
Alcaraz et al., *Cancer Res.*, 55:3998-4002, 1994.
Allhoff et al., *World J. Urol.*, 7:12-16, 1989.
Allred et al., *Breast Cancer Res. Treat.*, 16:182(#149), 1990.
American Cancer Society—Facts and Figures—1998, http://www.cancer.org/statistics/98cff/98prosta.html.
An et al., *Proc. Amer. Assn. Canc. Res.*, 36:82, 1995.
Andrawis et al., *Proc. Am. Urol. Assn.* 155(5): 512A, 1996.
Antibodies: A Laboratory Manual, Cold Spring Harbor Laboratory, Cold Spring Harbor Press, Cold Spring Harbor, N.Y., 1988.
Babian et al., *J. Urol.*, 156:432-437, 1996.
Baichwal and Sugden, In: *Gene Transfer*, Kucherlapati R, ed., New York, Plenum Press, pp. 117-148, 1986.
Barinaga, *Science*, 271: 1233, 1996.
Barlow et al., *J. Mol. Biol.*, 237:201-211, 1994.
Barry et al., *Urology*, 46:2-14, 1995.
Beck, Kattan and Miles, *J. Urol.*, 152:1894-99, 1994.
Bellus, *J. Macromol. Sci. Pure Appl. Chem*, A31(1): 1355-1376, 1994.
Benvenisty and Neshif, *Proc. Nat. Acad. Sci. USA*, 83:9551-9555, 1986.
Bittner et al., *Methods in Enzymol*, 153: 516-544, 1987.
Bookstein et al., *Proc. Nat'l Acad. Sci. USA*, 87:7762-7767, 1990b.
Bookstein et al., xScience, 247:712-715, 1990a.
Boring et al., *CA-Cancer J. Pract.*, 43:7-26, 1993.
Boulikas, *J. Cell. Biol.*, 55:32-58, 1994.
Bova et al., *Cancer Res.*, 53:3869-3873, 1993.
Brawn et al., *The Prostate*, 28: 295-299, 1996.
Breiman, Friedman, Olshen, Stone, In: *Classification and Regression Trees*, Pacific Grove, Wadsworth, 1984.
Brown et al., *Breast Cancer Res. Treat.*, 16:192(#191), 1990.
Campbell, In: *Monoclonal Antibody Technology, Laboratory Techniques in Biochemistry and Molecular Biology*, Burden and Von Knippenberg, Eds., Vol. 13:75-83, Elsevier, Amsterdam, 1984.
Capaldi et al., *Biochem. Biophys. Res. Comm.*, 76: 425, 1977
Carter and Coffey, In: *Prostate Cancer: The Second Tokyo Symposium*, J. P. Karr and H. Yamanak (eds.), pp. 19-27, New York: Elsevier, 1989.
Carter and Coffey, *Prostate*, 16:3948, 1990.
Carter et al., *Proc. Nat'l Acad. Sci. USA* 93: 749-753, 1996.
Carter et al., *Proc. Nat'l Acad. Sci. USA*, 87:8751-8755, 1990.
Carter et al., *J. Urol.*, 157:2206-2209, 1997.
Catalona et al., *J. Urol.*, 151:1283-1290, 1994.
Catalona et al., *J.A.M.A.*, 274:1214, 1995.
Chang et al., *Hepatology*, 14: 124A, 1991.
Chen and Okayama, *Mol. Cell Biol.*, 7:2745-2752, 1987.
Chen et al., *Clin. Chem.*, 41:273-282, 1995.
Chen et al., *Proc. Am. Urol. Assn.*, 153:267A, 1995.
Chinault and Carbon, *Gene*, 5:111-126, 1979.
Chomczynski and Sacchi, *Anal. Biochem.*, 162: 156-159, 1987.

Christensson et al., *J. Urol.*, 150:100-105, 1993.
Coffin, In: *Virology*, Fields et al., eds., Raven Press, New York, pp. 1437-1500, 1990.
Colberre-Garapin et al., *J. Mol. Biol.*, 150:1, 1981.
Cooner et al., *J. Urol.*, 143:1146-1154, 1990.
Coupar et al., *Gene*, 68:1-10, 1988.
Damaj et al., *FASEB J.* 10: 1426-1434, 1996.
Davey et al., EPO No. 329 822.
Dbom, *J. Cancer Res. Clin. Oncol.*, 106:210-218, 1983.
di Celle et al., *Blood*, 84: 220-228, 1994.
Diamond et al., *J. Urol.*, 128: 729-734, 1982.
Donahue et al., *J. Biol. Chem.*, 269:8604-8609, 1994.
Dong et al., *Science*, 268: 884-886, 1995.
Dubensky et al., *Proc. Nat. Acad. Sci. USA*, 81:7529-7533, 1984.
Dugan et al., *J.A.M.A.*, 275(4):288-294, 1996.
Dumont et al., *J. Immunol.*, 152:992-1003, 1994.
Everett et al., *J. Virology*, 69:7339-7344, 1995.
Fechheimer et al., *Proc. Natl. Acad. Sci. USA*, 84:8463-8467, 1987.
Ferkol et al., *FASEB J.*, 7:1081-1091, 1993.
Fraley et al., *Proc. Natl. Acad. Sci. USA*, 76:3348-3352, 1979.
Freemont, *Ann. N.Y. Acad. Sci.*, 684:174-192, 1993.
Friedmann, *Science*, 244:1275-1281, 1989.
Freifelder, *Physical Biochemistry Applications to Biochemistry and Molecular Biology*, 2nd ed., Wm. Freeman and Co., New York, N.Y., 1982.
Freshner, *Animal Cell Culture: A Practical Approach*, 2nd ed., Oxford/New York, IRL Press, Oxford University Press, 1992.
Fridell et al., *Virology*, 209:347-357. 1995.
Frohlich et al., *Molec. Cell. Biol.*, 10:3216-3223, 1990.
Frohman, *PCR PROTOCOLS: A GUIDE TO METHODS AND APPLICATIONS*, Academic Press, N.Y., 1990.
Fujichima et al., *Cytometry*, 24:382-389, 1986.
Garnick, *Scientific Amer.* 270: 72-81, 1994.
Gefter et al., *Somatic Cell Genet.*, 3: 231-236, 1977.
Ghosh-Choudhury et al., *EMBO J.*, 6:1733-1739, 1987.
Gingeras et al., PCT Application WO 88/10315.
Goding, In: *Monoclonal Antibodies: Principles and Practice*, 2d ed., Orlando, Fla., Academic Press, pp. 60-61, 65-66, 71-74, 1986.
Gomez-Foix et al., *J. Biol. Chem.*, 267:25129-25134, 1992.
Gopal, *Mol. Cell Biol.*, 5:1188-1190, 1985.
Graham et al., *J. Gen. Virol.*, 36:59-72, 1977.
Graham and van der Eb, *Virology*, 52:456-467, 1973.
Graham and Prevec, In: *Methods in Molecular Biology: Gene Transfer and Expression Protocols* 7, E. J. Murray (ed.), Clifton, N. J., Humana Press, pp. 205-225. 1991.
Grunhaus and Horwitz, *Seminar in Virology*, 3:237-252, 1992.
Harland and Weintraub, *J. Cell Biol.*, 101:1094-1099, 1985.
Harris et al., *J. Urol.*, 157:1740-1743, 1997.
Haupt et al., *Cell*, 65(5):753-763, 1991.
Hermonat and Muzycska, *Proc. Nat. Acad. Sci. USA*, 81:6466-6470, 1984.
Hersdorffer et al., *DNA Cell Biol*, 9:713-723, 1990.
Herz and Gerard, *Proc. Nat'l Acad. Sci. USA*, 90:2812-2816, 1993.
Hess et al., *J. Adv. Enzyme Reg*, 7:149, 1968.
Hitzeman et al., *J. Biol. Chem.*, 255:2073, 1980.
Holland et al., *Biochemistry*, 17:4900, 1978.
Holland, G. and Zlotnik, A., *Clin. Invest.*, 11: 751-758, 1993.
Holmes et al., *Prostate*, 27:25-29, 1996.
Horoszewicz, Kawinski and Murphy, *Anticancer Res.*, 7:927-936, 1987.
Horwich, et al., *J. Virol.*, 64:642-650, 1990.
Hosmer and Lemeshow, In: *Applied Logistic Regression*, New York, John Wiley and Sons, 1989.
Huang et al., *Prostate*, 23: 201-212, 1993.
Ikei et al., *Cytokine* 4: 581-584, 1992.
Innis et al., *PCR Protocols*, Academic Press, Inc., San Diego Calif., 1990.
Inouye et al., *Nucleic Acids Res.*, 13:3101-3109, 1985.
Isaacs et al., *Cancer Res.*, 51:4716-4720, 1991.
Isaacs et al., *Seminars in Oncology*, 21:1-18, 1994.
Israeli et al., *Cancer Research*, 54:1807-1811, 1994.
Israeli et al., *J. Urol.*, 153:573-577, 1995.
Jaakkola et al., *Clin. Chem.*, 41:182-186, 1995.
Jacobson et al., *JAMA*, 274:1445-1449, 1995.
Johnson et al., In: *BIOTECHNOLOGY AND PHARMACY*, Pezzuto et al., Eds., Chapman and Hall, New York, 1993.
Jones, *Genetics*, 85:12, 1977.
Jones and Shenk, *Cell*, 13:181-188, 1978.
Kaneda et al., *Science*, 243:375-378, 1989.
Karlsson et al., *EMBO J.*, 5:2377-2385, 1986.
Kato et al., *J. Biol. Chem.*, 266:3361-3364, 1991.
Katz, et al., *Urology*, 43:765-775, 1994.
Kingsman et al., *Gene*, 7: 141, 1979.
Klein et al., *Nature*, 327:70-73, 1987.
Koch et al., *Science*, 258:1798-1801, 1992.
Kohler and Milstein, *Eur. J. Immunol.*, 6: 511-519, 1976.
Kohler and Milstein, *Nature*, 256:495-497, 1975.
Kwoh et al., *Proc. Nat. Acad. Sci. USA*, 86: 1173, 1989.
Larsen, et al., *Science*, 243:1464-1466, 1989.
Le Gal La Salle et al., *Science*, 259:988-990, 1993.
Levrero et al., *Gene*, 101: 195-202, 1991.
Liang and Pardee, *Science*, 257:967-971. 1992.
Liang and Pardee, *Science*, 257: 967-971, 1992.
Liang et al., *Cancer Res.*, 52:6966-6968, 1992.
Liang and Pardee, U.S. Pat. No. 5,262,311
Lifton, *Science*, 272: 676, 1996.
Lilja et al., *Clin. Chem.*, 37:1618-1625, 1991.
Litirup et al., *Cancer*, 74:3146-3150, 1994.
Lopez-Nieto and Nigam, *Nature Biotechnology*, 14:857-861, 1996.
Lowy et al., *Cell*, 22:817, 1980.
Macoska et al., *Cancer Res.*, 54:3824-3830, 1994.
Mann et al., *Cell*, 33:153-159, 1983.
Markowitz et al., *J. Virol.*, 62:1120-1124, 1988.
Marley et al., *Urology*, 48(6A): 16-22, 1996.
McClelland et al., *Nucleic Acids Res.*, 22:4419-4431, 1994.
McCormack et al., *Urology*, 45:729-744, 1995.
Miki, et al., *Science*, 266: 66-71, 1994.
Miller et al., PCT Application WO 89/06700.
Mok et al., *Gynecol. Oncol.*, 52: 247-252, 1994.
Montie, *Urology*, 44: 2-8, 1994.
Morahan et al., *Science* 272: 1811, 1996.
Moreno et al., *Cancer Res.* 52:6110-6112, 1992.
Moreno et al., *Urology*, 49:515-520, 1997.
Morise et al., *Med. Dec. Making*, 16(2):133-142, 1996.
Morton et al., *Cancer Res.*, 53:3585-3590, 1993.
Morton et al., In: *CANCER MEDICINE* (3rd Ed.), Holland, J. F., Frei III, E., Bast Jr., C. C. (eds), Lea and Febiger, Philadelphia, Pa., pp. 1793-1824, 1993.
Mulligan et al., *Proc. Nat'l Acad. Sci. USA*, 78:2072, 1981.
Mulligan, *Science*, 260:926-932, 1993.
Murphy et al., *Cancer*, 78: 809-818, 1996.
Murphy et al., *Prostate*, 26:164-168, 1995.
Myers, EP 0273085
Nagase et al., *DNA Res.*, 3(5):321-329, 1996.
Nakamura et al., In: *Handbook of Experimental Immunology* (4th Ed.), Weir, E., Herzenberg, L. A., Blackwell, C., Herzenberg, L. (eds), Vol. 1, Chapter 27, Blackwell Scientific Publ., Oxford, 1987.
Nakano et al., *J. Biol. Chem.*, 271:14661-14664, 1996.
Nicolas and Rubenstein, In: *Vectors: A survey of molecular cloning vectors and their uses*, Rodriguez and Denhardt (eds.), Stoneham: Butterworth, pp. 493-513, 1988.
Nicolau and Sene, *Biochim. Biophys. Acta*, 721:185-190, 1982.
Nicolau et al., *Methods Enzymol.*, 149:157-176, 1987.
O'Hare et al., *Proc. Nat'l Acad. Sci. USA*, 78:1527, 1981.
Oesterling, *Contemporary Urology*, 8:76-92, 1996.
Oesterling et al., *J. Urol.*, 154:1090-1095, 1995.
Ohara et al., *Proc. Nat'l Acad. Sci. USA*, 86:5673-5677, 1989.
Papsidero et al., *Cancer Research*, 40:2428-2432, 1980.
Parker et al., *CA Cancer J. Clin.*, 65:5-27, 1996.
Partin and Oesterling, *Urology*, 48 (6A): 1-3, 1996.
Partin and Oesterling, *J. Urol.*, 152:1358-1368, 1994.
Partin and Oesterling, (Eds.) *Urology*, 48(6A) supplement: 1-87, 1996.
Partin et al., *Cancer Res.*, 53:744-746, 1993.
Paskind et al., *Virology*, 67:242-248, 1975.
Patarca et al., *Proc. Natl. Acad. Sci. USA*, 85:2733-2737, 1988.
Pearsons et al., *J. Urol.*, 150:120-125, 1993.
Perales et al., *Proc. Natl. Acad. Sci.* 91:4086-4090, 1994.
Pettersson et al., *Clin. Chem.*, 41(10):1480-1488, 1995.
Piironen et al., *Clin. Chem.* 42: 1034-1041, 1996.
Potter et al., *Proc. Nat. Acad. Sci. USA*, 81:7161-7165, 1984.
Price et al., *EMBO J.*, 12:2411-2418, 1993.
Qiao et al., *Biochem. Biophys. Res. Comm.*, 201:581-588, 1994.
Racher et al., *Biotechnology Techniques*, 9:169-174, 1995.
Ragot et al., *Nature*, 361:647-650, 1993.
Ralph and Veltri, *Advance/Laboratory*, 6:51-56, 1997.
Ralph et al., *Proc. Natl. Acad. Sci. USA*, 90:10710-10714, 1993.
Renan, *Radiother. Oncol.*, 19:197-218, 1990.
Ribas de Pouplana and Fothergill-Gilmore, *Biochemistry*, 33:7047-7055, 1994.
Rich et al., *Hum. Gene Ther.*, 4:461-476, 1993.
Ridgeway, In: *Vectors: A survey of molecular cloning vectors and their uses*, Rodriguez R L, Denhardt D T, ed., Stoneham: Butterworth, pp. 467-492, 1988.
Rieber, M. and Rieber, M. S., *Cell Growth Diff.*, 5:1339-1346, 1994.
Rippe et al., *Mol. Cell Biol.*, 10:689-695, 1990.
Rosenfeld et al., *Cell*, 68:143-155, 1992.
Rosenfeld et al., *Science*, 252:431-434, 1991.
Roux et al., *Proc. Nat'l Acad. Sci. USA*, 86:9079-9083, 1989.
Sager et al., *FASEB J*, 7:964-970, 1993.
Saito et al., *Biochem. Biophys. Res. Commun.*, 200:378, 1994.
Sambrook et al., (ed.), *MOLECULAR CLONING*, Cold Spring Harbor Laboratory Press, Cold Spring Harbor, N.Y., 1989.
Schadendorf et al., *J. Immunol.*, 151:2667-2675, 1993.
Scheibenbogen et al., *Melanoma Research*, 5:179-181, 1995.
Scott et al., *Molec. Cell. Biol.*, 13:2247-2257, 1993.
Seiden et al., *J. Clin. Oncol.*, 12:2634-2639, 1994.
Sidransky et al., *Science*, 252: 706-709, 1991.
Silver et al., *Clin. Cancer Res.*, 3: 81-85, 1997.
Slamon et al., *Science*, 224:256-262, 1984.
Slamon et al., *Science*, 244: 707-712, 1989.
Smith, U.S. Pat. No. 4,215,051
Soh et al., *J. Urol.*, 157:2212-2218, 1997.
Stamey, *Urology*, 45(2):173-184, 1995.
Steinberg and Colla, *CART: A supplementary module for SYSTAT*, Evanston, Ill., SYSTAT Inc., 1992.
Stenman et al., *Cancer Research*, 51:222-226, 1991.
Stinchcomb et al., *Nature*, 282:39, 1979.
Stone et al., *Urology*, 44: 18-25, 1994.
Stratford-Perricaudet and Perricaudet, In: *Human Gene Transfer*, O. Cohen-Haguenauer et al., eds., John Libbey Eurotext, France, pp. 51-61, 1991.
Stratford-Perricaudet et al., *Hum. Gene. Ther.*, 1:241-256, 1990.
Sulston et al., *Nature*, 356:37-41, 1992.
Sun and Cohen, *Gene*, 137:127-132, 1993.
Szybalska et al., *Proc. Nat'l Acad. Sci. USA*, 48: 2026, 1962.
Takahashi et al., *Cancer Res.*, 54:3574-3579, 1994.
Takahashi et al., *Mol. Cell. Biol.*, 8:1853-1856, 1988.
Takeuchi et al., *J. Biol. Chem.*, 271:19935-19942, 1996.
Tan et al., *J. Cell Biol.*, 128:307-319, 1995.
Taparowsky et al., *Nature*, 300: 762-764, 1982.
Tassan et al., *EMBO J.*, 14:4508-5617, 1995.
Temin, In: *Gene Transfer*, Kucherlapati (ed.), New York: Plenum Press, pp. 149-188, 1986.
Thanos and Maniatis, *Cell*, 80:529-532," 1995.
Tranque et al., *Proc. Natl. Acad. Sci. USA*, 93:3105-3109, 1996.
Tschemper et al., *Gene*, 10:157, 1980.
Tummuru et al., *Molec. Microbiol.* 18: 8670876, 1995.
Tur-Kaspa et al., *Mol. Cell Biol.*, 6:716-718, 1986.
Umbas et al., *Cancer Res.*, 52:5104-5109, 1992.
VanArsdale et al., *Proc. Natl. Acad. Sci. USA*, 94:2460-2465, 1997.
Varmus et al., *Cell*, 25:23-36, 1981.
Vieira et al., *Proc. Natl. Acad. Sci. U.S.A.* 88(4): 1172-1176, 1991.
Vinante et al., *Leukemia*, 7:1552-1556, 1993.
Visakorpi et al., *Am. J. Pathol.*, 145:1-7, 1994.
Vishwanatha et al., *Carcinogenesis*, 14:2575-2579, 1993.
Vollmer, *Am. J. Clin. Pathol.*, 105:115-126, 1996.
Wagner et al., *Science*, 260:1510-1513, 1990.
Walker et al., *Proc. Nat'l Acad. Sci. USA*, 89:392-396, 1992.
Walsh and Worthington, *The Prostate*, Chap. 3, Johns Hopkins-University Press, 1995.
Wan et al., *Nature Biotechnology*, 14:1685-1691, 1996.
Watson et al., *Cancer Res.*, 54:4598-4602, 1994.
Webb and Lin, *Invest. Urol.*, 17:401-404, 1980.
Welsh and McClelland, *Nucl. Acids Res.*, 18:7213-7218, 1990.
Welsh et al., *Nucl. Acids Res.*, 20: 4965-70, 1992.
Whittemore, *Biometrika*, 82(1):57-67, 1995.
Wigler et al., *Cell*, 11: 223, 1977.
Wigler et al., *Proc. Nat'l Acad. Sci. USA*, 77:3567, 1980.
Wingo et al., *CA Cancer J. Clin.*, 47: 239-242, 1997.
Wong et al., *Gene*, 10:87-94, 1980.
Wong et al., *Int. J. Oncol.*, 3:13-17, 1993.
Wu and Wu, *J. Biol. Chem.*, 262: 4429-4432, 1987.
Wu and Wu, *Biochemistry*, 27: 887-892, 1988.
Wu and Wu, *Adv. Drug Delivery Rev.*, 12:159-167, 1993.
Wu et al., *Genomics*, 4:560, 1989.
Yang et al., *Proc. Natl. Acad. Sci. USA*, 87:9568-9572, 1990.
Yoon et al., *Science*, 269:1102-1105, 1995.
Zhang et al., *Clin. Chem.*, 41(11): 1567-73, 1995.
Zlotta, et al., *J. Urol.*, 157:1315-1321, 1997.

What is claimed is:

1. A method of detecting metastatic cancer, comprising the steps of:
   (a) detecting the quantity of a disease marker mRNA expressed in human peripheral blood; and
   (b) comparing the quantity of said marker to the quantity expressed in peripheral blood of a normal individual; wherein said mRNA comprises SEQ ID NO:49 and wherein a difference in quantity of expression is indicative of metastatic cancer.

2. The method of claim 1, further comprising the steps of
   a) providing primers that selectively amplify the metastatic cancer marker;
   b) amplifying said nucleic acid with said primers to form nucleic acid amplification products;
   c) detecting said nucleic acid amplification products; and
   d) measuring the amount of said nucleic acid amplification products formed.

3. The method of claim 1, wherein said mRNA is amplified by an RNA polymerase reaction.

4. The method of claim 1, wherein said mRNA is amplified by reverse transcriptase polymerase chain reaction or the ligase chain reaction.

5. The method of claim 1, wherein said detecting is by RNA fingerprinting, branched DNA or a nuclease protection assay.

6. The method of claim 1, wherein the metastatic cancer is metastatic prostate cancer.

7. The method of claim 1, wherein the metastatic cancer is metastatic breast cancer.

* * * * *

UNITED STATES PATENT AND TRADEMARK OFFICE
CERTIFICATE OF CORRECTION

PATENT NO. : 7,332,270 B1
APPLICATION NO. : 09/660568
DATED : February 19, 2008
INVENTOR(S) : David Ralph et al.

It is certified that error appears in the above-identified patent and that said Letters Patent is hereby corrected as shown below:

In title page, item (30) Foreign Application Priority Data, please insert
--Dec. 5, 1997 (WO) PCT/US97/22105--.

Signed and Sealed this

Twenty-seventh Day of May, 2008

JON W. DUDAS
*Director of the United States Patent and Trademark Office*

SEQUENCE LISTING

<160> NUMBER OF SEQ ID NOS: 55

<210> SEQ ID NO 1
<211> LENGTH: 387
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
ggtgagcccc aggagacaga agagatatga ggaaattgtt aaggaagtca gcacttacat      60
taagaaaatt ggctacaacc ccgacacagt agcatttgtg ccaatttctg gttggaatgg     120
tgacaacatg ctggagccaa gtgctaacat gccttggttc aagggatgga aagtcacccg     180
taaggatggc aatgccagtg gaaccacgct gcttgaggct ctggactgca tcctaccacc     240
aactcgtcca actgacaagc ccttgcgcct gcctctccaa ggatgttctt acaaaattgg     300
tggtattggt actgttccct gtttggccga attggaaaac tggtgttcct ccaaaccccg     360
gttatggtgg gtttcctcct ccttgga                                        387

<210> SEQ ID NO 2
<211> LENGTH: 365
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
gggcggaaca agggagcgct aaaaggaaat taggatgtca ggtgcataaa ggacataatt      60
ccaaaacctt tccaaacccc aaatttattc aaaggaactg aggagtggat tgaggagtgg     120
accaacactg gcgccaaaca cagaaattat tgtaaagctt tctgatggaa gagagctctg     180
tctgggcccc aaggaaaact gggtgcagag ggttgtggag aagttttttga agagggctga    240 gaattcataa aaaaattcat tctctgtggt atccaagaat cagtgaagat gccagtgaaa     300
cttcaagcaa atctacttca acacttcatg tattgtgtgg gtctgttgta gggttgccag     360
ttgtt                                                                365

<210> SEQ ID NO 3
<211> LENGTH: 598
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
gcttgggccc caaggaaaac tgggtgcaga gggttgtgga aagttttttg aagaggtaag      60
ttatatattt ttgaatttaa aatttgtcat ttatccgtga gacatataat ccaaagtcag     120
cctataaatt tctttctgtt gctaaaaatc gtcattaggt atctgccttt ttggttaaaa     180
aaaaaaggaa tagcatcaat agtgagtgtg ttgtactcat gaccagaaag accatacata     240
gtttgcccag gaattctggg tttaagcttg tgtcctata ctcttagtaa agttctttgt      300
cactcccagt agtgtcctat gttagatgat aatgtctttg atctccctat ttatagttga     360
gaatatagag catgtctaac acatgaatgt caaagactat attgacttttt caagaaccct    420

```
actttccttc ttattaaaca tagctcatct ttatattgtg aattttattt tagggctgag      480
aattcataaa aaaattcatt ctctgtggta tccaagaatc agtgaagatg ccagtgaaac      540
ttcaagcaaa tctacttcaa cacttcatgt attgtgtggg tctgttgtag ggttgcca       598
```

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
cgcctcaggc tggggcagca tt                                               22

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
acagtggaag agtctcattc gagat                                            25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
cgagctgcct gacggccagg tcatc                                            25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
gaagcatttg cggtggacga tggag                                            25

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
gacaacatgc tggagccaag tgc                                              23

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

```
<400> SEQUENCE: 9
accaccaatt ttgtaagaac atcct                                              25

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
gggccccaag gaaaact                                                       17

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
tggcaaccct acaacagacc                                                    20

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
gggccccaag gaaaact                                                       17

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
acgactcact ataagcagga                                                    20

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
tgacccagcc ccttgagaaa cct                                                23

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 15
gcctcaggct ggggcagcat t                                            21

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
ggtcaccttc tgagggtgaa cttgc                                        25

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
aacaactggc aa                                                      12

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
ggcgacaagg ag                                                      12

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
ggagctgcct gacggccagg tcatc                                        25

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
ttgccaagga gtgctaaaga ac                                           22

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
```

-continued tggaccccaa ggaaaact                                          18

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
gggcccaagg aaaact                                            16

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
aacagctatg accatcgtgg                                        20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
acgactcact atgtggagaa                                        20

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
ctggcctacg aagatacga cac                                     23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
acaatccgga ggcatcagaa act                                    23

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27

-continued agccccggcc tcctcgtcct c                                           21

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
ggcggcggca gcggttctc                                              19

<210> SEQ ID NO 29
<211> LENGTH: 1614
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
gcggcaggcg cggcaaatta cgttgccgga gctgaacggc gcggctggtc tgaaggcaaa    60
caagcgagcg agcgcgcgat aggggccgag aggacgcgca ggtggcggcg ttgccatgtc   120
gcacggtcac agccacggcg ggggtggctg ccgctgcgcc gccgaacggg aggagccgcc   180
cgagcagcgc ggcctggcct acggcctgta cctgcgcatc gacctggagc ggctgcaatg   240
ccttaacgag agccgcgagg gcagcggccg cggcgtcttc aagccatggg aggagcggac   300
cgaccgctcc aagtttattg aaagtgatgc agatgaagag cttctgttta atattccatt   360
tacgggcaat gtcaagctca aaggcatcat tataatggga gaggatgatg actcacaccc   420
ctctgagatg agactgtaca agaatattcc acagatgtcc tttgatgata cagaaaggga   480
gccagatcag acctttagtc tgaaccggga tcttacagga gaattagagt atgctacaaa   540
aatttctcgt ttttcaaatg tctatcatct ctcaattcat atttcaaaaa acttcggagc   600
agatacgaca aaggtctttt atattggcct gagaggagag tggactgagc ttcgccgaca   660
cgaggtgacc atctgcaatt acgaagcatc tgccaaccca gcagaccata gggtccatca   720
ggttacccca cagacacact ttatttccta agggctggcc aaggctccca tagaggcgct   780
gtgtcagtga agatgtacga ctacctgttg gaaggacaa agggatgagg ctccagagag   840
agttggctgc cacagctctg ccaagctttg tctttggggc ttgctgcaga aacctggcct   900
acggaagata cgacaccact gggagggttg tgtaggtgcc aggggaccat cgtggttctc   960
tagggcgctg tggaaattgg gtcttgggct gggtggcatc tggcagtcat gggtaacact  1020
tgcttttcca gttaatgtgg ccatgtgatt ccaagtgtca tgttgctttg tggaagattg  1080
ttgtgtgact tgttttttg attttgtatt tgttttttta aaggaaacta tttgtgggct  1140
ataggaaact ttctgatgcc tccggattgt gttagtagta gccatcagga gggtctccaa  1200
ctaaaacact tgttcctgct tgctcctttc ccctctcatt gttcagcatt cttgtcaagt  1260
tgcccagctt ggagttgtct gtcacgcaca tgtgtcctgt ggttatagct agaaggacag  1320
gagtctcctg ctgatgcgtg atagcttaag cttggggaga aggtctttc cactgcctag   1380 ctaagcagtc tggggagagc atggggatca tttctatgtg tgtgggtaat ctggtcagta  1440
agattgagac ttagttaaga ttcccttgg aaattcctta atgtttatta gcttctaact  1500
agtgttgtaa gtccgatgcc agaatttgga gatttgagtt cttcttttca tggcttttat  1560
tcactgtgac taataagctt cctaataaat ccttgccaga cttaaaaaaa aaaa         1614

<210> SEQ ID NO 30
<211> LENGTH: 1268
<212> TYPE: DNA
<213> ORGANISM: Artificial Sequence
<220> FEATURE:
<223> OTHER INFORMATION: Description of Artificial Sequence: Synthetic Primer

<400> SEQUENCE: 30

```
tttcaagccg tgggaggacg gaccgaccgc tccaagttcg ctgaaagtga tgcggacgaa      60
gagctcctgt ttaatattcc gtttacgtgc aatgtcaagc tgaaaggcgt catcataatg     120
ggcgaggatg atgactcgca cccctcggag atgagactgt acaagaacat tccacagatg     180
tcatttgatg acacagaaag ggagccagag cagaccttca gtctgaaccg agacattaca     240
ggagaattag aatatgctac gaaaatctcc aggttttcaa atgtctatca tctttccatt     300
catatttcaa aaactttggg agcagatacg acgaagatct tttatattgg cctgcgggga     360
gagtggactg agcttcgccg gcatgaggtg accatctgca actatgaagc gtcagccaac     420
ccagcagacc accgggtgca tcaggtcacc ccgcagacac acttcatttc ttaagggcca     480
gccgggctc cctcagatgc gctgttagtg aagatgtgcg accacctgct gggaaggaca     540
gaggatgctc cagcaatagt tgcctgccag agctttggcc aggctttgtc tcggggttgc     600
tgcaggaacc tggcctgtgg aaaccgcctc accaccagga gcggtatggg tgccaaggga     660
tagtctctct ctaaggcact gcagaaactg ggtcttaggc tgggtggcat ctgtcagtca     720
tgaataatgc tcacttccca gtctgtggcc acgggatccc atgtgtcttt ttgcttgatt     780
tcttgtgtgg tttgtccttt tgtggcatca aaaggatgc ttccttgacc gtagaatcct     840
tctgaaaccc gagtttcgtg tttgaattag ccatcaggag ggtctccagc tagaaacact     900
tcgtccctgc ttgctcctcc tcctgtcatt gctcagcatt cgtgtcaggg tgcctagctg     960
gtgtcacata tcagacacaa gtgtcccaca atggtggttg gaaaggaagg agtctcctga    1020
tacatgactg cttggggaag gcttacacag tctagccaaa ttagttgcga gtcctttccc    1080
tgtgtgggtg acctggttgg ggtaaaactg agacagtaaa gattcctctt gggacctcct    1140
tggtgtttcc ctgcttctaa ctcatgttat aaacccaggg ctggagtctg gagaccctgc    1200
tccttctgtt catggctttc attcatggtg actaatgagc ttcctaataa atccttagag    1260
acttaaaa                                                             1268
```

<210> SEQ ID NO 31
<211> LENGTH: 211
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 31

```
Met Ser His Gly His Ser His Gly Gly Gly Cys Arg Cys Ala Ala
  1               5                  10                  15

Glu Arg Glu Glu Pro Pro Glu Gln Arg Gly Leu Ala Tyr Gly Leu Tyr
                 20                  25                  30

Leu Arg Ile Asp Leu Glu Arg Leu Gln Cys Leu Asn Glu Ser Arg Glu
             35                  40                  45

Gly Ser Gly Arg Gly Val Phe Lys Pro Trp Glu Glu Arg Thr Asp Arg
         50                  55                  60
```

```
Ser Lys Phe Ile Glu Ser Asp Ala Asp Glu Glu Leu Leu Phe Asn Ile
 65                  70                  75                  80

Pro Phe Thr Gly Asn Val Lys Leu Lys Gly Ile Ile Met Gly Glu
                 85                  90                  95

Asp Asp Asp Ser His Pro Ser Glu Met Arg Leu Tyr Lys Asn Ile Pro
            100                 105                 110

Gln Met Ser Phe Asp Asp Thr Glu Arg Glu Pro Asp Gln Thr Phe Ser
            115                 120                 125

Leu Asn Arg Asp Leu Thr Gly Glu Leu Glu Tyr Ala Thr Lys Ile Ser
130                 135                 140

Arg Phe Ser Asn Val Tyr His Leu Ser Ile His Ile Ser Lys Asn Phe
145                 150                 155                 160

Gly Ala Asp Thr Thr Lys Val Phe Tyr Ile Gly Leu Arg Gly Glu Trp
                165                 170                 175

Thr Glu Leu Arg Arg His Glu Val Thr Ile Cys Asn Tyr Glu Ala Ser
            180                 185                 190

Ala Asn Pro Ala Asp His Arg Val His Gln Val Thr Pro Gln Thr His
            195                 200                 205

Phe Ile Ser
    210

<210> SEQ ID NO 32
<211> LENGTH: 157
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 32

Phe Lys Pro Trp Glu Glu Arg Thr Asp Arg Ser Lys Phe Ala Glu Ser
 1               5                  10                  15

Asp Ala Asp Glu Glu Leu Leu Phe Asn Ile Pro Phe Thr Cys Asn Val
             20                  25                  30

Lys Leu Lys Gly Val Ile Ile Met Gly Glu Asp Asp Asp Ser His Pro
         35                  40                  45

Ser Glu Met Arg Leu Tyr Lys Asn Ile Pro Gln Met Ser Phe Asp Asp
     50                  55                  60

Thr Glu Arg Glu Pro Glu Gln Thr Phe Ser Leu Asn Arg Asp Ile Thr
 65                  70                  75                  80

Gly Glu Leu Glu Tyr Ala Thr Lys Ile Ser Arg Phe Ser Asn Val Tyr
                 85                  90                  95

His Leu Ser Ile His Ile Ser Lys Asn Phe Gly Ala Asp Thr Thr Lys
            100                 105                 110

Ile Phe Tyr Ile Gly Leu Arg Gly Glu Trp Thr Glu Leu Arg Arg His
            115                 120                 125

Glu Val Thr Ile Cys Asn Tyr Glu Ala Ser Ala Asn Pro Ala Asp His
            130                 135                 140

Arg Val His Gln Val Thr Pro Gln Thr His Phe Ile Ser
145                 150                 155

<210> SEQ ID NO 33
<211> LENGTH: 207
<212> TYPE: PRT
<213> ORGANISM: Artificial Sequence
<220> FEATURE:
<223> OTHER INFORMATION: Description of Artificial Sequence:  Synthetic
      Peptide
```

<400> SEQUENCE: 33

```
Cys Ser His Gly His Ser His Asn Cys Ala Ala Glu His Ile Pro Glu
1               5                   10                  15
Val Pro Gly Asp Asp Val Tyr Arg Tyr Asp Met Val Ser Tyr Ile Asp
            20                  25                  30
Met Glu Lys Val Thr Thr Leu Asn Glu Ser Val Asp Gly Ala Gly Lys
        35                  40                  45
Lys Val Phe Lys Val Met Glu Lys Arg Asp Asp Arg Leu Glu Tyr Val
    50                  55                  60
Glu Ser Asp Cys Asp His Glu Leu Leu Phe Asn Ile Pro Phe Thr Gly
65                  70                  75                  80
His Val Arg Leu Thr Gly Leu Ser Ile Ile Gly Asp Glu Asp Gly Ser
                85                  90                  95
His Pro Ala Lys Ile Arg Leu Phe Lys Asp Arg Glu Ala Met Ser Phe
            100                 105                 110
Asp Asp Cys Ser Ile Glu Ala Asp Gln Glu Ile Asp Leu Lys Gln Asp
        115                 120                 125
Pro Gln Gly Leu Val Asp Tyr Pro Leu Lys Ala Ser Lys Phe Gly Asn
    130                 135                 140
Ile His Asn Leu Ser Ile Leu Val Asp Ala Asn Phe Gly Glu Asp Glu
145                 150                 155                 160
Thr Lys Ile Tyr Tyr Ile Gly Leu Arg Gly Glu Phe Gln His Glu Phe
                165                 170                 175
Arg Gln Arg Ile Ala Ile Ala Thr Tyr Glu Ser Arg Ala Gln Leu Lys
            180                 185                 190
Asp His Lys Asn Glu Ile Pro Asp Ala Val Ala Lys Gly Leu Phe
        195                 200                 205
```

<210> SEQ ID NO 34
<211> LENGTH: 3205
<212> TYPE: DNA
<213> ORGANISM: Artificial Sequence
<220> FEATURE:
<223> OTHER INFORMATION: Description of Artificial Sequence: Synthetic Primer

<400> SEQUENCE: 34

```
cgactcgtcg ccattcccgg agcaggtcgg cctcggccca ggggcgagta tccgttgctg      60
tgtcggagac actagtcccc gacaccgaga cagccagccc tctcccctgc ctcgcggcgg     120
gagagcgtgt ccggccggcc ggccggcggg gctcgcgcaa cctccctcgc ctccccttcc     180
cccgcagcct ccgccccgcc aggcccggcc cggactcccg agccccggcc tcctcgtcct     240
cggtcgccgc tgccgccggg cttaacagcc ccgtccgccg cttctcttcc tagtttgaga     300
agccaaggaa ggaaacaggg aaaaatgtcg ccatgaaggc cgagaaccgc tgccgccgcc     360
gaccccgcc ggccctgaac gccatgagcc tgggtccccg ccgcgcccgc tccgctccga     420
ctgccgtcgc cgccgaggcc cccgttgatg ccgctgagct cccccaacgc gccgccacc     480
gcctccgaca tggacaagaa cagcggctcc aacagctcct ccgcctcttc gggcagcagc     540
aaagggcaac agccgccccg ctccgcctcg gcggggccag ccggcgagtc taaacccaag     600
agcgaattac taatttcagc tggattcaat ttgttgtcag ttgattctgt agtaaggcca     660
tatgttgccc ctctggaggt gcttgtcaac tactctggat gatggatgga aagaactcca     720
gtggatccaa gcgttataat cgcaaacgtg aactttccta ccccaaaaat gaaagtttta     780
```

```
acaaccagtc ccgtcgctcc agttcacaga aaagcaagac ttttaacaag atgcctcctc    840
aaaggggcgg cggcagcagc aaactctttta gctcttcttt taatggtgga agacgagatg    900
aggtagcaga ggctcaacgg gcagagttta gccctgccca gttctctggt cctaagaaga    960
tcaacctgaa ccacttgttg aatttcactt ttgaaccccg tggccagacg ggtcactttg   1020
aaggcagtgg acatggtagc tggggaaaga ggaacaagtg gggacataag ccttttaaca   1080
aggaactctt tttacaggcc aactgccaat ttgtggtgtc tgaagaccaa gactacacag   1140
ctcattttgc tgatcctgat acattagtta actgggactt tgtggaacaa gtgcgcattt   1200
gtagccatga agtgccatct tgcccaatat gcctctatcc acctactgca gccaagataa   1260
cccgttgtgg acacatcttc tgctgggcat gcatcctgca ctatctttca ctgagtgaga   1320
agacgtggag taaatgtccc atctgttaca gttctgtgca taagaaggat ctcaagagtg   1380
ttgttgccac agagtcacat cagtatgttg ttggtgatac cattacgatg cagctgatga   1440
agagggagaa aggggtgttg gtggcttttgc ccaaatccaa atggatgaat gtagaccatc   1500
ccattcatct aggagatgaa cagcacagcc agtactccaa gttgctgctg gcctctaagg   1560
agcaggtgct gcaccgggta gttctggagg agaaagtagc actagagcag cagctggcag   1620
aggagaagca cactcccgag tcctgcttta ttgaggcagc tatccaggag ctcaagactc   1680
gggaagaggc tctgtcggga ttggccggaa gcagaaggga ggtcactggt gttgtggctg   1740
ctctggaaca actggtgctg atggctccct ggcgaagga gtctgttttt caacccagga   1800
agggtgtgct ggagtatctg tctgccttcg atgaagaaac cacggaagtt tgttctctgg   1860
acactccttc tagacctctt gctctccctc tggtagaaga ggaggaagca gtgtctgaac   1920
cagagcctga ggggttgcca gaggcctgtg atgacttgga gttagcagat gacaatctta   1980 aagagggac catttgcact gagtccagcc agcaggaacc catcaccaag tcaggcttca   2040
cacgcctcag cagctctcct tgttactact tttaccaagc ggaagatgga cagcatatgt   2100
tcctgcaccc tgtgaatgtg cgctgcctcg tgcgggagta cggcagcctg gagaggagcc   2160
ccgagaagat ctcagcaact gtggtggaga ttgctggcta ctccatgtct gaggatgttc   2220
gacagcgtca cagatatctc tctcacttgc cactcacctg tgagttcagc atctgtgaac   2280
tggctttgca acctcctgtg gtctctaagg aaaccctaga gatgttctca gatgacattg   2340
agaagaggaa acgtcagcgc caaaagaagg ctcgggagga acgccgccga gagcgcagga   2400
ttgagataga ggagaacaag aaacagggca agtacccaga agtccacatt cccctcgaga   2460
atctacagca gtttcctgcc ttcaattctt ataccgctc ctctgattct gctttgggtc   2520
ccaccagcac cgagggccat ggggccctct ccatttctcc tctcagcaga agtccaggtt   2580
cccatgcaga ctttctgctg accccctctgt cacccactgc cagtcagggc agtccctcat   2640
tctgcgttgg gagtctggaa gaagactctc ccttcccttc cttttgccccag atgctgaggg   2700 ttggaaaagc aaaagcagat gtgtggccca aaactgctcc aaagaaagat gagaacagct   2760
tagttcctcc tgcccctgtg gacagcgacg gggagagtga taattcagac cgtgttcctg   2820
tgcccagttt tcaaaattcc ttcagccaag ctattgaagc agccttcatg aaactggaca   2880
caccagctac ttcagatccc ctctctgaag agaaggagg aagaaaaga aaaaaacaga   2940 aacagaagct cctgttcagc acctcagtcg tccacaccaa gtgacactac tggcccaggc   3000
taccttctcc atctggtttt tgtttttgtt ttttttttccc ccatgctttt gtttggctgc   3060 tgtaatttttt aagtatttga gtttgaacag attagctctg gggggagggg gtttccacaa   3120
tgtgaggggg aaccaagaaa attttaaata cagtgtattt tccagcttcc tgtctttaca   3180
```

-continued

```
ccaaaataaa gtattgacac aagag                                          3205
```

<210> SEQ ID NO 35
<211> LENGTH: 761
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 35

```
Met Met Asp Gly Lys Asn Ser Ser Gly Ser Lys Arg Tyr Asn Arg Lys
  1               5                  10                  15

Arg Glu Leu Ser Tyr Pro Lys Asn Glu Ser Phe Asn Asn Gln Ser Arg
                 20                  25                  30

Arg Ser Ser Ser Gln Lys Ser Lys Thr Phe Asn Lys Met Pro Pro Gln
             35                  40                  45

Arg Gly Gly Gly Ser Ser Lys Leu Phe Ser Ser Phe Asn Gly Gly
         50                  55                  60

Arg Arg Asp Glu Val Ala Glu Ala Gln Arg Ala Glu Phe Ser Pro Ala
 65                  70                  75                  80

Gln Phe Ser Gly Pro Lys Lys Ile Asn Leu Asn His Leu Leu Asn Phe
                 85                  90                  95

Thr Phe Glu Pro Arg Gly Gln Thr Gly His Phe Glu Gly Ser Gly His
                100                 105                 110

Gly Ser Trp Gly Lys Arg Asn Lys Trp Gly His Lys Pro Phe Asn Lys
            115                 120                 125

Glu Leu Phe Leu Gln Ala Asn Cys Gln Phe Val Val Ser Glu Asp Gln
130                 135                 140

Asp Tyr Thr Ala His Phe Ala Asp Pro Asp Thr Leu Val Asn Trp Asp
145                 150                 155                 160

Phe Val Glu Gln Val Arg Ile Cys Ser His Glu Val Pro Ser Cys Pro
                165                 170                 175

Ile Cys Leu Tyr Pro Pro Thr Ala Ala Lys Ile Thr Arg Cys Gly His
                180                 185                 190

Ile Phe Cys Trp Ala Cys Ile Leu His Tyr Leu Ser Leu Ser Glu Lys
            195                 200                 205

Thr Trp Ser Lys Cys Pro Ile Cys Tyr Ser Ser Val His Lys Lys Asp
210                 215                 220

Leu Lys Ser Val Val Ala Thr Glu Ser His Gln Tyr Val Val Gly Asp
225                 230                 235                 240

Thr Ile Thr Met Gln Leu Met Lys Arg Glu Lys Gly Val Leu Val Ala
                245                 250                 255

Leu Pro Lys Ser Lys Trp Met Asn Val Asp His Pro Ile His Leu Gly
                260                 265                 270

Asp Glu Gln His Ser Gln Tyr Ser Lys Leu Leu Ala Ser Lys Glu
            275                 280                 285

Gln Val Leu His Arg Val Val Leu Glu Glu Lys Val Ala Leu Glu Gln
        290                 295                 300

Gln Leu Ala Glu Glu Lys His Thr Pro Glu Ser Cys Phe Ile Glu Ala
305                 310                 315                 320

Ala Ile Gln Glu Leu Lys Thr Arg Glu Glu Ala Leu Ser Gly Leu Ala
                325                 330                 335

Gly Ser Arg Arg Glu Val Thr Gly Val Val Ala Ala Leu Glu Gln Leu
            340                 345                 350
```

-continued

```
Val Leu Met Ala Pro Leu Ala Lys Glu Ser Val Phe Gln Pro Arg Lys
            355                 360                 365
Gly Val Leu Glu Tyr Leu Ser Ala Phe Asp Glu Thr Thr Glu Val
        370                 375                 380
Cys Ser Leu Asp Thr Pro Ser Arg Pro Leu Ala Leu Pro Leu Val Glu
385                 390                 395                 400
Glu Glu Glu Ala Val Ser Glu Pro Glu Pro Gly Leu Pro Glu Ala
                405                 410                 415
Cys Asp Asp Leu Glu Leu Ala Asp Asp Asn Leu Lys Glu Gly Thr Ile
            420                 425                 430
Cys Thr Glu Ser Ser Gln Gln Glu Pro Ile Thr Lys Ser Gly Phe Thr
            435                 440                 445
Arg Leu Ser Ser Ser Pro Cys Tyr Tyr Phe Tyr Gln Ala Glu Asp Gly
        450                 455                 460
Gln His Met Phe Leu His Pro Val Asn Val Arg Cys Leu Val Arg Glu
465                 470                 475                 480
Tyr Gly Ser Leu Glu Arg Ser Pro Glu Lys Ile Ser Ala Thr Val Val
                485                 490                 495
Glu Ile Ala Gly Tyr Ser Met Ser Glu Asp Val Arg Gln Arg His Arg
            500                 505                 510
Tyr Leu Ser His Leu Pro Leu Thr Cys Glu Phe Ser Ile Cys Glu Leu
        515                 520                 525
Ala Leu Gln Pro Pro Val Val Ser Lys Glu Thr Leu Glu Met Phe Ser
        530                 535                 540
Asp Asp Ile Glu Lys Arg Lys Arg Gln Arg Gln Lys Lys Ala Arg Glu
545                 550                 555                 560
Glu Arg Arg Arg Glu Arg Ile Glu Ile Glu Glu Asn Lys Lys Gln
                565                 570                 575
Gly Lys Tyr Pro Glu Val His Ile Pro Leu Glu Asn Leu Gln Gln Phe
            580                 585                 590
Pro Ala Phe Asn Ser Tyr Thr Cys Ser Ser Asp Ser Ala Leu Gly Pro
        595                 600                 605
Thr Ser Thr Glu Gly His Gly Ala Leu Ser Ile Ser Pro Leu Ser Arg
        610                 615                 620
Ser Pro Gly Ser His Ala Asp Phe Leu Leu Thr Pro Leu Ser Pro Thr
625                 630                 635                 640
Ala Ser Gln Gly Ser Pro Ser Phe Cys Val Gly Ser Leu Glu Glu Asp
                645                 650                 655
Ser Pro Phe Pro Ser Phe Ala Gln Met Leu Arg Val Gly Lys Ala Lys
            660                 665                 670
Ala Asp Val Trp Pro Lys Thr Ala Pro Lys Asp Glu Asn Ser Leu
        675                 680                 685
Val Pro Pro Ala Pro Val Asp Ser Asp Gly Glu Ser Asp Asn Ser Asp
        690                 695                 700
Arg Val Pro Val Pro Ser Phe Gln Asn Ser Phe Ser Gln Ala Ile Glu
705                 710                 715                 720
Ala Ala Phe Met Lys Leu Asp Thr Pro Ala Thr Ser Asp Pro Leu Ser
                725                 730                 735
Glu Glu Lys Gly Gly Lys Lys Arg Lys Lys Gln Lys Gln Lys Leu Leu
            740                 745                 750
Phe Ser Thr Ser Val Val His Thr Lys
        755                 760
```

-continued

```
<210> SEQ ID NO 36
<211> LENGTH: 42
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 36

Cys Pro Ile Cys Leu Tyr Pro Pro Thr Ala Ala Lys Ile Thr Arg Cys
  1               5                  10                  15

Gly His Ile Phe Cys Trp Ala Cys Ile Leu His Tyr Leu Ser Leu Ser
             20                  25                  30

Glu Lys Thr Trp Ser Lys Cys Pro Ile Cys
         35                  40

<210> SEQ ID NO 37
<211> LENGTH: 41
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 37

Cys Pro Ile Cys Leu Glu Leu Ile Lys Glu Pro Val Ser Thr Lys Cys
  1               5                  10                  15

Asp His Ile Phe Cys Lys Phe Cys Met Leu Lys Leu Leu Asn Gln Lys
             20                  25                  30

Lys Gly Pro Ser Gln Cys Pro Leu Cys
         35                  40

<210> SEQ ID NO 38
<211> LENGTH: 44
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 38

Cys Pro Ile Cys Leu Glu Leu Leu Lys Glu Pro Val Ser Ala Asp Cys
  1               5                  10                  15

Asn His Ser Phe Cys Arg Ala Cys Ile Thr Leu Asn Tyr Glu Ser Asn
             20                  25                  30

Arg Asn Thr Asp Gly Lys Gly Asn Cys Pro Val Cys
         35                  40

<210> SEQ ID NO 39
<211> LENGTH: 40
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 39

Cys Ala Phe Cys His Ser Val Leu His Asn Pro His Gln Thr Gly Cys
  1               5                  10                  15

Gly His Arg Phe Cys Gln Gln Cys Ile Arg Ser Leu Arg Glu Leu Asn
             20                  25                  30

Ser Val Pro Ile Cys Pro Val Asp
         35                  40
```

<210> SEQ ID NO 40
<211> LENGTH: 45
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 40

Cys Pro Ile Cys Met Glu Ser Phe Thr Glu Glu Gln Leu Arg Pro Lys
 1               5                  10                  15

Leu Leu His Cys Gly His Thr Ile Cys Arg Gln Cys Leu Glu Lys Leu
            20                  25                  30

Leu Ala Ser Ser Ile Asn Gly Val Arg Cys Pro Phe Cys
        35                  40                  45

<210> SEQ ID NO 41
<211> LENGTH: 44
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 41

Cys Pro Arg Cys Lys Thr Thr Lys Tyr Arg Asn Pro Ser Leu Lys Leu
 1               5                  10                  15

Met Val Asn Val Cys Gly His Thr Leu Cys Glu Ser Cys Val Asp Leu
            20                  25                  30

Leu Phe Val Arg Gly Ala Gly Asn Cys Pro Glu Cys
        35                  40

<210> SEQ ID NO 42
<211> LENGTH: 41
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 42

Cys Pro Val Cys Leu Gln Tyr Phe Ala Glu Pro Met Met Leu Asp Cys
 1               5                  10                  15

Gly His Asn Ile Cys Cys Ala Cys Leu Ala Arg Cys Trp Gly Thr Ala
            20                  25                  30

Glu Thr Asn Val Ser Cys Pro Gln Cys
        35                  40

<210> SEQ ID NO 43
<211> LENGTH: 39
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 43

Cys Val Leu Cys Gly Gly Tyr Phe Ile Asp Ala Thr Thr Ile Ile Glu
 1               5                  10                  15

Cys Leu His Phe Ser Cys Lys Thr Cys Ile Val Arg Tyr Leu Glu Thr
            20                  25                  30

Ser Lys Tyr Cys Pro Ile Cys

<210> SEQ ID NO 44
<211> LENGTH: 40
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 44

Cys Ala Ile Cys Leu Asp Glu Tyr Glu Asp Gly Asp Lys Leu Arg Ile
 1               5                  10                  15

Leu Pro Cys Ser His Ala Tyr His Cys Lys Cys Val Asp Pro Trp Leu
             20                  25                  30

Thr Lys Lys Thr Cys Pro Val Cys
         35                  40

<210> SEQ ID NO 45
<211> LENGTH: 41
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 45

Cys Thr Ile Cys Tyr Glu Asn Pro Ile Asp Ser Val Leu Tyr Met Cys
 1               5                  10                  15

Gly His Met Cys Met Cys Tyr Asp Cys Ala Ile Glu Gln Trp Arg Gly
             20                  25                  30

Val Gly Gly Gly Gln Cys Pro Leu Cys
         35                  40

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 46
aacagctatg accctgagga                                              20

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 47
aagccccaag cccagagaca agat                                         24

<210> SEQ ID NO 48
<211> LENGTH: 253
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 48

```
ggcaggggct tgtgactcta agatggcttc attcacatgc ctagggcctc agtaggatga    60
ctggcatggc cctggaaaac tgcgaagtct tctctctgtg caaactttca cctggacttt   120
ttatatgatt ctggaagtat tccaagaagg caaaagtaaa aactgcaaag cgtcttaaaa   180
tagaagttca gaagccacat tatatcactt ctgttgcatt ctatcaaagc aagtcacaag   240
cccctgccaa tca                                                      253
```

<210> SEQ ID NO 49
<211> LENGTH: 183
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 49

```
cacacactcc cccattctga gccccaagag gctcatccct aaggatgtcc agagatccaa    60
gtgcagaagg agaatgtggt gaggctattt attcccccag tgccttccct gctgggctat   120
ggatgaacag tggctgactt catctaggaa agagctatgg cttctgtctc ctggagctca   180
cca                                                                 183
```

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 50

```
tgcaaacttt cacctggact t                                              21
```

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 51

```
cttgtgactt gctttgatag aatg                                           24
```

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 52

```
tgtccagaga tccaagtgca gaagg                                          25
```

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 53

```
                                                       -continued
gagctccagg agacagaagc catag                                        25

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 54
acattgaagc actccgcgac                                              20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 55
agagtggcag caaccaagct                                              20
```